(12) United States Patent
Radin et al.

(10) Patent No.: US 11,053,309 B2
(45) Date of Patent: Jul. 6, 2021

(54) METHODS FOR TREATING ACTIVE EOSINOPHILIC ESOPHAGITIS

(71) Applicants: REGENERON PHARMACEUTICALS, INC., Tarrytown, NY (US); Sanofi Biotechnology, Paris (FR)

(72) Inventors: Allen Radin, New York, NY (US); Jennifer D. Hamilton, Ridgefield, CT (US); Leda Mannent, Paris (FR)

(73) Assignees: Regeneron Pharmaceuticals, Inc., Tarrytown, NY (US); Sanofi Biotechnology, Paris (FR)

( * ) Notice: Subject to any disclaimer, the term of this patent is extended or adjusted under 35 U.S.C. 154(b) by 0 days.

(21) Appl. No.: 16/054,583

(22) Filed: Aug. 3, 2018

(65) Prior Publication Data
US 2019/0040126 A1 Feb. 7, 2019

Related U.S. Application Data

(60) Provisional application No. 62/541,242, filed on Aug. 4, 2017, provisional application No. 62/561,593, filed on Sep. 21, 2017.

(30) Foreign Application Priority Data

Mar. 8, 2018 (EP) .................................. 18305252

(51) Int. Cl.
| | |
|---|---|
| C07K 16/28 | (2006.01) |
| A61K 39/395 | (2006.01) |
| C07K 16/24 | (2006.01) |
| A61P 1/00 | (2006.01) |
| C07K 16/46 | (2006.01) |
| A61K 31/56 | (2006.01) |
| A61K 45/06 | (2006.01) |
| A61K 39/00 | (2006.01) |

(52) U.S. Cl.
CPC ........ *C07K 16/247* (2013.01); *A61K 39/3955* (2013.01); *A61P 1/00* (2018.01); *C07K 16/468* (2013.01); *A61K 2039/505* (2013.01); *A61K 2039/54* (2013.01); *A61K 2039/545* (2013.01); *A61K 2039/577* (2013.01); *C07K 16/2866* (2013.01); *C07K 2317/21* (2013.01); *C07K 2317/565* (2013.01); *C07K 2317/76* (2013.01)

(58) Field of Classification Search
None
See application file for complete search history.

(56) References Cited

U.S. PATENT DOCUMENTS

| | | |
|---|---|---|
| 5,599,905 A | 2/1997 | Mosley |
| 5,714,146 A | 2/1998 | Lewis |
| 5,717,072 A | 2/1998 | Mosley |
| 5,856,296 A | 1/1999 | Mosley |
| 5,985,280 A | 11/1999 | Ritter |
| 6,156,877 A | 12/2000 | Ritter |
| 6,391,581 B1 | 5/2002 | Mosley |
| 6,548,655 B1 | 4/2003 | Mosley |
| 6,716,587 B2 | 4/2004 | Mosley |
| 7,141,653 B2 | 11/2006 | Greenfeder |
| 7,186,809 B2 | 3/2007 | Pluenneke |
| 7,317,090 B2 | 1/2008 | Mosley |
| 7,422,742 B2 | 9/2008 | Greenfeder |
| 7,531,169 B2 | 5/2009 | Singh |
| 7,605,237 B2 | 10/2009 | Stevens |
| 7,608,693 B2 | 10/2009 | Martin |
| 7,794,717 B2 | 9/2010 | Stevens |
| 8,030,003 B2 | 10/2011 | Rothenberg |
| 8,075,887 B2 | 12/2011 | Martin |
| 8,075,897 B2 | 12/2011 | Spertini |
| 8,092,802 B2 | 1/2012 | Stevens |
| 8,092,804 B2 | 1/2012 | Eriksson |
| 8,252,284 B2 | 8/2012 | Singh |
| 8,324,192 B2 | 12/2012 | Dohil |
| 8,337,839 B2 | 12/2012 | Martin |
| 8,338,135 B2 | 12/2012 | Stevens |
| 8,497,528 B2 | 7/2013 | Lee |
| 8,604,171 B2 | 12/2013 | Singh |
| 8,637,239 B2 | 1/2014 | Furuta |
| 8,735,095 B2 | 5/2014 | Martin et al. |
| 8,945,559 B2 | 2/2015 | Dix |
| 9,238,692 B2 | 1/2016 | Dix |
| 9,290,574 B2 | 3/2016 | Kostic |

(Continued)

FOREIGN PATENT DOCUMENTS

| | | |
|---|---|---|
| EP | 0604693 | 7/1994 |
| EP | 0367566 | 5/1997 |

(Continued)

OTHER PUBLICATIONS

Marone et al, Frontiers un Pharmacology, 2019; pp. 1-13.*
Wegmann et al. Expert review of respiratory medicine, 2017; vol. 11, No. 9, pp. 675-677.*
Nicodeme et al. Clinical Gastroenterology and Hepatology, 2013; vol. 11, No. 9, pp. 1101-1107.*
Akiyama, et al., A Study on Indoor Allergens Measured in Home Environments of Adult-Asthmatic Patients, Housing Research Foundation, Research Annual Report, 1997, No. 24, Study No. 9620, 1-10.

(Continued)

*Primary Examiner* — Bridget E Bunner
*Assistant Examiner* — Fozia M Hamud
(74) *Attorney, Agent, or Firm* — Merchant & Gould, P.C.

(57) ABSTRACT

The present invention provides methods for treating, preventing or reducing the severity of active eosinophilic esophagitis. In certain embodiments, the present invention provides methods of increasing esophageal distensibility. The methods of the present invention comprise administering to a subject in need thereof a therapeutic composition comprising an interleukin-4/interleukin-13 (IL-4/IL-13) pathway inhibitor such as an anti-IL-4R antibody.

22 Claims, 12 Drawing Sheets

Specification includes a Sequence Listing.

(56) References Cited

U.S. PATENT DOCUMENTS

| | | |
|---|---|---|
| 9,574,004 B2 | 2/2017 | Ardeleanu |
| 10,059,771 B2 | 8/2018 | Mannent |
| 10,066,017 B2 | 9/2018 | Mannent |
| 10,137,193 B2 | 11/2018 | Pirozzi |
| 10,392,439 B2 | 8/2019 | Stahl |
| 10,435,473 B2 | 10/2019 | Dix |
| 10,485,844 B2 | 11/2019 | Radin |
| 2003/0103938 A1 | 6/2003 | Jinquan |
| 2003/0113387 A1 | 6/2003 | Tsuchida |
| 2003/0124121 A1 | 7/2003 | Pluenneke |
| 2005/0031609 A1 | 2/2005 | Hultsch |
| 2005/0074462 A1 | 4/2005 | Holmgren |
| 2005/0118176 A1 | 6/2005 | Mosley |
| 2005/0255532 A1 | 11/2005 | Ruben |
| 2005/0282181 A1 | 12/2005 | Yan |
| 2006/0013811 A1 | 1/2006 | Dina |
| 2007/0041976 A1 | 2/2007 | Pluenneke |
| 2007/0274996 A1 | 11/2007 | Carter |
| 2008/0054606 A1 | 5/2008 | Eriksson |
| 2009/0074793 A1 | 3/2009 | Martin |
| 2009/0098142 A1 | 4/2009 | Kasaian |
| 2009/0264392 A1 | 10/2009 | Warndahl |
| 2010/0047254 A1 | 2/2010 | Martin |
| 2011/0195500 A1 | 8/2011 | Rothenberg |
| 2012/0004205 A1 | 1/2012 | Rothenberg |
| 2012/0052072 A1 | 3/2012 | Martin |
| 2012/0097565 A1 | 4/2012 | Dix |
| 2012/0164080 A1 | 6/2012 | Hill |
| 2012/0207815 A1 | 8/2012 | Benhamou |
| 2013/0052190 A1 | 2/2013 | Collins |
| 2013/0078675 A1 | 3/2013 | Martin |
| 2013/0324435 A1 | 12/2013 | Rothenberg |
| 2014/0072583 A1 | 3/2014 | Ardeleanu |
| 2014/0187523 A1 | 7/2014 | Dohil |
| 2014/0271681 A1 | 9/2014 | Martin |
| 2014/0356372 A1 | 12/2014 | Stahl |
| 2015/0017176 A1* | 1/2015 | Kostic .................... A61K 31/56 424/142.1 |
| 2015/0185228 A1 | 7/2015 | Reisacher |
| 2015/0246973 A1 | 9/2015 | Graham |
| 2016/0152718 A1 | 6/2016 | Kostic |
| 2016/0185866 A1 | 6/2016 | Mannent |
| 2017/0333557 A1 | 11/2017 | Ardeleanu |
| 2018/0078603 A1 | 3/2018 | Radin |
| 2018/0094069 A1 | 4/2018 | Stahl |
| 2018/0094070 A1 | 4/2018 | Stahl |
| 2018/0179288 A1 | 6/2018 | Martin et al. |
| 2019/0169299 A1 | 6/2019 | Amin |
| 2019/0183973 A1 | 6/2019 | Hamilton |
| 2019/0345253 A1 | 11/2019 | Bansal |
| 2019/0367622 A1 | 12/2019 | Graham |
| 2020/0246416 A1 | 8/2020 | Radin |
| 2020/0299393 A1 | 9/2020 | Stahl |
| 2020/0332014 A1 | 10/2020 | Kostic |
| 2020/0345843 A1 | 11/2020 | Asrat |
| 2021/0033715 A1 | 2/2021 | Hamilton |
| 2021/0040222 A1 | 2/2021 | Bansal |

FOREIGN PATENT DOCUMENTS

| | | |
|---|---|---|
| EP | 1113818 B1 | 5/2006 |
| EP | 2022507 A1 | 2/2009 |
| EP | 1527100 | 7/2009 |
| JP | 05-246874 | 9/1993 |
| JP | 2006-131623 | 5/2006 |
| JP | 2016521713 | 7/2016 |
| RU | 2162711 | 2/2001 |
| RU | 2453303 C1 | 6/2012 |
| WO | WO 1992/19259 | 11/1992 |
| WO | WO 1994/14975 | 7/1994 |
| WO | WO 2001/092340 | 12/2001 |
| WO | WO 2003/048083 | 6/2003 |
| WO | WO 2005/047331 | 5/2005 |
| WO | WO 2005/085284 | 9/2005 |
| WO | WO 2006/003407 | 1/2006 |
| WO | WO 2006/072564 | 7/2006 |
| WO | WO 2006/083390 | 8/2006 |
| WO | WO 2008/054606 | 5/2008 |
| WO | 2008/116149 | 9/2008 |
| WO | WO 2009/124954 | 10/2009 |
| WO | WO 2010/053751 | 5/2010 |
| WO | WO 2010/065557 | 6/2010 |
| WO | WO 2010/120524 | 10/2010 |
| WO | WO 2011/026966 | 3/2011 |
| WO | WO 2012/047954 | 4/2012 |
| WO | WO 2012/094643 | 7/2012 |
| WO | WO 2012/177945 | 12/2012 |
| WO | WO 2013/051928 | 4/2013 |
| WO | WO 2013/088109 | 6/2013 |
| WO | 2013/116287 | 8/2013 |
| WO | WO 2013/155010 | 10/2013 |
| WO | 2014/031610 | 2/2014 |
| WO | WO 2014/039461 | 3/2014 |
| WO | WO 2014/059178 | 4/2014 |
| WO | 2014/122144 | 8/2014 |
| WO | 2014/205365 | 12/2014 |
| WO | WO 2014/197470 | 12/2014 |
| WO | 2015/006571 | 1/2015 |
| WO | 2015/127229 | 8/2015 |
| WO | WO 2016/077675 | 5/2016 |
| WO | 2017/143270 | 8/2017 |
| WO | 2018/045130 | 3/2018 |
| WO | 2018/057776 | 3/2018 |
| WO | 2018/151836 | 8/2018 |
| WO | 2018/201051 | 11/2018 |
| WO | 2019/089473 | 5/2019 |

OTHER PUBLICATIONS

Abonia et al. (2013) Journal of Allergy Clin Immunol "High prevalence of eosinophilic esophagitis in patients with inherited connective tissue disorders".

Aceves et al. (2009) Immunol Allergy Clin N Am 29:197-211 "Relationships Between Eosinophilic Inflammation, Tissue Remodeling, and Fibrosis in Eosinophilic Esophagitis".

Almagro et al., "Humanization of antibodies", (2008) Frontiers in Bioscience 13:1619-1633.

Arron et al. (2009) Am. J. Respir. Crit. Care Med. Online Abstracts Issue. 2009, B21 Airway Inflammation: New Information about Mediators and Biomarkers/Poster Discussion/Monday, May 18, 2009 "Peripheral Biomarkers of an IL-13 Induced Bronchial Epithelial Gene Signature in Asthma".

Assa'ad et al. (2011) Gastroenterology 141:1593-1604 "An Antibody Against IL-5 Reduces Numbers of Esophageal Intraepithelial Eosinophils in Children with Eosinophilic Esophagitis".

Assa'ad, Amal, What is new in the Treatment of Eosinophilic Esophagitis? Clinical and Translational Allergy 2011 (Suppl 1):569, doi: 10.1186/2045-7022-1-S 1-S69.

Bachert et al. (2005) Drugs 65(11):1537-1552 "Pharmacological management of nasal polyposis".

Bagnasco, Diego et al., "A critical evaluation of Anti-IL-13 and Anti-IL-4 Strategies in Severe Asthma", Int. Arch Allergy Immunol 2016; 170: 122-131.

Balint and Larrick (1993) Gene 137:109-118 "Antibody engineering by parsimonious mutagenesis".

Barnes (2008) The Journal of Clinical Investigation 118(11):3546-3556 "The cytokine network in asthma and chronic obstructive pulmonary disease".

Bateman et al. (2004) Am. J. Respir. Crit. Care Med. 170:836-844 "Can guideline-defined asthma control be achieved?"

Beck et al. (2014) New England Journal of Medicine 371(2): 130-139 "Dupilumab treatment in adults with moderate-to-severe atopic dermatitis".

Beyer et al. (2002) Journal of Allergy Clin Immunol 109(4):707-713 "Human milk-specific mucosal lymphocytes of the gastrointestinal tract display a $T_H 2$ cytokine profile".

Bhardwaj and Ghaffari (2012) Ann Allergy Asthma Immunol 109:155-159 "Biomarkers for eosinophilic esophagitis: a review".

Bieber, T., et al., "Atopic dermatitis: a candidate for disease-modifying strategy," Allergy 67 (2012) 969-975.

(56) References Cited

OTHER PUBLICATIONS

Blanchard and Rothenberg (2009) Immunol Allergy Clin N Am 29:141-148 "Chemotactic Factors Associated with Eosinophilic Gastrointestinal Diseases".
Blanchard et al. (2005) Clin Exp Allergy 35:1096-1103 "Inhibition of human interleukin-13-induced respiratory and oesophageal inflammation by anti-human-interleukin-13 antibody (CAT-354)".
Blanchard et al. (2006) The Journal of Clinical Investigation 116(2) "Eotaxin-3 and a uniquely conserved gene-expression profile in eosinophilic esophagitis".
Blanchard et al. (2007) Journal of Allergy Clin Immunol 120(6) "IL-13 involvement in eosinophilic esophagitis: Transcriptome analysis and reversibility with glucocorticoids".
Blanchard et al. (2010) The Journal of Immunology "Coordinate Interaction between IL-13 and Epithelial Differentiation Cluster Genes in Eosinophilic Esophagitis".
Blanchard et al. (2011) J Allergy Clin Immunol 127(1):208-217 "A striking local esophageal cytokine expression profile in eosinophilic esophagitis".
Blauvelt, Andrew, et al., "Long-term management of moderate-to-severe atopic dermatitis with dupilumab and concomitant topical corticosteroids (LIBERTY AD CHRONOS): a 1-year, randomised, double-blinded, placebo-controlled, phase 3 trial," www.thelancet.com, published online May 4, 2016, http://dx.doi.org/10.1016/S0140-6736(17)31191-1.
Brown-Whitehorn and Spergel (2010) Expert Rev Clin Immunol. 6:1:101-115 "The link between allergies and eosinophilic esophagitis: implications for management strategies".
Burmeister-Getz et al. (2009) J. Clin. Pharmacol. 49:1025-1036 "Human pharmacokinetics/pharmacodynamics of an interleukin-4 and interleukin-13 dual antagonist in asthma".
Burton, et al., "Direct effects of IL-4 on mast cells drive their intestinal expansion and increase susceptibility to anaphylaxis in a murine model of food allergy," Mucosal Immunology, Nov. 14, 2012, doi:10.1038/mi.2012.112.
Caldas et al. (2003) Molecular Immunology 39:941-952 "Humanization of the anti-CD18 antibody 6.7: an unexpected effect of a framework residue in binding to antigen".
Carter (2006) The Journal of Immunology 6:343-357 "Potent Antibody Therapeutics by Design".
Casset et al. (2003) Biochemical and Biophysical Research Communication 307:198-205 "A peptide mimetic of an anti-CD4 monoclonal antibody by rational design".
Chehade and Sampson (2009) Immunol Allergy Clin N Am 29:149-158 "The Role of Lymphocytes in Eosinophilic Gastrointestinal Disorders".
Cheng et al. (2012) Am J Physiol Gastrointest Liver Physiol 303:G1175-G1187 "Tissue remodeling in eosinophilic esophagitis".
Chien et al. (1989) Proc. Natl. Acad. Sci. 86:5532-5536 "Significant structural and functional change of an antigen-binding site by a distant amino acid substitution: Proposal of a structural mechanism".
Corren et al. (2010) American Journal of Respiratory and Critical Care Medicine 181(8):788-796 "A Randomized, Controlled, Phase 2 Study of AMG 317, an IL-4R Antagonist, in Patients with Asthma".
Cortes, J.R., et al., Proton pump inhibitors inhibit IL-4 and IL-13 signaling stat6 activation, European Journal of Immunology, (Sep. 2009) vol. 39, Supp.
Davies et al. (1996) Immunotechnol. 2(3):169-179 "Affinity improvement of single antibody VH domains: residues in all three hypervariable regions affect antigen binding".
Davis (2004) Seminars in Immunology 16:239-243 "The evolutionary and structural 'logic' of antigen receptor diversity".
De Pascalis et al. (2002) Journal of Immunology 169(6):3076-3084 "Grafting of "Abbreviated" Complementarity-Determining Regions Containing Specificity-Determining Residues Essential for Ligand Contact to Engineer a Less Immunogenic Humanized Monoclonal Antibody".

Dellon (2013) Dig Dis Sci "The Pathogenesis of Eosinophilic Esophagitis: Beyond the Eosinophil".
Desreumaux et al. (1996) Gastroenterology 110:768-774 "Interleukin 3, Granulocyte-Macrophage Colony-Stimulating Factor, and Interleukin 5 in Eosinophilic Gastroenteritis".
Durham, Andrew L. et al., "Targeted anti-inflammatory therapeutics in asthma and chronic obstructive lung disease", Airway Disease Section, Nat'l. Heart and Lung Institute, Imperial College London, UK, published Aug. 12, 2015, 12 pages.
Fillon et al. (2009) Immunol Allergy Clin N Am 29:171-178 "Epithelial Function in Eosinophilic Gastrointestinal Diseases".
Foote and Winter (1992) J. Mol. Biol. 224:487-499 "Antibody Framework Residues Affecting the Conformation of the Hypervariable Loops".
Foroughi et al. (2007) J Allergy Clin Immunol 120(3):594-601 "Anti-IgE Treatment of Eosinophil Associated Gastrointestinal Disorders".
Franciosi and Liacouras (2009) Immunol Allergy Clin N Am 29:19-27 "Eosinophilic Esophagitis".
Gavett et al. (1997) The American Physiological Society 272(16):L253-L261 "Interleukin-4 receptor blockade prevents airway responses induced by antigen challenge in mice".
Gevaert et al. (2006) Journal of Allergy and Clinical Immunology 118(5):1133-1141 "Nasal IL-5 levels determine the response to anti-IL-5 treatment in patients with nasal polyps".
Giusti et al. (1987) Proc. Natl. Acad. Sci. 84:2926-2930 "Somatic diversification of S107 from an antiphosphocholine to anti-DNA autoantibody is due to a single base change in its heavy chain variable region".
Groves et al. (2007) Aeroderm in AD Poster at St. John's Institute of Dermatology "Inhibition of IL-4 and IL-13 with an IL-4 mutein (Aeroderm) protects against flares in atopic eczema".
Grunewald et al. (1998) The Journal of Immunology 160(8):4004-4009 "An Antagonistic IL-4 Mutant Prevents Type I Allergy in the Mouse: Inhibition of the IL-4/IL-13 Receptor System completely Abrogates Humoral Immune Response to Allergen and Development of Allergic Symptoms in Vivo".
Gussow and Seemann (1991) Methods in Enzymology 203:99-121 "Humanization of Monoclonal Antibodies".
Hamilton, Jennifer D., et al., "Drug evaluation review: Dupilumab in atopic dermatitis," Immunotherapy (2015) 7(10), 1043-1058.
Highlights of Prescribing Information, DUPIXENT {dupilumab) injection, for subcutaneous use Initial U.S. Approval: 2017, U.S. Food and Drug Administration (FDA), Revised Mar. 2017.
Hijnen et al. (2004) J. Allergy Clin. Immunology 113(2): 334-340 "Serum thymus and activation-regulated chemokine (TARC) and cutaneous T Cell-attracting chemokine (CTACK) levels in allergic diseases: TARC and CTACK are disease-specific markers for atopic dermatitis".
Holm et al. (2007) Molecular Immunology 44:1075-1084 "Functional mapping and single chain construction of the anti-cytokeratin 8 monoclonal antibody TS1".
Holt et al. (2003) Trends in Biotechnology 21(11):484-490 "Domain antibodies: proteins for therapy".
Hong, Judith, et al., "Management of Itch in Atopic Dermatitis," Seminars in cutaneous Medicine and Surgery, vol. 30, No. 2, May 14, 2011, pp. 71-86, XP028240445.
Hopkins (2009) Clinical Otolaryngology 34(5):447-454 "Psychometric validity of the 22-item Sinonasal Outcome Test".
Hopkins et al. (2007) Otolaryngology-Head and Neck Surgery 137(4):555-561 "The Lund-Mackay staging system for chronic rhinosinusitis: How is it used and what does it predict?".
Ivashkiin, V. T., et al., "Eosinophilic esophagitis," a textbook for physicians, Moscow, "AISPI RAS" JSC, 14.02.2013, pp. 13-21, 57-62 No English translation. (Cited in Russian Office Action for RU Appl. No. 2016104400).
Ivashkin, V. T., et al., "Eosinophilic esophagitis: literature review and description of own survey," RJGHC, 2012, vol. 22, 1, pp. 71-81.
Jahnz-Rozyk et al. (2005) Allergy 60:685-688 "Serum thymus and activation-regulated chemokine, macrophage-derived chemokine and eotaxin as marker of severity of atopic dermatitis".

(56) References Cited

OTHER PUBLICATIONS

Junttila et al. (2008) J. Exp. Med. 205(11):2595-2608 "Tuning sensitivity to IL-4 and IL-13: differential expression of IL-4Rα, IL-13Rα1, and Υc regulates relative cytokine sensitivity".
Jyonouchi et al. (2013) Basic Mechanisms in Allergic Disease "Invariant Natural Killer T cells in children with Eosinophilic Esophagitis".
Kagami et al. (2003) Clin. Exp. Immunology 134:309-313 "Significant elevation of serum levels of eotaxin-3/CCL26, but not of eotaxin-2/CCL24, in patients with atopic dermatitis: serum eotaxin-3/CCL26 levels reflect the disease activity of atopic dermatitis".
Kakinuma et al. (2002) Clin. Exp. Immunol 127:270-273 "Serum macrophage-derived chemokine (MDC) levels are closely related with the disease activity of atopic dermatitis".
Kakinuma, Takashi et al. (2001) J. Allergy Clin. Immunol. 107(3):535-541 "Thymus and activation-regulated chemokine in atopic dermatitis: Serum thymus and activation-regulated chemokine level is closely related with disease activity".
Kakkar, Tarundeep et al. (2011) Pharmaceutical Research 28(10):2530-2542 "Population PK and IgE Pharmacodynamic Analysis of a Fully Human Monoclonal Antibody Against IL4 Receptor".
Katial (2009) Immunol Allergy Clin N Am 29:119-127 "Biomarkers for Nononcologic Gastrointestinal Disease".
Kelly and Liu (2014) World Allergy Organization Journal 7(S1):P8 "Poster 1013: IL-4R alpha antibody inhibits IgE production and airway remodeling in mouse model of house dust mite-induced eosinophilic asthma".
Kim et al. (2004) J Allergy Clin Immunol 114(6):1449-1455 "Rebound eosinophilia after treatment of hypereosinophilic syndrome and eosinophilic gastroenteritis with monoclonal anti-Il-5 antibody SCH55700".
Konikoff et al. (2006) Gastroenterology 131:1381-1391 "A Randomized, Double-Blind, Placebo-Controlled Trial of Fluticasone Propionate for Pediatric Eosinophilic Esophagitis".
Kopf et al. (1993) Letters to Nature 362:245-248 "Disruption of the murine IL-4 gene blocks Th2 cytokine responses".
Kostic et al. (2010) Clinical Immunology 135:S105-S106 "A Fully Human IL4Rα Antibody for Inhibition of IL-4/IL-13-driven TH2 Responses in Allergic Disease".
Kottyan et al. (2014) Nature Genetics "Genome-wide association analysis of eosinophilic esophagitis provides insight into the tissue specificity of this allergic disease".
Kulis et al. (2011) J. Allergy Clin Immunol 127:81-88 "Single-tree nut immunotherapy attenuates allergic reactions in mice with hypersensitivity to multiple tree nuts".
Leung et al. (2003) The New England Journal of Medicine 348:986-993 "Effect of Anti-IgE Therapy in Patients with Peanut Allergy".
Leung et al. (2004) The Journal of Clinical Investigation 113(5):651-657 "New insights into atopic dermatitis".
Lezcano-Meza et al. (2003) Allergy 58(10):1011-1017 "Interleukin (IL)-4 and to a lesser extent either IL-13 or interferon-gamma regulate the production of eotaxin-2/CCL24 in nasal polyps".
Liacouras et al. (2011) J Allergy Clin Immunol 128(1) "Eosinophilic esophagitis: Updated consensus recommendations for children and adults".
Lin et al (2007) Clinical Reviews in Allergy & Immunology 33(3):167-177 "Role of Bacterial Pathogens in Atopic Dermatitis".
Liu et al. (1999) Gene Therapy 6:1258-1266 "Hydrodynamics-based transfection in animals by systemic administration of plasmid DNA".
Lucendo and Sanchez-Cazalilla (2012) Expert Rev. Clin. Immunol. 8(8):733-745 "Adult versus pediatric eosinophilic esophagitis: important differences and similarities for the clinician to understand".
Ludmila and Xia (2014) World Allergy Organization Journal 7(1):p. 8 "Poster 1013: IL-4R alpha antibody inhibits IgE production and airway remodeling in mouse model of house dust mite-induced eosinophilic asthma".

Lwin et al. (2011) Modern Pathology 24:556-563 "Eosinophilic gastritis: histopathological characterization and quantification of the normal gastric eosinophil content".
MacCallum et al. (1996) J. Mol. Biol. 262:732-745 "Antibody-antigen Interactions: Contact Analysis and Binding Site Topography".
Maliszewski et al. (1994) Proc. Soc. Exp. Biol. Med. 206(3):233-237 "In vivo biological effects of recombinant soluble interleukin-4 receptor".
Mannon et al. (2012) Gut 61(12):1765-1773 "Interleukin 13 and its role in gut defence and inflammation".
Mariuzza et al. (1987) Ann. Rev. Biophys. Biophys. Che. 16:139-159 "The Structural Basis of Antigen-Antibody Recognition".
Martel, Britta C., et al., "Translational animal Models of Atopic Dermatitis for Preclinical Studies," Yale Journal of Biology and Medicine 90 (2017), pp. 389-402.
Masterson et al. (2011) Curr Opin Gastroenterol. 27(6):515-522 "Update on clinical and immunological features of eosinophilic gastrointestinal diseases".
Mathias, et al., "IgE-mediated systemic anaphylaxis and impaired tolerance to food antigens in mice with enhanced IL-4 receptor signaling," Journal of Allergy and Clinical Immunology, 2011, vol. 127, No. 3, 795-805, e1-e6.
Mishra and Rothenberg (2003) Gastroenterology 125:1419-1427 "Intratracheal IL-13 Induces Eosinophilic Esophagitis by an IL-5, Eotaxin-1, and STAT6-Dependent Mechanism".
Mishra et al. (2001) J Clin. Invest. 107:83-90 "An etiological role for aeroallergens and eosinophils in experimental esophagitis".
Mishra et al. (2002) The Journal of Immunology 168:2464-2469 "IL-5 Promotes Eosinophil Trafficking to the Esophagus".
Moldoveanu et al. (2009) Journal of Inflammation Research 2:1-11 "Inflammatory mechanisms in the lung".
Molfino et al. (2012) Clinical & Experimental Allergy 42(5):712-737 "Molecular and clinical rationale for therapeutic targeting of interleukin-5 and its receptor".
Morioka et al. (2009) British Journal of Dermatology 160(6):1172-1179 "IL-4/IL-13 antagonist DNA vaccination successfully suppresses Th2 type chronic dermatitis".
Muller et al. (1993) Journal of Immunology 150:5576-5584 "Th2 cells mediate IL-4-dependent local tissue inflammation".
Nadeau et al. (2011) J. Allergy Clin. Immunol 127(6) Letters to the Editor "Rapid oral desensitization in combination with omalizumab therapy in patients with cow's milk allergy".
Nadeau, et al., "Oral Immunotherapy and Anti-IgE Antibody-Adjunctive Treatment for Food Allergy," Immunology and Allergy clinics of North America, 2012, vol. 32, No. 1, 111-133.
Nguyen et al. (2011) Immunological Reviews 242(1):258-271 "Immune modulation for treatment of allergic disease".
Niederberger (2009) Immunology Letters 122:131-133 "Allergen-specific immunotherapy".
Niranjan et al. (2013) Immunology and Cell Biology pp. 1-8 "Pathogenesis of allergen-induced eosinophilic esophagitis is independent of interleukin (IL)-13".
Noel et al. (2004) The New England Journal of Medicine 351:940-941 "Eosinophilic Esophagitis".
Novartis (2013) QAX576 "A double blinded, randomized, placebo-controlled trial of intravenous QAX576 in the treatment of eosinophilic esophagitis".
Oetjen, Landon K., et al., "Sensory Neurons Co-opt Classical Immune Signaling Pathways to Mediate Chronic Itch," Sep. 21, 2017, Cell 171, 217-228.
Oh et al. (2010) Eur Respir Rev 19(115):46-54 "Investigational therapeutics targeting the IL-4/IL-13/STAT-6 pathway for the treatment of asthma".
Ohno et al. (1985) Proc. Natl. Acad. Sci. USA 82:2945-2949 "Antigen-binding specificities of antibodies are primarily determined by seven residues of $V_H$".
Ong (2012) Expert Opinion on Emerging Drugs 17(2):129-133 "Editorial update on emerging treatments of atopic dermatitis".
Otani et al. (2013) Journal of Allergy and Clinical Immunology 131(6):1576-1582 "Anti-IL-5 therapy reduces mast cell and IL-9 cell munbers in pediatric patients with eosinophilic esophagitis".

(56) References Cited

OTHER PUBLICATIONS

Otulana et al. (2011) Am. J. Respir. Crit. Care Med. 183:A6179 "A Phase 2b Study of Inhaled Pitrakinra, An IL-4R/IL-13 Antagonist, Successfully Identified Responder Subpopulations of Patients with Uncontrolled Asthma".
Oyoshi et al. (2009) Advances in Immunology 102:135-226 "Cellular and Molecular Mechanisms in Atopic Dermatitis".
Paton, D. M., "Dupilumab: human monoclonal antibody against IL-4Ralpha for moderate to severe atopic dermatitis," Drugs Today, vol. 53, No. 9, 1 Sep. 2017, pp. 477-487, XP055465888.
Peserico et al. (2008) British Journal of Dermatology 158:801-807 "Reduction of relapses of atopic dermatitis with methylprednisolone aceptonate cream twice weekly in addition to maintenance treatment with emollient: a multicentre, randomized, double-blind, controlled study".
Petry et al. (2012) Anais Brasileiro De Dermatologia 87(5):732-733 "Bacterial skin colonization and infections in patients with atopic dermatitis".
Prieto and Richter (2013) Curr Gastroenterol Rep 15:324 "Eosinophilic Esophagitis in Adults: an Update on Medical Management".
Prussin et al. (2009) J Allergy Clin Immunol. 124(6):1326-1332 "Eosinophilic gastrointestinal disease and peanut allergy are alternatively associated with IL-5+ and IL-5-TH2 responses".
Rafi et al. (2010) Allergy and Asthma Proceedings 31(1):76-83 "Effects of omalizumab in patients with food allergy".
Rayapudi et al. (2010) Journal of Leukocyte Biology 88 "Indoor insect allergens are potent inducers of experimental eosinophilic esophagitis in mice".
Receptos, Inc. 2013 Annual Report.
Ring et al. (2012) J. Eur. Acad. Dermatol. Venereol. 26(8):1045-1060 "Guidelines for treatment of atopic eczema (atopic dermatitis) Part 1".
Roitt et al. (2001) Mosby-Harcourt Publishers Limited, Immunology—Sixth Edition "Antigen Presentation" pp. 110-111.
Roll et al. (2006) J. Investig Allergol Clin Immunol 16(2):79-85 "Safety of specific immunotherapy using a four-hour ultra-rush induction scheme in bee and wasp allergy".
Romaniuk, L.I., "Allergan-specific immunotherapy: mechanisms, methods and efficacy", Clinical Immunology, Allergology and Infectology, 2012, special issue, pp. 44-47. (with English translation of the cited portion).
Rothenberg (2004) J Allergy Clin Immunol 113(1):11-28 "Eosinophilic gastrointestinal disorders (EGID)".
Rothenberg (2009) Gastroenterology 137:1238-1249 "Biology and Treatment of Eosinophilic Esophagitis".
Rudikoff et al. (1982) Proc. Natl. Acad. Sci. 79:1979-1983 "Single amino acid substitution altering antigen-binding specificity".
Russian Official Action from Russian Federation for RU Application 2016104400, dated Oct. 6, 2017, with translation, 4 pages.
Saeki, Hidehisa, "Guidelines for Management of Atopic Dermatitis", (Advances in Medicine, Special Issue, 2009, vol. 228(1):75-79 in part), cited in the Japanese Patent Application No. 2015-531149.
Sampson et al. (2011) J. Allergy Clin Immunol. 127(5) Letters to the Editor, "A phase II, randomized, double-blind, parallel-group, placebo-controlled oral food challenge trial of Xolair (omalizumab) in peanut allergy".
Sanofi and Regeneron Report Positive Proof-of-Concept Data for Dupilumab, an IL-4R alpha Antibody, in Atopic Dermatitis, 71st Annual Meeting of the American Academy of Dermatology (2013) http://files.shareholder.com/downloads/REGN/2689212012x0x640531/794a7e54-6904-416b-ba38-a4ccc1726852/REGN_News_2013_3_2_General_Releases.pdf.
Sanofi with Regeneron Pharmaceuticals "An Evaluation of Dupilumab in Patients with Nasal Polyposis and Chronic Symptoms of Sinusitis" Trial in Progress, Jun. 2014. ClinicalTrials.gov Identifier: NCT01920893. Retrieved from the Internet URL: http://clinicaltrials.govishow/NCT01920893 Accessed on Sep. 29, 2014.
Sanofi, "Positive Phase 2a Results of Dupilumab in Asthma in the New England Journal of Medicine," May 21, 2013, Regeneron Pharmaceuticals, Inc.
Sanofi/Regeneron Press Release, "Sanofi and Regeneron Report Positive Results with Sarilumab in First Phase 3 Rheumatoid Arthritis Registration Trial", Paris, France and Tarrytown, NY, Nov. 22, 2013, 3 pages.
Sato et al. (1993) J. Immunol. 150(7):2717-2723 "Recombinant soluble murine IL-4 receptor can inhibit or enhance IgE responses in vivo".
Scavuzzo et al. (2005) Biomedicine & Pharmacotherapy 59(6):323-9 "Inflammatory mediators and eosinophilia in atopic and non-atopic patients with nasal polyposis".
Schmidt-Weber (2012) Chem Immunol Allergy 96:120-125 "Anti-IL-4 as a New Strategy in Allergy".
Schmitt et al. (2007) J. Of Allergy and Clinical Immunology 120(6):1389-1398 "What are the best outcome measurements for atopic eczema? A systematic review".
Schneider et al. (2013) J. Allergy Clin Immunol 132(6):1368-1374 "A pilot study of omalizumab to facilitate rapid oral desensitization in high-risk peanut-allergic patients".
Sekiya et al. (2002) Allergy 57:173-177 "Increased levels of a TH2-type CC chemokine thymus and activation-regulated chemokine (TARC) in serum and induced sputum of asthmatics".
Silverberg J.I., et al., "Dupilumab treatment induces rapid clinical improvement of itch in patients with moderate-to-severe atopic dermatitis" Paper presented at: American Academy of Dermatology—76th Annual Meeting; Feb. 16-20, 2018; San Diego, CA, USA.
Silverberg J.I., et al., P481, "Dupilumab treatment rapidly improves itch in patients with moderate-to-severe atopic dermatitis" an Allergy Asthma Immunol. 2017;119(suppl 5):S95.
Simpson, E.L., et al., "Two Phase 3 Trials of Dupilumab versus Placebo in Atopic Dermatitis," The New England Journal of Medicine, Oct. 1, 2016, DOI: 10.1056/NEJMoa1610020.
Simpson, Eric L. et al., "Dupilumab therapy provides clinically meaningful improvement in patient-reported outcomes (PROs): A phase IIb, randomized, placebo-controlled, clinical trial in adult patients with moderate to severe atopic dermatitis (AD)", Journal of the American Academy of Dermatology, Mosby, Inc., US, vol. 75, No. 3, Jun. 4, 2016.
Simpson, Eric L. et al., "Patient burden of moderate to severe atopic dermatitis (AD): Insights from a phase 2b clinical trial of dupilumab in adults," Journal of the American Academy of Dermatology, Mosby, Inc., US, vol. 74, No. 3, Jan. 14, 2016.
Slager et al. (2012) Journal of Allergy, Asthma and Immunology 130(2):516-522.e4 "IL-4 Receptor Polymorphisms Predict Reduction in Asthma Exacerbations During Response to an Anti IL-4 Receptor Antagonist".
Spirin (1986) Vysshaya shkola, Moscow, pp. 17-23 "Molecular Biology Ribosome structure and protein biosynthesis", original Russian article and English language translation of same provided by foreign associate handling local prosecution of Russian application No. 2011120194.
Stein et al. (2006) J Allergy Clin Immunol 118(6):1312-1319 "Anti-IL-5 (mepolizumab) therapy for eosinophilic esophagitis".
Steinke and Borish (2001) Respiratory Research 2(2):1-5 "Th2 cytokines and asthma Interleukin-4: its role in the pathogenesis of asthma, and targeting it for asthma treatment with interleukin-4 receptor antagonists".
Stone et al. (2008) Clinical & Experimental Allergy 38(12):1858-1865 "Immunomodulatory therapy of eosinophil-associated gastrointestinal diseases".
Strauman (2009) Immunol Allergy Clin N Am 29:11-18 "Clinical Evaluation of the Adult who has Eosinophilic Esophagitis".
Straumann (2005) J Allergy Clin Immunol 115(2):418-419 "Eosinophilic esophagitis: Escalating epidemiology?".
Straumann et al. (2001) J Allergy Clin Immunol 108(6):954-961 "Idiopathic eosinophilic esophagitis is associated with a $T_H2$-type allergic inflammatory response".
Straumann et al. (2009) Gut "Anti-interleukin-5 antibody treatment (mepolizumab) in active eosinophilic oesophagitis: a randomized, placebo-controlled, double-blind trial".
Tazawa et al. (2004) Arch Dermatol Res 295:459-464 "Relative importance of IL-4 and IL-13 in lesional skin of atopic dermatitis".

(56) References Cited

OTHER PUBLICATIONS

Tepper et al. (1990) Cell 52:457-467 "IL-4 Induces Allergic-like Inflammatory Disease and Alters T Cell Development in Transgenic Mice".
Terui, et al., "Learning from Fungus Allergy in Atopic Dermatitis Patients," Japan J. Med. Mycol, 2000, vol. 41, No. 3, 157-160.
Thaci, Diamant et al.: "Efficacy and Safety of Dupilumab in Adults with Moderate-to-Severe Atopic Dermatitis Inadequately Controlled by Topical Treatments: A Randomised, placebo-controlled, dose-ranging phase 2b trial," The Lancet, The Lancet Publishing Group, GB, vol. 387, No. 10013, Oct. 8, 2015.
Tomkinson et al. (2001) J. Immunol 166:5792-5800 "A Murine IL-4 Receptor Antagonist that Inhibits IL-4- and IL-13-induced Responses Prevents Antigen-Induced Airway Eosinophilia and Airway Hyper-responsiveness".
Tsianakas, Athanasios et al., "Dupilumab: A Milestone in the Treatment of Atopic Dermatitis," The Lancet, The Lancet Publishing Group, GB vol. 387, No. 10013, Oct. 8, 2015.
Vajdos et al. (2002) Journal of Molecular Biology 320(2):415-428 "Comprehensive functional maps of the antigen-binding site of an anti-ErbB2 antibody obtained with shotgun scanning mutagenesis".
Veerappan et al. (2009) Clinical Gastroenterology and Hepatology 7:420-426 "Prevalence of Eosinophilic Esophagitis in an Adult Population Undergoing Upper Endoscopy: A Prospective Study".
Vestergaard et al. (2000) The Journal of Investigative Dermatology 115(4):640-646 "A $Th_2$ Chemokine, TARC, Produced by Keratinocytes May Recruit $CLA^+CCR4^+$ Lymphocytes into Lesional Atopic Dermatitis Skin".
Virchow et al. (1994) Lung 172:313-334 "Cellular and immunological markers of allergic and intrinsic bronchial asthma".
Walker et al. (1993) Clinical and Experimental Allergy 23:145-153 "Atopic dermatitis: correlation of peripheral blood T cell activation, eosinophilia and serum factors with clinical severity".
Wang and Liu (2008) Current Opinion in Immunology 20:697-702 "The IL-17 cytokine family and their role in allergic inflammation".
Wang, et al., "Peanut-induced intestinal allergy is mediated through a mast cell-IgE-FceRI-IL-13 Pathway," Journal of Allergy and Clinical Immunology, 2010, vol. 126, No. 2, 306-316, e1-e12.
Wark et al. (2006) Advanced Drug Delivery Reviews 58:657-670 "Latest technologies for the enhancement of antibody affinity".
Watson et al. (2011) Allergy, Asthma & Clinical Immunology 7:S4 "Atopic dermatitis".
Weihrauch et al. (2005) Cancer Research 65:5516-5519 "Elevated Serum Levels of CC Thymus and Activation-Related Chemokine (TARC) in Primary Hodgkin's Disease: Potential for a Prognostic Factor".
Weinbrand-Goichberg et al. (2013) Immunol Res "Eosinophilic esophagitis: an immune-mediated esophageal disease".
Wenzel et al. (2007) Lancet 370:1422-1431 "Effect of an interleukin-4 variant on late phase asthmatic response to allergen challenge in asthmatic patients: results of two phase 2a studies".
Wenzel et al. (2010) European Respiratory Society, Annual Congress 2010, "ERS—Programme" pp. 3980.
Wenzel et al. (2013) New England Journal of Medicine 368(26):2455-2466 "Dupilumab in Persistent Asthma with Elevated Eosinophil Levels".
Wershil (2009) Immunol Allergy Clin N Am 29:189-195 "Exploring the Role of Mast Cells in Eosinophilic Esophagitis".
Whalley et al. (2004) British Journal of Dermatology 150:274-283 "A new instrument for assessing quality of life in atopic dermatitis: international development of the Quality of Life Index for Atopic Dermatitis (QoLIAD)".
Wilhelm and Stockinger (2011) Frontiers in Immunology 2(68) "Innate lymphoid cells and type 2 (Th2) mediated immune responses-pathogenic or beneficial?"
Wills-Karp and Finkelman (2008) Science Signaling 1(51) "Untangling the Complex Web of IL-4 and IL-13 Mediated Signaling Pathways".
Winkler et al. (2000) J. Immunol. 165(8):4505-4514 "Changing the Antigen Binding Specificity by Single Point Mutations of an Anti-p24 (HIV-1) Antibody".
Winter and Harris (1993) Immunology Today 14(6):243-246 "Humanized Antibodies".
Wong, et al., "Guidelines for the management of atopic dermatitis (eczema) for pharmacists," CPJ/RPC, Sep./Oct. 2017, vol. 150, No. 5.
Wu et al. (1999) Journal of Molecular Biology 294:151-162 "Humanization of a murine monoclonal antibody by simultaneous optimization of framework and CDR residues".
Yamanaka et al. (2011) Curr Probl Dermatol 41:80-92 "The Role of Cytokines/Chemokines in the Pathogenesis of Atopic Dermatitis".
Yan and Shaffer (2006) World J Gastroenterol 12(15):2328-2334 "Eosinophilic esophagitis: A newly established cause of dysphagia".
Zuo et al. (2010) Journal of Immunology 185:660-669 "IL-13 Induces Esophageal Remodeling and Gene Expression by an Eosinophil-Independent, IL-13R{alpha}2-Inhibited Pathway".
Zurawski et al. (1995) J. Biol. Chem. Am. Society of Biochemical Biologists 270(23):13869-13878 "The primary binding subunit of the human Interleukin-4 receptor is also a component of the Interleukin-13 receptor".
Vakharia, Paras P. et al., "Monoclonal Antibodies for Atopic Dermatitis: Progress and Potential", BioDrugs (2017) 31:409-422.
Ul-Haq, Zaheer et al., "Interleukin-4 receptor signaling and its binding mechanism: A therapeutic insight from inhibitors tool box", Cytokine & Growth Factor Review 32 (2016) 3-15.
Mueller, Thomas D. et al., "Structure, binding, and antagonists in the IL-4/IL-13 receptor system", Biochimica et Biophysica Acta (2002) 237-250.
Regeneron: "Highlights of Prescribing Information See 17 for Patient Counseling Information and FDA-approved patient labeling. Revised: Mar. 2017 Full Prescribing Information: Contents 1 Indications and Usage 2 Dosage and Administration 2.1 Dosage 2.2 Important Administration Instructions 2.3 Preparation for Use", (Apr. 7, 2017), XP055534130, Retrieved from the Internet: URL: https://web.archive.org/web/20170407151633if_/https://www.regeneron.com/sites/default/files/Dupixent_FPI.pdf, 4 pages.
Huang, Evie et al: "Severe Atopic Dermatitis in Children", Current Allergy and Asthma Reports, Current Science, US, vol. 18, No. 6, May 10, 2018, pp. 1-8.
Akinlade, B. et al: "Conjunctivitis in dupilumab clinical trials", British Journal of Dermatology,. (Mar. 9, 2019), pp. 1-15.
Regeneron: "Dupixent: Highlights of Prescribing Information", (Mar. 1, 2019), pp. 1-8, XP55610296, Retrieved from the Internet: URL: https://dlegnxy4jxlq3f.cloudfront.net/Regeneron/Dupixent_FPI.pdf, 8 pgs.
Paller et al: "Early and sustained, clinically meaningful responses with dupilumab treatment in a phase 3 trial in adolescents with moderate-to-severe atopic dermatitis", Pediatric Dermatology, vol. 36, No. Suppl. 1, (Apr. 29, 2019), p. S4.
Database EMBASE [Online], Elsevier Science Publishers, AMSTERDAM,NL; (May 1, 2019), Cork M. J: "605 Efficacy and safety of dupilumab in adolescent patients with moderate-to-severe atopic dermatitis", XP002793331, Database accession No. EMB-002001809007 abstract, 3 pages.
Database EMBASE [Online], Elsevier Science Publishers, Amsterdam,NL; (May 1, 2019), Paller, A.S.: "621 Dupilumab in adolescents with moderate-to-severe atopic dermatitis and a history of inadequate response, or intolerance to cyclosporine: subgroup analysis from a pivotal 16-week trial", XP002793332, Database accession No. EMB-002001808313, Abstract, 2 pages.
Kopp, M.V. et al., "Combination of omalizumab and specific immunotherapy is superior to immunotherapy in patients ith seasonal allergic rhinoconjunctivitis and co-morbid seasonal allergic asthma", Clinical and Experimental Allergy, vol. 39, No. 2, pp. 271-279, published on Jan. 22, 2009.
PCT ISRWO for International Patent Application No. PCT/US2018/045195, dated Oct. 4, 2018, 19 pages.
Dellon, Evan S. et al., "A Randomized, Double-Blind, Placebo-Controlled Trial of a Novel Recombinant, Humanized, Anti-Interleukin-13 Monoclonal Antibody (RPC4046) in Patients with Active Eosinophilic Esophagitis: Results of the HEROES Study",

(56) References Cited

OTHER PUBLICATIONS

Oct. 14, 2016, retrieved from the Internet on Sep. 20, 2018 at: https://www.eventscribe.com/2016/ACG/QRcode.asp?Pres=178380, 3 pages.

Rothenberg, Marc E. et al., "Intravenous anti-IL-13 mAb QAX576 for the Treatment of eosinophilic esophagitis", Journal of Allergy and Clinical Immunology, vol. 135, No. 2, Feb. 1, 2015, pp. 500-507.

Hirano, Ikuo et al., "Dupilumab Efficacy and Safety in Adult Patients With Active Eosinophilic Esophagitis: a Randomized Double-Blind Placebo-Controlled Phase 2 Trial", Oct. 13, 2017, retrieved from the internet on Sep. 20, 2018 at: http://files.shareholder.com/downloads/REGN/6138593856x0x959724/16AF93AE-DAF8-480A-8301-311C91E8FA41/Presentation.pdf, 20 pages.

Hirano, Ikuo et al., "Sa1113—Correlation Between Esophageal Distensibility and Objective Measures of Disease in Patients with Active Eosinophilic Esophagitis: A Post HOC Analysis of a Randomized, Placebo-Controlled, Phase 2 Dupilumab Trial", abstract, Gastroenterology, vol. 154, No. 6, May 1, 2018, 1 page.

Collins, Margaret H. et al., "Sa1151—Baseline Characteristics and Correlation Between Dysphagia and Disease Activity in Patients with Eosinophilic Esophagitis in a Randomized, Placebo-Controlled, Phase 2 Dupilumab Trial", abstract, Gastroenterology, vol. 154, No. 6, May 1, 2016, 1 page.

Pesek, Robert D. et al., "Emerging drugs for eosinophilic esophagitis", Expert Opinion on Emerging Drugs, vol. 23, No. 2, Apr. 3, 2018, 12 pages.

Clinical Trials Study No. NCT01312961—"Efficacy, Safety, and Tolerability of Dupilumab in Patients with Persistent Moderate to Severe Eosinophilic Asthma", In: ClinicalTrials.gov, A service of the U.S. National Institutes of Health, First Received: Mar. 11, 2011, 10 pages, Available from: https://clinicaltrials.gov/ct2/show/NCT01312961.

Blanchard, Carine et al., "Eosinophilic esophagitis: Pathogenesis, genetics, and therapy", J. Allergy Clin. Immunol., 2006; 118: 1054-9.

Straumann et al., "Anti—TNF-a (infliximab) therapy for severe adult eosinophilic esophagitis", J Allergy Clin Immunol, 2008, 122:425-427.

European Notice of Opposition in Application 13765844.9, mailed Feb. 22, 2019, 34 pages.

Nguyen, Tran Hoai et al., "Future Forms of Immunotherapy and Immunomodulators in Allergic Disease", Immunol Allergy Clin N Am 31 (2011); 343-365.

Antoniu, Sabina, "Pitrakinra, a Dual IL-4R/IL-13 Antagonist for the Potential Treatment of Asthma and Eczema", Current Opinion in Investigational Drugs 2010 11 (11): 1286-1294.

International Investigative Dermatology, Edinburgh, Conference Posters, May 8-11, 2013, 4 pages.

Abstracts, "Human Clinical Research and Therapeutics", Journal of Investigative Dermatology vol. 133, Supplement 1, (2013), pp. 5159-5190, Abstracts 1042, and 1048 to 1050, http://apps.webofknowledge.com/full_record_do?product=WOS&search_mode=GeneralSearch&qid=2&SID=E6MDFsiCnXC9MfROx21&page=1&doc=1, 32 pages.

Bankhead, Charles, "IL-4 Antibody Tames Atopic Dermatitis", Medpage Today Article, https://www.medpagetoday.com/meetingcoverage/aad/37636, Mar. 3, 2013, 3 pages.

Clinical Trials, Study NCT01548404—"Study of REGN668 in Adult Patients With Extrinsic Moderate-to-Severe Atopic Dermatitis", first publication of clinical study protocol, Mar. 7, 2012, 7 pages.

Clinical Trials, Study NCT01548404—"Study of Dupilumab in Adult Patients with Extrinsic Moderate-to-severe Atopic Dermatitis", final publication of clinical study protocol, Aug. 27, 2015, 8 pages.

Clinical Trials, Study NCT00676884—"A Phase Study to Investigate the Effects of Repeated Administration of AeroDerm in Subjects with Atopic Dermatitis", Aeroderm first publication of clinical study protocol in TCS resistant moderate-to-severe AD, May 13, 2008, 6 pages.

Garriga, A., "71st Annual Meeting of the American Academy of Dermatology (AAAD) . . . Miami Beach, FL, Mar. 1-5, 2013", Drugs of the Future 2013, 38(4): 275-279, Apr. 2013, https://journals.prous.com/journals/servlet/xmlxls/pk_journals.xml_toc_pr?p_JournalID=2&p_IssueID=1186, 5 pages.

British Society for Allergy and Clinical Immunology (BSACI) Abstracts of the 2013 Annual Meeting (dated Jul. 8-10, 2013), Clinical & Experimental Allergy, 43, 1428-1472, Nov. 22, 2013, https://onlinelibrary.wiley.com/toc/13652222/2013/43/12, 45 pages.

Clinical Trials, Study NCT01639040—"Study to Assess the Safety of REGN668 (SAR231893) Administered Concomitantly with Topical Corticosteroids (TCS) in Patients with Moderate-to-severe Atopic Dermatitis (AD)", Concomitant treatment with TCS, Jul. 11, 2012, 6 pages.

Journal of Allergy & Clinical Immunology: Abstracts at conference; https://www.jacionline.org/issue/S0091-6749(13)X0013-2, Feb. 2013, 1 page.

Joost, T.H. Van, "Cyclosporin in atopical dermatitis: a multicentre placebo-controlled study", Journal of the America Academy of Dermatology, (1992), vol. 27, Issue 6, Part 1, pp. 922-928.

BSACI News Report confirming BSACI conference date of Jul. 8-10, 2013, 2 pages.

Regeneron 2011 Annual Report (Apr. 2011), 12 pages.

ClinicalTrials.gov archive, History of Changes for Study: NCT01548404, "Study of Dupilumab in Adult Patients with Extrinsic Moderate-to-Severe Atopic Dermatitis", (Apr. 19, 2012), 7 pages.

ClinicalTrials.gov archive, History of Changes for Study: NCT01259323, "Sequential Ascending Dose Study to Assess the Safety and Tolerability of REGN668 (SAR231893) in Patients With Atopic Dermatitis", (May 31, 2012), 6 pages.

Blankestijn, Mark et al., "Could Duratumumab be used to treat severe allergy?", Journal of Allergy and Clinical Immunology, vol. 139, No. 5, Jan. 19, 2017, p. 1677-1678.e3.

Nagaraju et al., "Bortezomib treatment diminishes hazelnut-induced intestinal anaphylaxis in mice: Immunomodulation", European Journal of Immunology, vol. 46, No. 7, May 11, 2016, pp. 1727-1736.

Winter, Oliver et al., "Pathogenic Long-Lived Plasma Cells and Their Survival Niches in Autoimmunity, Malignancy, and Allergy", The Journal of Immunology, vol. 189, No. 11, Nov. 19, 2012, pp. 5105-5111.

Hirano, Ikuo et al., "Efficacy of Dupilumab in a Phase 2 Randomized Trial of Adults with Active Eosinophilic Esophagitis", Gastroenterology 2020; 158: 111-122.

Healio Gastroenterology, "Novel therapy improved disease features in EoE", Oct. 8, 2019, located online at: https://www.healio.com/news/gastroenterology/20191008/novel-therapy-improves-disease-features-in-eoe, 2 pages.

De Genst, Erwin et al., "Antibody repertoire development in camelids", Developmental and Comparative Immunology, 30 (2006); 187-198.

Ward, E. Sally et al., "Binding activities of a repertoire of single immunoglobin variable domains secreted from *Escherichia coli*", Nature, 1989, 341 :544-546.

Barthelemy, Pierre et al., "Comprehensive analysis of the factors contributing to the stability and solubility of autonomous human VH domains", Journal of Biological Chemistry, 2008, 283:3639-3654.

Choi, Yoonjoo et al., "Predicting antibody complementarity determining region structures without classification", Molecular Biosystems, 2011, 7:3327-334.

Griffiths, Andrew et al., "Human anti-self antibodies with high specificity from phage display libraries", The EMBO Journal, 1993, 12:725-734.

Klimka et al., "Human anti-CD30 recombinant antibodies by guided phage antibody selection using cell panning", British Journal of Cancer, 2000, 83:252-260.

Beiboer, Sigrid et al., "Guided selection of a pan carcinoma specific antibody reveals similar binding characteristics yet structural divergence between the original marine antibody and its human equivalent", Journal of Molecular Biology, 2000; 296:833-849.

(56) References Cited

OTHER PUBLICATIONS

Chan, L.S. et al., "Expression of Interleukin-4 in the epidermis of transgenic mice results in pruritic inflammatory skin disease: an experimental animal model to study atopic dermatitis", J. Invest. Dermatol., 2001, 117: 977-983.

Phan, N.Q. et al., "Assessment of pruritus intensity: prospective study on validity and reliability of the visual analogue scale, numeric rating scale, and verbal rating scale in 471 patients with chronic pruritis", Acta. Derm. Venereol., 2012, 92: 502-507.

Cork et al., "An open-label phase IIa trial assessing the pharmacokinetics, safety and efficacy of dupilumab in a paediatric population with moderate-to-severe atopic dermatitis", P94, British Association of Dermatologists, Jul. 2017, 177 (Suppl. 1), pp. 25-77.

ClinicalTrials.gov Identifier: NTC02407756; Last Update posted Aug. 22, 2016, A Study to Determine the Safety and Tolerability of Dupilumab (REGN668/SAR231893) in Patients Aged >6 to <18 Years With Atopic Dermatitis (Eczema), 11 pages.

Dupixent (dupilumab) Injection, for Subcutaneous Use, Patient Information, Issued Mar. 2017, 34 pages.

Carr, Warner, "Topical Calcineurin Inhibitors for Atopic Dermatitis: Review and Treatment Recommendations", Pediatric Drugs, 2013, vol. 15, pp. 303-310.

Regeneron Pharmaceuticals (Oct. 16, 2017) "Regeneron and Sanofi Announce Positive Phase 2 Study Results for Dupilumab in Patients Active Moderate-to-severe Eosinophilic Esophagitis", Acquire Media, 4 Pages.

Siegfried et al., "Use of dupilimab in pediatric atopic dermatitis: Access, dosing, and implications for managing severe atopic dermatitis", Pediatric Dermatology, vol. 36, No. 1, Jan. 2019, pp. 172-176.

Ayars, Andrew G. et al., "Pharmacologic Therapies in Pulmonology and Allergy", 2016 Med Clin N Am 100(4): 851-868.

Russian Office Action and Search Report in Application 2019109062, with English translation, 32 pages.

Mulder, DJ et al., "Understanding eosinophilic esophagitis: the cellular and molecular mechanisms of an emerging disease", Mucosal Immunology, Mar. 2011, vol. 4, No. 2, pp. 139-147.

Yang, Eun-Seok et al., "Anti-IL-4 Receptor mAb Attenuates Allergic Airway Hyperresponsiveness (AHR) and Inflammation in Allergic Mice", J. Allergy Clin. Immunol. Poster 168, Abstracts S69, vol. 109, No. 1 (2002), 1 page.

Chen, Ching, et al., "Enhancement and destruction of antibody function by somatic mutation: unequal occurrence is controlled by V gene combinatorial associations", The EMBO Journal vol. 15, No. 12, pp. 2784-2794, 1995.

Kussie, Paul, et al., "A Single Engineered Amino Acid Substitution Changes Antibody Fine Specificity", Journal of Immunology:152, pp. 146-152, 1994.

Mashkovsky, M.D., Moscow, 2001 Medicines, 14th edition, v1:8-9 (Cited in RU Application 2019109062 received on Dec. 24, 2020).

\* cited by examiner

| Weekly EEsAI score | |
|---|---|
| Item | Score (total set to 100) |
| Frequency of trouble swallowing | |
| Never | 0 |
| 1–3 times/wk | 15 |
| 4–6 times/wk | 27 |
| Daily | 31 |
| Duration of trouble swallowing | |
| <=5 min | 0 |
| >5 min | 6 |
| Pain when swallowing | |
| No | 0 |
| Yes | 15 |
| VDQ score | |
| 0 | 0 |
| 0.1–2.5 | 12 |
| 2.6–5.0 | 19 |
| 5.1–7.5 | 21 |
| 7.6–10.0 | 23 |
| AMS score | |
| 0 | 0 |
| 0.1–2.5 | 0 |
| 2.6–5.0 | 0 |
| 5.1–7.5 | 9 |
| 7.6–10.0 | 25 |
| Total | 100 |

Figure 1

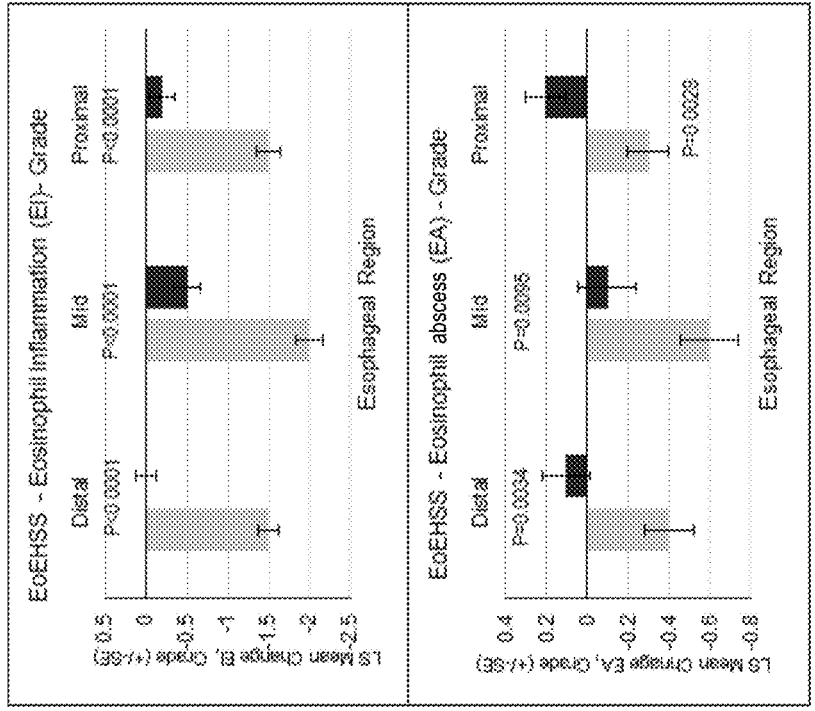
Figure 8C
Figure 8A
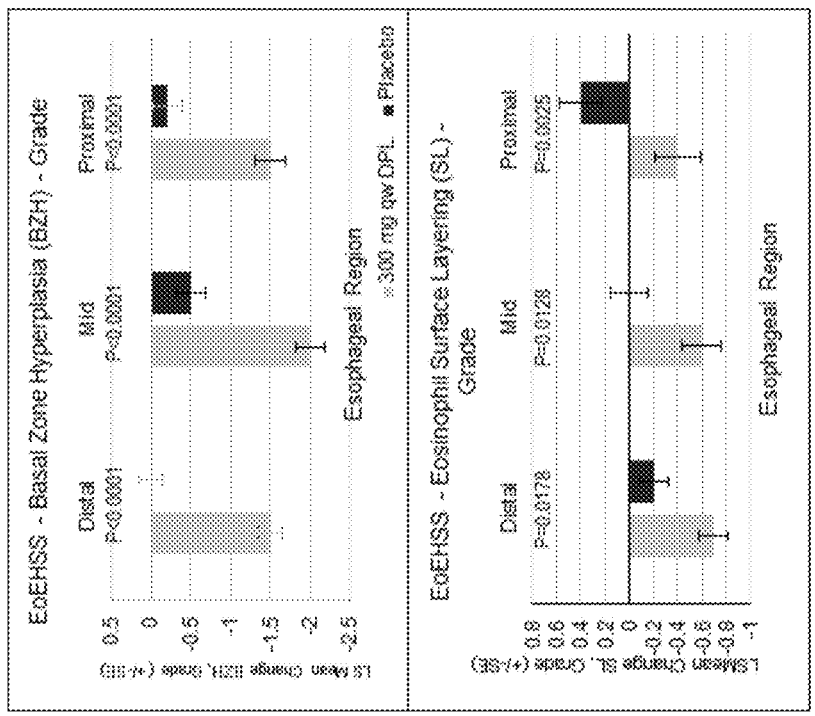
Figure 8D
Figure 8B
Figure 8

```
                        SEQUENCE LISTING

<160> NUMBER OF SEQ ID NOS: 11

<210> SEQ ID NO 1
<211> LENGTH: 124
<212> TYPE: PRT
<213> ORGANISM: Artificial Sequence
<220> FEATURE:
<223> OTHER INFORMATION: HCVR

<400> SEQUENCE: 1

Glu Val Gln Leu Val Glu Ser Gly Gly Gly Leu Glu Gln Pro Gly Gly
1               5                   10                  15

Ser Leu Arg Leu Ser Cys Ala Gly Ser Gly Phe Thr Phe Arg Asp Tyr
            20                  25                  30

Ala Met Thr Trp Val Arg Gln Ala Pro Gly Lys Gly Leu Glu Trp Val
        35                  40                  45

Ser Ser Ile Ser Gly Ser Gly Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Leu Ser Ile Thr Ile Arg Pro Arg Tyr Tyr Gly Leu
```

```
                    100             105             110

Asp Val Trp Gly Gln Gly Thr Thr Val Thr Val Ser
            115                 120

<210> SEQ ID NO 2
<211> LENGTH: 112
<212> TYPE: PRT
<213> ORGANISM: Artificial Sequence
<220> FEATURE:
<223> OTHER INFORMATION: LCVR

<400> SEQUENCE: 2

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Tyr Ser
            20                  25                  30

Ile Gly Tyr Asn Tyr Leu Asp Trp Tyr Leu Gln Lys Ser Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Phe Tyr Tyr Cys Met Gln Ala
                85                  90                  95

Leu Gln Thr Pro Tyr Thr Phe Gly Gln Gly Thr Lys Leu Glu Ile Lys
            100                 105                 110

<210> SEQ ID NO 3
<211> LENGTH: 8
<212> TYPE: PRT
<213> ORGANISM: Artificial Sequence
<220> FEATURE:
<223> OTHER INFORMATION: HCDR1

<400> SEQUENCE: 3

Gly Phe Thr Phe Arg Asp Tyr Ala
1               5

<210> SEQ ID NO 4
<211> LENGTH: 8
<212> TYPE: PRT
<213> ORGANISM: Artificial Sequence
<220> FEATURE:
<223> OTHER INFORMATION: HCDR2

<400> SEQUENCE: 4

Ile Ser Gly Ser Gly Gly Asn Thr
1               5

<210> SEQ ID NO 5
<211> LENGTH: 18
<212> TYPE: PRT
<213> ORGANISM: Artificial Sequence
<220> FEATURE:
<223> OTHER INFORMATION: HCDR3

<400> SEQUENCE: 5

Ala Lys Asp Arg Leu Ser Ile Thr Ile Arg Pro Arg Tyr Tyr Gly Leu
1               5                   10                  15

Asp Val

<210> SEQ ID NO 6
```

```
<211> LENGTH: 11
<212> TYPE: PRT
<213> ORGANISM: Artificial Sequence
<220> FEATURE:
<223> OTHER INFORMATION: LCDR1

<400> SEQUENCE: 6

Gln Ser Leu Leu Tyr Ser Ile Gly Tyr Asn Tyr
1               5                   10

<210> SEQ ID NO 7
<211> LENGTH: 3
<212> TYPE: PRT
<213> ORGANISM: Artificial Sequence
<220> FEATURE:
<223> OTHER INFORMATION: LCDR2

<400> SEQUENCE: 7

Leu Gly Ser
1

<210> SEQ ID NO 8
<211> LENGTH: 9
<212> TYPE: PRT
<213> ORGANISM: Artificial Sequence
<220> FEATURE:
<223> OTHER INFORMATION: LCDR3

<400> SEQUENCE: 8

Met Gln Ala Leu Gln Thr Pro Tyr Thr
1               5

<210> SEQ ID NO 9
<211> LENGTH: 451
<212> TYPE: PRT
<213> ORGANISM: Artificial Sequence
<220> FEATURE:
<223> OTHER INFORMATION: HC

<400> SEQUENCE: 9

Glu Val Gln Leu Val Glu Ser Gly Gly Gly Leu Glu Gln Pro Gly Gly
1               5                   10                  15

Ser Leu Arg Leu Ser Cys Ala Gly Ser Gly Phe Thr Phe Arg Asp Tyr
            20                  25                  30

Ala Met Thr Trp Val Arg Gln Ala Pro Gly Lys Gly Leu Glu Trp Val
        35                  40                  45

Ser Ser Ile Ser Gly Ser Gly Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Leu Ser Ile Thr Ile Arg Pro Arg Tyr Tyr Gly Leu
            100                 105                 110

Asp Val Trp Gly Gln Gly Thr Thr Val Thr Val Ser Ser Ala Ser Thr
        115                 120                 125

Lys Gly Pro Ser Val Phe Pro Leu Ala Pro Cys Ser Arg Ser Thr Ser
    130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175
```

Thr Phe Pro Ala Val Leu Gln Ser Ser Gly Leu Tyr Ser Leu Ser Ser
            180                 185                 190

Val Val Thr Val Pro Ser Ser Leu Gly Thr Lys Thr Tyr Thr Cys
        195                 200                 205

Asn Val Asp His Lys Pro Ser Asn Thr Lys Val Asp Lys Arg Val Glu
210                 215                 220

Ser Lys Tyr Gly Pro Pro Cys Pro Pro Cys Pro Ala Pro Glu Phe Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

Gln Glu Asp Pro Glu Val Gln Phe Asn Trp Tyr Val Asp Gly Val Glu
        275                 280                 285

Val His Asn Ala Lys Thr Lys Pro Arg Glu Glu Gln Phe Asn Ser Thr
290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Gln Glu Glu Met Thr Lys Asn Gln Val
        355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Arg Leu Thr
                405                 410                 415

Val Asp Lys Ser Arg Trp Gln Glu Gly Asn Val Phe Ser Cys Ser Val
            420                 425                 430

Met His Glu Ala Leu His Asn His Tyr Thr Gln Lys Ser Leu Ser Leu
        435                 440                 445

Ser Leu Gly
    450

<210> SEQ ID NO 10
<211> LENGTH: 219
<212> TYPE: PRT
<213> ORGANISM: Artificial Sequence
<220> FEATURE:
<223> OTHER INFORMATION: LC

<400> SEQUENCE: 10

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Tyr Ser
            20                  25                  30

Ile Gly Tyr Asn Tyr Leu Asp Trp Tyr Leu Gln Lys Ser Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

```
Ser Arg Val Glu Ala Glu Asp Val Gly Phe Tyr Tyr Cys Met Gln Ala
                85                  90                  95

Leu Gln Thr Pro Tyr Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 11
<211> LENGTH: 207
<212> TYPE: PRT
<213> ORGANISM: Artificial Sequence
<220> FEATURE:
<223> OTHER INFORMATION: hIL-4Ralpha

<400> SEQUENCE: 11

```
Met Lys Val Leu Gln Glu Pro Thr Cys Val Ser Asp Tyr Met Ser Ile
1               5                   10                  15

Ser Thr Cys Glu Trp Lys Met Asn Gly Pro Thr Asn Cys Ser Thr Glu
                20                  25                  30

Leu Arg Leu Leu Tyr Gln Leu Val Phe Leu Leu Ser Glu Ala His Thr
            35                  40                  45

Cys Ile Pro Glu Asn Asn Gly Gly Ala Gly Cys Val Cys His Leu Leu
        50                  55                  60

Met Asp Asp Val Val Ser Ala Asp Asn Tyr Thr Leu Asp Leu Trp Ala
65                  70                  75                  80

Gly Gln Gln Leu Leu Trp Lys Gly Ser Phe Lys Pro Ser Glu His Val
                85                  90                  95

Lys Pro Arg Ala Pro Gly Asn Leu Thr Val His Thr Asn Val Ser Asp
            100                 105                 110

Thr Leu Leu Leu Thr Trp Ser Asn Pro Tyr Pro Pro Asp Asn Tyr Leu
        115                 120                 125

Tyr Asn His Leu Thr Tyr Ala Val Asn Ile Trp Ser Glu Asn Asp Pro
    130                 135                 140

Ala Asp Phe Arg Ile Tyr Asn Val Thr Tyr Leu Glu Pro Ser Leu Arg
145                 150                 155                 160

Ile Ala Ala Ser Thr Leu Lys Ser Gly Ile Ser Tyr Arg Ala Arg Val
                165                 170                 175

Arg Ala Trp Ala Gln Cys Tyr Asn Thr Thr Trp Ser Glu Trp Ser Pro
            180                 185                 190

Ser Thr Lys Trp His Asn Ser Tyr Arg Glu Pro Phe Glu Gln His
        195                 200                 205
```

METHODS FOR TREATING ACTIVE EOSINOPHILIC ESOPHAGITIS

FIELD OF THE INVENTION

This application claims the benefit under 35 U.S.C. § 119(e) of U.S. provisional application Nos. 62/541,242 filed Aug. 4, 2017; 62/561,593, filed Sep. 21, 2017, and also claims priority to EP 18305252.1, filed Mar. 8, 2018. The disclosure of the aforementioned patent applications are herein incorporated by reference in their entireties.

SEQUENCE LISTING

The present application includes a Sequence Listing in electronic format as an ASCII txt file entitled "Sequence Listing", which was created on Aug. 3, 2018 and has a size of 11,072 bytes (10.8 KB).

The present invention relates to the use of interleukin-4/interleukin-13 pathway inhibitors to treat or prevent active eosinophilic esophagitis in a subject in need thereof.

BACKGROUND

Esophageal stricture (narrowing of the esophagus) results from injury to the esophageal lining and leads to, inter alia, difficulty in swallowing (dysphagia), regurgitation of food or liquid, heartburn and unintended weight loss. Treatment of esophageal stricture is very important as it reduces quality of life due to dysphagia, weight loss, and nutritional imbalance. Esophageal stricture may be caused due to chronic ulceration or chronic inflammation, as a complication due to chemotherapy, radiotherapy, esophageal cancer or endoscopic surgery, peptic ulcers or gastroesophageal reflux. Esophageal stricture is also caused by eosinophilic esophagitis.

Eosinophilic esophagitis (EoE) is an emerging, chronic, immune-/antigen-mediated disease characterized by esophageal dysfunction and eosinophil inflammation in the esophagus (Liacouras et al 2011, The Journal of Allergy and Clinical Immunology. 128: 3-20 e6; quiz 1-2; Weinbrand-Goichberg et al 2013, Immunologic Research. 56: 249-60; Zhang et al 2013, Digestive Diseases and Sciences 58: 1497-506). Adult patients with EoE have substantially impaired quality of life (QOL) due to dysphagia and the possible risk of food impaction (DeBrosse et al 2011, The Journal of Allergy and Clinical Immunology 128: 132-8; Falk et al 2014, Gastroenterology Clinics of North America 43: 231-42; Straumann 2008, Gastrointestinal Endoscopy Clinics of North America 18: 99-118; Straumann et al 2003, Gastroenterology 125: 1660-9). Patients with active disease or with moderate-to-severe EoE suffer from esophageal stricture leading to difficulty in swallowing, regurgitation of food or liquid and weight loss. Emergency endoscopy for prolonged food impactions is associated with a risk of severe esophageal injury. EoE is found to be associated with food allergy in many patients. Some patients may also have concomitant asthma or an atopic disease such as atopic dermatitis, or allergic rhinitis. The symptomatic burden of EoE, including food avoidance, eating modification behaviors, and social, emotional, financial, work and school, and sleep impacts, is also important and relevant to the EoE population and, if improved, may reflect a treatment benefit for EoE patients.

Current therapeutic approaches include chronic dietary elimination (including food allergen withdrawal), swallowed topical formulation corticosteroids (not approved for the treatment of EoE in the US), and esophageal dilation. Although swallowed topical corticosteroids have been reported in clinical trials to induce partial clinical responses and histologic remission, they are not uniformly effective and can be associated with fungal infections as well as disease recurrence after discontinuation. There are currently no approved drug therapies for EoE. Thus, an unmet need exists in the art for effective therapeutic approaches without adverse side effects that prevent or treat eosinophilic esophagitis. Esophageal stricture may be treated with proton pump inhibitors, which inhibit gastric acid secretion. Esophageal dilation by endoscopy is currently used to treat esophageal stricture and increase esophageal distensibility. However, it is a surgical procedure that is invasive and may lead to complications such as perforation and bleeding. Accordingly, there is an unmet need for safe and effective therapies that increase esophageal distensibility and treat esophageal stricture (e.g., in eosinophilic esophagitis).

BRIEF SUMMARY OF THE INVENTION

According to one aspect of the present invention, methods are provided for increasing the distensibility of the esophagus. The methods, according to this aspect, comprise: (a) selecting a patient with moderate-to-severe eosinophilic esophagitis (EoE), wherein the patient in need thereof has an attribute or is selected on the basis of a criterion selected from the group consisting of: (i) the patient has 15 eosinophils per high powered field (hpf) in the esophagus prior to or at the time of the treatment ("baseline"); (ii) the patient exhibits at least one episode of dysphagia per week; and (iii) the patient has a Straumann Dysphagia Instrument (SDI) score ≥2; and (b) administering a therapeutically effective amount of a pharmaceutical composition comprising an interleukin-4/interleukin-13 (IL-4/IL-13) pathway inhibitor to the patient in need thereof, thereby increasing esophageal distensibility, as measured by a functional lumen imaging probe (EndoFLIP®, Crospon, Ireland). In one embodiment, the patient has active EoE. In one embodiment, the patient is ≥18 years of age. In one embodiment, the patient has been treated previously with proton pump inhibitors (PPIs). In one embodiment, the patient has had at least one prior esophageal dilation. In one embodiment, the patient has a characteristic selected from the group consisting of: (1) prior treatment with at least one of PPIs, esophageal dilation, corticosteroids, allergen withdrawal and/or diet modification; (2) the patient is unresponsive or resistant to prior treatment with PPIs or esophageal dilation; (3) the patient has an Eosinophilic Esophagitis Severity and Activity Index (EEsAI) score ≥30, ≥40, or ≥50; (4) the patient suffers from EoE for at least 3 years; (5) the patient, prior to or at the time of administration of the IL-4/IL-13 pathway inhibitor, has or is diagnosed with a disease or disorder selected from the group consisting of food allergy, atopic dermatitis, asthma, allergic rhinitis and allergic conjunctivitis; and (6) the patient has an elevated level of a biomarker selected from the group consisting of eotaxin-3, periostin, serum IgE (total and allergen-specific), IL-13, IL-5, serum thymus and activation regulated chemokine (TARC), thymic stromal lymphopoietin (TSLP), serum eosinophilic cationic protein (ECP), and eosinophil-derived neurotoxin (EDN).

According to another aspect of the present invention, methods are provided for treating, preventing or ameliorating at least one symptom or indication of active eosinophilic esophagitis (EoE) in a subject. The methods, according to this aspect of the invention, comprise selecting a patient with moderate-to-severe EoE, and administering a therapeutically effective amount of a pharmaceutical composition comprising an interleukin-4/interleukin-13 (IL-4/IL-13) pathway inhibitor to the patient in need thereof. In certain embodiments, the patient in need thereof is selected on the basis of an attribute or criterion selected from the group consisting of: (1) the patient has ≥15 eosinophils per high powered field (hpf) in the esophagus prior to or at the time of the treatment ("baseline"); (2) prior treatment with at least one of high dose proton pump inhibitors (PPIs), esophageal dilation, corticosteroids, allergen withdrawal and/or diet modification; (3) the patient exhibits at least one episode of dysphagia per week; (4) the patient is unresponsive or resistant to prior treatment with high dose PPIs or esophageal dilation; (5) the patient has a Straumann Dysphagia Instrument (SDI) score ≥5; (6) the patient has an Eosinophilic Esophagitis Severity and Activity Index (EEsAI) score ≥30, ≥40, or ≥50; (7) the patient suffers from EoE for at least 3 years; (8) the patient, prior to or at the time of administration of the IL-4/IL-13 pathway inhibitor, has or is diagnosed with a disease or disorder selected from the group consisting of food allergy, atopic dermatitis, asthma, allergic rhinitis and allergic conjunctivitis; and (9) the patient has an elevated level of a biomarker selected from the group consisting of eotaxin-3, periostin, serum IgE (total and allergen-specific), IL-13, IL-5, serum thymus and activation regulated chemokine (TARC), thymic stromal lymphopoietin (TSLP), serum eosinophilic cationic protein (ECP), and eosinophil-derived neurotoxin (EDN).

In embodiments of the invention that specify the selection of "at least one . . . selected from the group consisting of" or simply "selected from the group consisting of", the use of the conjunction "and/or" between the final two items of the list following such language indicates that the items in the sequence are alternatives to one another, and that one (or more) of these items is/are selected. It does not mean that each of the items is necessarily selected. For example, for a method of increasing esophageal distensibility, wherein the patient has at least one characteristic selected from the group consisting of:
(1) prior treatment with at least one of PPIs, esophageal dilation, corticosteroids, allergen withdrawal, and/or diet modification;
(2) the patient is unresponsive or resistant to prior treatment with PPIs or esophageal dilation;
(3) the patient has an Eosinophilic Esophagitis Severity and Activity Index (EEsAI) score ≥30, ≥40, or ≥50;
(4) the patient has suffered from EoE for at least 3 years;
(5) the patient, prior to or at the time of administration of the IL-4/IL-13 pathway inhibitor, has or is diagnosed with a disease or disorder selected from the group consisting of food allergy, atopic dermatitis, asthma, allergic rhinitis, and/or allergic conjunctivitis; and/or
(6) the patient has an elevated level of at least one biomarker selected from the group consisting of eotaxin-3, periostin, serum IgE (total and allergen-specific), IL-13, IL-5, serum thymus and activation regulated chemokine (TARC), thymic stromal lymphopoietin (TSLP), serum eosinophilic cationic protein (ECP), and/or eosinophil-derived neurotoxin (EDN), what is meant is that the patient has at least characteristic (1) or characteristic (2) or characteristic (3) or characteristic (4) or characteristic (5) or characteristic (6). The patient can also, based on such language, have more than one of the six characteristics (for example, (1) and (2), or (4) and (5), or (1), (2), and (6), and so on). It is not, however, meant that the patient must have at least characteristic (1) and characteristic (2) and characteristic (3) and characteristic (4) and characteristic (5) and characteristic (6).

According to another aspect of the present invention, methods are provided for reducing dysphagia, the methods comprising selecting a patient with moderate-to-severe EoE wherein the patient (i) exhibits ≥1 episodes of dysphagia per week; (ii) has been treated previously with high-dose proton pump inhibitors (PPIs); and/or (iii) has had at least one prior esophageal dilation; and (b) administering a therapeutically effective amount of a pharmaceutical composition comprising an IL-4/IL-13 pathway inhibitor to the patient in need thereof.

According to another aspect of the present invention, methods are provided for improving a parameter, the methods comprising selecting a patient with moderate-to-severe EoE; and administering a therapeutically effective amount of a pharmaceutical composition comprising an IL-4/IL-13 pathway inhibitor, wherein the administration leads to an improvement in a parameter selected from the group consisting of: (a) reduction of at least 40% from baseline in dysphagia frequency and severity, as measured by Straumann Dysphagia Instrument (SDI) score; (b) reduction of 3 points from baseline in the SDI score; (c) reduction of more than 85% from baseline in peak intraepithelial eosinophil count in proximal, mid and/or distal regions of the esophagus; (d) increase of at least 10% from baseline in esophageal distensibility, as measured by impedance planimetry; (e) decrease of more than 50% from baseline in severity and extent of disease, as measured by EoE Histology Scoring System (HSS) score; and (f) reduction of more than 30% from baseline in dysphagia, as measured by Eosinophilic Esophagitis Severity and Activity Index (EEsAI) score.

According to another aspect of the present invention, methods are provided for reducing the eosinophilic infiltration of esophagus in a patient in need thereof. In certain embodiments, methods are provided for reducing inflammation in the esophagus. The methods comprise administering a therapeutically effective amount of a pharmaceutical composition comprising an IL-4/IL-13 pathway inhibitor. In certain embodiments, the eosinophilic infiltration of the esophagus is represented by greater than or equal to about 15 eosinophils per high powered field in the esophagus of the subject in need thereof. In certain embodiments, the number of eosinophils is reduced ≥85% following administration of the IL-4/IL-13 pathway inhibitor. In certain embodiments, the inflammation (e.g., mucosal inflammation) is identified by endoscopy and features such as esophageal edema, rings, exudates, furrows and strictures (EREFS). In certain embodiments, administration of the IL-4/IL-13 pathway inhibitor leads to reduction in the EREFS score to less than 8, less than 7, less than 6, less than 5, less than 4, less than 3, or less than 2 (disclosed elsewhere herein).

According to another aspect of the present invention, methods are provided for reducing the level of an EoE-associated biomarker in a subject. In certain embodiments, the EoE-associated biomarker is selected from the group consisting of, e.g., circulating or esophagus eosinophils, eotaxin-3, periostin, serum IgE (total and allergen-specific), IL-13, IL-5, serum thymus and activation regulated chemokine (TARC; CCL17), thymic stromal lymphopoietin (TSLP), serum eosinophilic cationic protein (ECP), and eosinophil-derived neurotoxin (EDN). The methods comprise administering a therapeutically effective amount of a pharmaceutical composition comprising an IL-4/IL-13 pathway inhibitor.

In certain embodiments, the IL-4/IL-13 pathway inhibitor is administered in combination with a second therapeutic agent or therapy.

In certain embodiments, the subject in need thereof has a concurrent disease or disorder selected from the group consisting of food allergy, atopic dermatitis, asthma, allergic rhinitis, allergic conjunctivitis and inherited connective tissue disorders.

Exemplary IL-4/IL-13 pathway inhibitors that can be used in the context of the methods of the present invention include, but are not limited to, an anti-IL-4 antibody, an anti-IL-13 antibody, a bispecific anti-IL-4/IL-13 antibody and an IL-4 receptor (IL-4R) inhibitor. In one embodiment, the IL-4/IL-13 pathway inhibitor is an IL-4R inhibitor (such as an anti-IL-4R antibody).

Exemplary IL-4R inhibitors that can be used in the context of the methods of the present invention include, e.g., small molecule chemical inhibitors of IL-4R or its ligands (IL-4 and/or IL-13), or biological agents that target IL-4R or its ligands. According to certain embodiments, the IL-4R inhibitor is an antibody or antigen-binding protein that binds the IL-4Rα chain and blocks signaling by IL-4, IL-13, or both IL-4 and IL-13. In certain embodiments, the anti-IL-4R antibody or antigen-binding protein comprises the heavy chain complementarity determining regions (HCDRs) of a heavy chain variable region (HCVR) comprising the amino acid sequence of SEQ ID NO: 1 and the light chain CDRs of a light chain variable region (LCVR) comprising the amino acid sequence of SEQ ID NO: 2. One such type of antigen-binding protein that can be used in the context of the methods of the present invention is an anti-IL-4Rα antibody such as dupilumab.

In certain embodiments, the present invention provides use of an IL-4/IL-13 pathway inhibitor in the manufacture of a medicament to treat or inhibit or prevent active eosinophilic esophagitis in a subject, including humans.

In certain embodiments, the present invention provides use of an antibody or antigen-binding fragment thereof that binds to IL-4R in the manufacture of a medicament to treat or inhibit or prevent active eosinophilic esophagitis in a subject, including humans.

In certain embodiments, the present invention provides use of an IL-4/IL-13 pathway inhibitor in the manufacture of a medicament to increase esophageal distensibility in a subject, including humans. In one embodiment, the subject has active EoE. In one embodiment, the subject has moderate-to-severe EoE.

In certain embodiments, the present invention provides use of an antibody or antigen-binding fragment thereof that binds to IL-4R in the manufacture of a medicament to increase esophageal distensibility in a subject, including humans. In one embodiment, the subject has active EoE. In one embodiment, the subject has moderate-to-severe EoE Other embodiments of the present invention will become apparent from a review of the ensuing detailed description.

BRIEF DESCRIPTION OF THE FIGURES

FIG. 1 lists the components comprising the weekly Eosinophilic Esophagitis Severity and Activity Index (EEsAI) score.

FIG. 8 is made up of FIGS. 8A, 8B, 8C, and 8D. FIG. 8A shows mean change from baseline in EoE HSS grade scores for basal zone hyperplasia; FIG. 8B shows mean change from baseline in EoE HSS grade scores for eosinophil surface layering; FIG. 8C shows mean change from baseline in EoE HSS grade scores for eosinophil inflammation; and FIG. 8D shows mean change from baseline in EoE HSS grade scores for eosinophil abscess in proximal, mid and distal regions of the esophagus sampled at week 12 from patients administered once-a-week (qw) 300 mg dupilumab vs placebo.

FIG. 9A shows mean change from baseline in EoE HSS stage scores for basal zone hyperplasia; FIG. 9B shows mean change from baseline in EoE HSS stage scores for eosinophil abscess; FIG. 9C shows mean change from baseline in EoE HSS stage scores for eosinophil inflammation; and FIG. 9D shows mean change from baseline in EoE HSS stage scores for eosinophil surface layering in proximal, mid and distal regions of the esophagus sampled at week 12 from patients administered once-a-week (qw) 300 mg dupilumab vs placebo.

FIG. 10A shows mean change from baseline in EoE HSS grade scores for dilated intercellular spaces; FIG. 10B shows mean change from baseline in EoE HSS grade scores for surface alteration and FIG. 10C shows mean change from baseline in EoE HSS grade scores for apoptotic epithelial cells in proximal, mid and distal regions of the esophagus sampled at week 12 from patients administered once-a-week (qw) 300 mg dupilumab vs placebo.

FIG. 11A shows mean change from baseline in EoE HSS stage scores for dilated intercellular spaces; FIG. 11B shows mean change from baseline in EoE HSS stage scores for surface alteration and FIG. 11C shows mean change from baseline in EoE HSS stage scores for apoptotic epithelial cells in proximal, mid and distal regions of the esophagus sampled at week 12 from patients administered once-a-week (qw) 300 mg dupilumab vs placebo.

DETAILED DESCRIPTION

Figure 2:
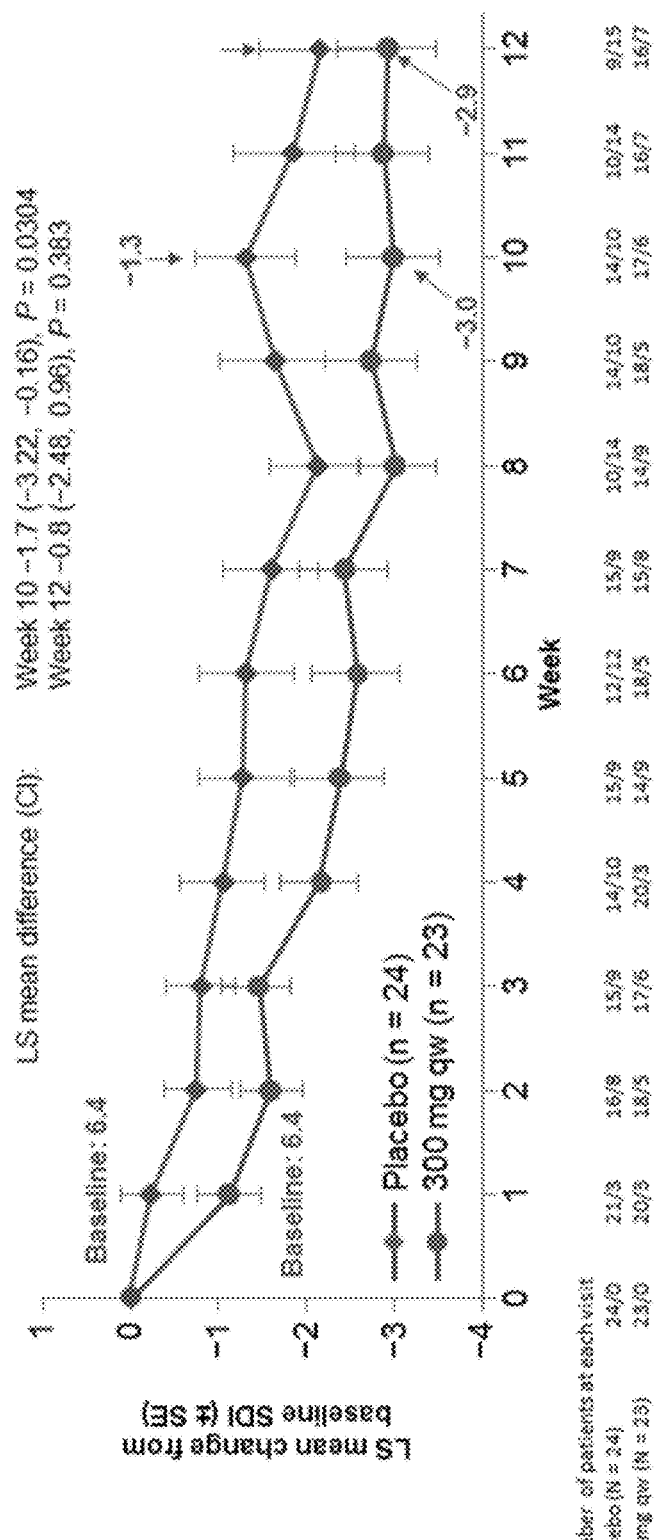
FIG. 2 shows mean change from baseline in Straumann Dysphagia Instrument (SDI) scores during the 12-week treatment period in patients administered once-a-week (qw) 300 mg dupilumab vs placebo.

Before the present invention is described, it is to be understood that this invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

Although any methods and materials similar or equivalent to those described herein can be used in the practice of the present invention, the preferred methods and materials are now described. All publications mentioned herein are incorporated herein by reference to describe in their entirety.

Methods for Treating, Preventing or Ameliorating Eosinophilic Esophagitis

The present invention includes methods for treating, preventing, or ameliorating at least one symptom or indication of active eosinophilic esophagitis (EoE) in a subject. The methods according to this aspect of the invention comprise administering a therapeutically effective amount of a pharmaceutical composition comprising an IL-4/IL-13 pathway inhibitor to the subject in need thereof. As used herein, the terms "treat", "treating", or the like, mean to alleviate symptoms, eliminate the causation of symptoms either on a temporary or permanent basis, or to prevent or slow the appearance of symptoms of eosinophilic inflammation in the esophagus. In certain embodiments, the present methods are useful for treating or ameliorating at least one symptom or indication of EoE including, but not limited to, eosinophilic infiltration of the esophagus, thickening of the esophageal wall, inflammation in the esophagus, appearance of trachea-like rings or ridges in the esophagus, chest and abdominal pain, food refusal, vomiting, dysphagia and food impaction.

"Eosinophilic Esophagitis" (EoE), as used herein, means an inflammatory disease characterized by abnormal eosinophilic inflammation within the esophagus and esophageal dysfunction. The primary symptoms of EoE include, but are not limited to, chest and abdominal pain, dysphagia, heartburn, food refusal, vomiting and food impaction. The clinicopathology of EoE is characterized by presence of ridges or trachea-like rings in the esophageal wall and eosinophilic infiltration in the esophageal mucosa. EoE is diagnosed by endoscopy of the esophagus followed by microscopic and biochemical analysis of the esophageal mucosal lining. EoE may be classified as allergic or non-allergic depending upon the status of the subject. The present invention includes methods to treat both allergic and non-allergic forms of EoE.

As used herein, the term "active EoE" refers to the EoE disease in a patient wherein the patient has ≥15 eosinophils/high powered field (hpf) in an esophageal biopsy even after 8 weeks of treatment with proton pump inhibitors (PPIs). The term also refers to the EoE disease in patients that exhibit frequent dysphagia, e.g., the patient has 2, 3, 4, 5, or more episodes of dysphagia per week. The term "active EoE" includes mild EoE as well as moderate-to-severe EoE. The term "moderate-to-severe" refers to EoE disease in patients that in addition to eosinophilia (e.g., ≥15 eosinophils/hpf in the esophageal mucosa) and frequent episodes of dysphagia, have SDI score ≥2 and/or EEsAI score ≥30, have duration of EoE for at least 2 years, and/or are non-responsive or resistant to prior therapy (including PPIs or esophageal dilation).

As used herein, the expression "a subject in need thereof" means a human or non-human mammal that exhibits one or more symptoms or indications of eosinophilic esophagitis, and/or who has been diagnosed with eosinophilic esophagitis (EoE). Throughout the present disclosure, the term "subject" is used interchangeably with the term "patient". The term "a subject in need thereof" may also include, e.g., patients who, prior to treatment, exhibit (or have exhibited) one or more indications of EoE such as, e.g., esophageal overexpression of pro-inflammatory mediators such as mast cells, eosinophilic infiltration of the esophagus, thickening of the esophageal wall, dysphagia, food impaction and chest and abdominal pain and/or an elevated level of a EoE-associated biomarker. The term specifically includes subjects who show the presence of ≥15 eosinophils per high power field in the esophagus. In certain embodiments, the term also includes subjects with elevated peripheral eosinophil counts (e.g., ≥100, ≥150, ≥200, or ≥300 cells/µl) or elevated serum IgE (>150 kU/L).

In certain embodiments, the present methods may be used to treat patients who exhibit pathology and symptoms that are observed in subjects with chronic esophagitis including in gastroesophageal reflux disease (GERD). In certain embodiments, the term "a subject in need thereof" includes subjects that are non-responsive to or resistant to anti-GERD therapy. For example, the present methods may be used to treat subjects that are resistant to proton pump inhibitors (PPI).

In the context of the present invention, "a subject in need thereof" may include a subset of population that is more susceptible to EoE or may show an elevated level of an EoE-associated biomarker. For example, "a subject in need thereof" may include a subject suffering from an atopic disease or disorder such as food allergy, atopic dermatitis, asthma, allergic rhinitis and allergic conjunctivitis. In certain embodiments, the term "a subject in need thereof" includes a patient who, prior to or at the time of administration of the IL-4/IL-13 pathway inhibitor, has or is diagnosed with a disease or disorder selected from the group consisting of food allergy, atopic dermatitis, asthma, allergic rhinitis and allergic conjunctivitis. In certain embodiments, the term "a subject in need thereof" may include patients with inherited connective tissue disorders. Such a subject population may show an elevated level of an EoE-associated biomarker such as, e.g., IgE, eotaxin-3, periostin, IL-5, or IL-13.

In certain embodiments, "a subject in need thereof" includes a patient susceptible to an allergen. For example, "a subject in need thereof" includes a patient who may exhibit one of the following characteristics: (a) is prone to allergic reactions or responses when exposed to one or more allergens; (b) has previously exhibited an allergic response or reaction to one or more allergens; (c) has a known history of allergies; and/or (d) exhibits a sign or symptom of an allergic response or anaphylaxis. In certain embodiments, the patient is allergic to an allergen associated with EoE or that renders the subject susceptible and/or prone to developing EoE.

The term "allergen," as used herein, includes any substance, chemical, particle or composition that is capable of stimulating an allergic response in a susceptible individual. Allergens may be contained within or derived from a food item such as, e.g., dairy products (e.g., cow's milk), egg, wheat, soy, corn, rye, fish, shellfish, peanuts and tree nuts. Alternatively, an allergen may be contained within or derived from a non-food item such as, e.g., dust (e.g., containing dust mite), pollen, insect venom (e.g., venom of bees, wasps, mosquitoes, etc.), mold, animal dander, latex, medication, drugs, ragweed, grass and birch.

In certain embodiments, the term "a subject in need thereof" includes a subset of population that exhibits an allergic reaction to a food allergen. For example, "a subject in need thereof" may include a subject who has an allergy to an allergen contained in a food item including, but not limited to, a dairy product, egg, wheat, soy, corn, rye, fish, shellfish, peanut, a tree nut, beef, chicken, oat, barley, pork, green beans, and fruits such as apple and pineapple.

In certain embodiments, the term includes a subject allergic to a non-food allergen such as allergens derived from dust, mold, insects, plants including pollen, and pets such as cats and dogs. Examples of non-food allergens (also known as environmental allergens or aeroallergens) include, but are not limited to, house dust mite allergens, pollen allergens, animal dander allergens, insect venom, grass allergens, and latex.

As used herein, the phrases "allergic response," "allergic reaction," "allergic symptom," and the like, include one or more signs or symptoms selected from the group consisting of urticaria (e.g., hives), angioedema, rhinitis, asthma, vomiting, sneezing, runny nose, sinus inflammation, watery eyes, wheezing, bronchospasm, reduced peak expiratory flow (PEF), gastrointestinal distress, flushing, swollen lips, swollen tongue, reduced blood pressure, anaphylaxis, and organ dysfunction/failure. An "allergic response," "allergic reaction," "allergic symptom," etc., also includes immunological responses and reactions such as, e.g., increased IgE production, increased allergen-specific immunoglobulin production and/or eosinophilia.

In some embodiments, the methods herein are for the treatment of adults, adolescents or children. An adult is ≥18 years of age, an adolescent is ≥12 and ≤18 years of age and children are ≤12 years of age. In some embodiments, the methods herein may be used to treat EoE in children who are ≤3 years old. In one embodiment, an inhibitor of the IL-4/IL-13 pathway is used to treat moderate-to severe EoE in subjects that are not adequately controlled with standard-of-care treatment (e.g., oral corticosteroids, dilation, etc.) The subject can be an adult, an adolescent or a child.

The present invention also includes methods to increase esophageal distensibility. The methods according to this aspect of the invention comprise administering to the patient in need thereof one or more doses of a pharmaceutical composition comprising an IL-4/IL-13 pathway inhibitor, thereby increasing the distensibility of the esophagus in the patient.

The present invention also includes methods for reducing eosinophilic infiltration. The methods according to this aspect of the invention comprise administering to the patient in need thereof one or more doses of a pharmaceutical composition comprising an IL-4/IL-13 pathway inhibitor to reduce or eliminate the number of eosinophils, e.g., in the esophageal mucosa.

As used herein, "eosinophilic infiltration" refers to the presence of eosinophils in an organ or tissue including blood, esophagus, stomach, duodenum, and ileum of a subject. In the context of the invention, the term "eosinophilic infiltration" refers to presence of eosinophils in the mucosal lining of a region of the gastro-intestinal tract including, but not limited to, esophagus and stomach. Eosinophilic infiltration is analyzed, for example, in an esophageal tissue biopsy of a subject suffering from EoE. According to particular embodiments, "eosinophilic infiltration" refers to the presence of ≥15 eosinophils per high power field in the esophagus. The term "high power field" refers to a standard total magnification of 400× by a microscope used to view eosinophils in a tissue, e.g., from the esophagus of a subject. In certain embodiments, "eosinophilic infiltration" includes infiltration into a tissue by leucocytes, for example, lymphocytes, neutrophils and mast cells. The leucocyte infiltration into, e.g., esophageal tissue can be detected by cell surface markers such as eosinophil-specific markers (e.g., $CD11c^{Low/Neg}$, $SiglecF^+$, $F4/80^+$, $EMR1^+$, $Siglec\,8^+$, and $MBP2^+$), macrophage-specific markers (e.g., $CD11b^+$, $F4/80^+$, $CD14^+$, $EMR1^+$, and $CD68^+$), neutrophil-specific markers (e.g., $CD11b^+$, $Ly6G^+$, $Ly6C^+$, $CD11b^+$, and $CD66b^+$), and T-cell-specific markers (e.g., $CD3^+$ $CD4^+$ $CD8^+$).

As used herein, a reduction in esophagus eosinophils means that the number of eosinophils and other leucocytes measured in the esophagus of a subject with EoE and who has been treated with an IL-4/IL-13 pathway inhibitor, is at least 5%, 10%, 20%, 50%, 70%, 80%, or 90% lower than the esophagus eosinophils measured in the same or an equivalent subject that has not been treated with the IL-4/IL-13 pathway inhibitor. In certain embodiments, reducing eosinophilic infiltration means detecting less than 15 eosinophils per high power field, more preferably less than 10 eosinophils, less than 9 eosinophils, less than 8 eosinophils, less than 7 eosinophils, less than 6 eosinophils, or less than 5 eosinophils per high power field in a biopsy of the esophageal mucosa. In certain embodiments, a reduction in esophagus eosinophils means that no eosinophils are detected in the esophageal mucosa of a subject.

The present invention includes methods for treating, preventing or reducing the severity of eosinophilic esophagitis comprising administering a therapeutically effective amount of a pharmaceutical composition comprising an IL-4/IL-13 pathway inhibitor to a subject in need thereof, wherein the pharmaceutical composition is administered to the subject in multiple doses, e.g., as part of a specific therapeutic dosing regimen. For example, the therapeutic dosing regimen may comprise administering multiple doses of the pharmaceutical composition to the subject at a frequency of about once a day, once every two days, once every three days, once every four days, once every five days, once every six days, once a week, once every two weeks, once every three weeks, once every four weeks, once a month, once every two months, once every three months, once every four months, or less frequently.

The methods of the present invention, according to certain embodiments, comprise administering to a subject a therapeutically effective amount of a pharmaceutical composition comprising an IL-4/IL-13 pathway inhibitor in combination with a second therapeutic agent. The second therapeutic agent may be an agent selected from the group consisting of, e.g., an IL-1beta inhibitor, an IL-5 inhibitor, an IL-9 inhibitor, an IL-13 inhibitor, an IL-17 inhibitor, an IL-25 inhibitor, a TNFalpha inhibitor, an eotaxin-3 inhibitor, an IgE inhibitor, a prostaglandin D2 inhibitor, an immunosuppressant, a topical corticosteroid, an oral corticosteroid (e.g., budesonide), a systemic corticosteroid, an inhaled corticosteroid, a glucocorticoid, a proton pump inhibitor, a decongestant, an antihistamine, and a non-steroidal anti-inflammatory drug (NSAID). In certain embodiments, the IL-4/IL-13 pathway inhibitor of the invention may be administered in combination with therapy including esophagus dilation, allergen removal and diet management. As used herein, the phrase "in combination with" means that the pharmaceutical composition comprising an IL-4/IL-13 pathway inhibitor is administered to the subject at the same time as, just before, or just after administration of the second therapeutic agent. In certain embodiments, the second therapeutic agent is administered as a co-formulation with the IL-4/IL-13 pathway inhibitor. In a related embodiment, the present invention includes methods comprising administering a therapeutically effective amount of a pharmaceutical composition comprising an IL-4/IL-13 pathway inhibitor to a subject who is on a background anti-allergy therapeutic regimen. The background anti-allergy therapeutic regimen may comprise a course of administration of, e.g., steroids, antihistamines, decongestants, anti-IgE agents, etc. The IL-4/IL-13 pathway inhibitor (e.g., an anti-IL-4R antibody) may be added on top of the background anti-allergy therapeutic regimen. In some embodiments, the IL-4/IL-13 pathway inhibitor is added as part of a "background step-down" scheme, wherein the background anti-allergy therapy is gradually withdrawn from the subject over time (e.g., in a stepwise fashion) while the IL-4/IL-13 pathway inhibitor is administered the subject at a constant dose, or at an increasing dose, or at a decreasing dose, over time. In certain embodiments, the IL-4/IL-13 pathway inhibitor is administered as a monotherapy.

Eosinophilic Esophagitis-associated Biomarkers

The present invention also includes methods involving the use, quantification, and analysis of EoE-associated biomarkers. As used herein, the term "EoE-associated biomarker" means any biological response, cell type, parameter, protein, polypeptide, enzyme, enzyme activity, metabolite, nucleic acid, carbohydrate, or other biomolecule which is present or detectable in an EoE patient at a level or amount that is different from (e.g., greater than or less than) the level or amount of the marker present or detectable in a non-EoE patient. Exemplary EoE-associated biomarkers include, but are not limited to, e.g., esophagus eosinophils, eotaxin-3 (CCL26), periostin, serum IgE (total and allergen-specific), serum IgG (total and allergen-specific), IL-13, IL-5, serum thymus and activation regulated chemokine (TARC; CCL17), thymic stromal lymphopoietin (TSLP), serum eosinophilic cationic protein (ECP), calpain 14, filaggrin (FLG), signal transducer and activator of transcription 6 (STAT6), interleukin 4 receptor (IL-4R), and eosinophil-derived neurotoxin (EDN). The term "EoE-associated biomarker" also includes a gene or gene probe known in the art that is differentially expressed in a subject with EoE as compared to a subject without EoE. For example, genes which are significantly up-regulated in a subject with EoE include, but are not limited to, T-helper 2 (Th2)-associated chemokines such as CCL8, CCL23 and CCL26, periostin, cadherin-like-26, and TNFα-induced protein 6 (Blanchard et al 2006, J. Clin. Invest. 116: 536-547). Alternatively, "EoE-associated biomarker" also includes genes that are down regulated due to EoE such as terminal differentiation proteins (e.g., filaggrin) (Blanchard et al 2006, J. Clin. Invest. 116: 536-547). Certain embodiments of the invention relate to use of these biomarkers for monitoring disease reversal with the administration of the IL-4/IL-13 pathway inhibitor. Methods for detecting and/or quantifying such EoE-associated biomarkers are known in the art; kits for measuring such EoE-associated biomarkers are available from various commercial sources; and various commercial diagnostic laboratories offer services which provide measurements of such biomarkers as well.

According to certain aspects of the invention, methods for treating EoE are provided which comprise: (a) selecting a subject who exhibits a level of at least one EoE-associated biomarker prior to or at the time of treatment which signifies the disease state; and (b) administering to the subject a pharmaceutical composition comprising a therapeutically effective amount of an IL-4/IL-13 pathway inhibitor. In certain embodiments of this aspect of the invention, the subject is selected on the basis of an elevated level of IgE or eotaxin-3.

According to other aspects of the invention, methods for treating EoE are provided which comprise administering to a subject a pharmaceutical composition comprising a therapeutically effective amount of an IL-4/IL-13 pathway inhibitor, wherein administration of the pharmaceutical composition to the subject results in a decrease in at least one EoE-associated biomarker (e.g., esophagus eosinophils, eotaxin-3, IgE, etc.) at a time after administration of the pharmaceutical composition, as compared to the level of the biomarker in the subject prior to the administration.

As will be appreciated by a person of ordinary skill in the art, an increase or decrease in an EoE-associated biomarker can be determined by comparing (i) the level of the biomarker measured in a subject at a defined time point after administration of the pharmaceutical composition comprising an IL-4/IL-13 pathway inhibitor to (ii) the level of the biomarker measured in the patient prior to the administration of the pharmaceutical composition comprising an IL-4/IL-13 pathway inhibitor (i.e., the "baseline measurement"). The defined time point at which the biomarker is measured can be, e.g., at about 4 hours, 8 hours, 12 hours, 1 day, 2 days, 3 days, 4 days, 5 days, 6 days, 7 days, 8 days, 9 days, 10 days, 15 days, 20 days, 35 days, 40 days, 50 days, 55 days, 60 days, 65 days, 70 days, 75 days, 80 days, 85 days, or more after administration of the of the pharmaceutical composition comprising an IL-4/IL-13 pathway inhibitor.

According to certain embodiments of the present invention, a subject may exhibit a decrease in the level of one or more of IgE and/or eotaxin-3 following administration of a pharmaceutical composition comprising an IL-4/IL-13 pathway inhibitor (e.g., an anti-IL-4R antibody). For example, at about day 1, day 4, day 8, day 15, day 22, day 25, day 29, day 36, day 43, day 50, day 57, day 64, day 71 or day 85, following administration of a first, second, third or fourth dose of a pharmaceutical composition comprising about 75 mg to about 600 mg of an anti-IL-4R antibody (e.g., dupilumab), the subject, according to the present invention, may exhibit a decrease in eotaxin-3 of about 1%, 2%, 5%, 10%, 15%, 20%, 25%, 30%, 35%, 40%, 45%, 50%, 55%, 60%, 65%, 70%, 75%, 80%, 85%, 90%, 95% or more from baseline (wherein "baseline" is defined as the level of eotaxin-3 in the subject just prior to the first administration). Similarly, at about day 1, day 4, day 8, day 15, day 22, day 25, day 29, day 36, day 43, day 50, day 57, day 64, day 71 or day 85, following administration of a first, second, third or fourth dose of a pharmaceutical composition comprising about 75 mg to about 600 mg of an anti-IL-4R antibody (e.g., dupilumab), the subject, according to the present invention, may exhibit a decrease in IgE of about 1%, 2%, 5%, 10%, 15%, 20%, 25%, 30%, 35%, 40%, 45%, 50%, 55%, 60%, 65%, 70%, 75%, 80%, 85%, 90%, 95% or more from baseline (wherein "baseline" is defined as the level of IgE in the subject just prior to the first administration).

The present invention also includes methods for determining whether a subject is a suitable subject for whom administration of a pharmaceutical composition comprising an IL-4/IL-13 pathway antagonist would be beneficial. For example, if an individual, prior to receiving a pharmaceutical composition comprising an IL-4/IL-13 pathway antagonist, exhibits a level of an EoE-associated biomarker that signifies the disease state, the individual is therefore identified as a suitable patient for whom administration of a pharmaceutical composition of the invention (a composition comprising an anti-IL-4R antibody) would be beneficial. In related embodiments, the present invention includes methods for treating suitable subjects, wherein a suitable subject may be more susceptible to EoE, for example, due to food allergy, or an atopic disease. For example, the present invention includes methods comprising administering an IL-4/IL-13 pathway antagonist to subjects who have food allergy, atopic dermatitis, asthma, allergic rhinitis or allergic conjunctivitis. In another example, the present invention includes methods comprising administering an IL-4/IL-13 pathway antagonist to subjects who have, Mendelian-inherited connective tissue disorders, e.g., Marfan syndrome, Loeys-Dietz syndrome, hypermobile Ehlers Danlos syndrome (EDS) or joint hypermobility syndrome (JHS). Such subject populations may have an elevated level of an EoE-associated biomarker.

According to certain exemplary embodiments, an individual may be identified as a good candidate for anti-IL-4/IL-13 therapy if the individual exhibits one or more of the following: (i) an eotaxin-3 level greater than about 30 pg/ml, greater than about 40 pg/ml, greater than about 50 pg/ml, greater than about 100 pg/ml, greater than about 1500 pg/ml, greater than about 200 pg/ml, greater than about 250 pg/ml, greater than about 300 pg/ml, greater than about 350 pg/ml, greater than about 400 pg/ml, greater than about 450 pg/ml, or greater than about 500 pg/ml; or (ii) a serum IgE level greater than about 114 kU/L, greater than about 150 kU/L, greater than about 500 kU/L, greater than about 1000 kU/L, greater than about 1500 kU/L, greater than about 2000 kU/L, greater than about 2500 kU/L, greater than about 3000 kU/L, greater than about 3500 kU/L, greater than about 4000 kU/L, greater than about 4500 kU/L, or greater than about 5000 kU/L; or (iii) 15 eosinophils per high power field in the esophagus of the subject. Additional criteria, such as other clinical indicators of EoE (e.g., dysphagia, thickening of the esophageal wall, and food allergy indicative of EoE), may be used in combination with any of the foregoing EoE-associated biomarkers to identify an individual as a suitable candidate for anti-IL-4/IL-13 therapy as described elsewhere herein.

Eosinophilic Esophagitis-related Parameters

The present invention includes methods for improving one or more eosinophilic esophagitis (EoE)-related parameters in a subject in need thereof, wherein the methods comprise administering a pharmaceutical composition comprising an IL-4/IL-13 pathway inhibitor to the subject.

Examples of "EoE-related parameters" include: (a) Straumann Dysphagia Instrument (SDI); (b) Eosinophilic Esophagitis Activity Index (EEsAI); (c) Eosinophilic Esophagitis Edema Rings Exudates Furrows and Strictures (EoE-EREFS); (d) Eosinophilic Esophagitis Histological Scoring System (EoE-HSS) (e) Esophageal intraepithelial eosinophils; and (f) Esophageal distensibility. An "improvement in an EoE-related parameter" means a decrease from baseline of one or more of SDI, EEsAI, EoE-EREFS, EoE-HSS, or esophageal intraepithelial eosinophils. An improvement in esophageal distensibility means an increase from the baseline. As used herein, the term "baseline," with regard to an EoE-related parameter, means the numerical value of the EoE-related parameter for a subject prior to or at the time of administration of a pharmaceutical composition of the present invention.

To determine whether an EoE-related parameter has "improved," the parameter is quantified at baseline and at one or more time-points after administration of the pharmaceutical composition of the present invention. For example, an EoE-related parameter may be measured at day 1, day 2, day 3, day 4, day 5, day 6, day 7, day 8, day 9, day 10, day 11, day 12, day 14, day 15, day 22, day 25, day 29, day 36, day 43, day 50, day 57, day 64, day 71, day 85; or at the end of week 1, week 2, week 3, week 4, week 5, week 6, week 7, week 8, week 9, week 10, week 11, week 12, week 13, week 14, week 15, week 16, week 17, week 18, week 19, week 20, week 21, week 22, week 23, week 24, or longer, after the initial treatment with a pharmaceutical composition of the present invention. The difference between the value of the parameter at a particular time point following initiation of treatment and the value of the parameter at baseline is used to establish whether there has been an "improvement" (e.g., a decrease) in the EoE-related parameter.

Straumann Dysphagia Instrument (SDI). The SDI is a non-validated patient reported outcome (PRO) that has been used in clinical studies to determine the frequency and intensity of dysphagia (Straumann 2010). The SDI has a 1-week recall period. Frequency of dysphagia events is graded on a 5-point scale: 0=none, 1=once per week, 2=several times per week, 3=once per day, and 4=several times per day, and intensity of dysphagia events is graded on a 6-point scale: 0=swallowing unrestricted, 1=slight sensation of resistance, 2=slight retching with delayed passage, 3=short period of obstruction necessitating intervention (e.g., drinking, breathing), 4=longer-lasting period obstruction only removable by vomiting, and 5=long-lasting complete obstruction requiring endoscopic intervention. The total SDI score ranges from 0 to 9. According to certain embodiments of the present invention, administration of an IL-4/IL-13 pathway inhibitor to a patient results in a decrease in SDI score of 3 points from the baseline. For example, the present invention includes therapeutic methods that result in a decrease from baseline in SDI score of decrease of 1, 2, 3, 4, 5, 6 or more points from baseline in SDI. In certain exemplary embodiments, administration of an IL-4/IL-13 pathway inhibitor to a patient results in a decrease at least about 10%, 15%, 20%, 25%, 30%, 35%, 40%, 45%, 50%, or more at day 4, 8, 15, 22, 25, 29, 36, 43, 50, 57, 64, 71, 85 or later following administration of the IL-4/IL-13 pathway inhibitor (e.g., following subcutaneous administration of about 300 mg of an anti-IL-4R antibody or antigen-binding fragment thereof). In certain exemplary embodiments of the present invention, administration of an IL-4/IL-13 pathway inhibitor to a subject results in a decrease from baseline in SDI of at least 40%.

Eosinophilic Esophagitis Activity Index (EEsAI). The EEsAI is a non-validated, multimodular index in development at University Hospital Inselspital (Berne, Switzerland) (Schoepfer 2014), a part of the international EEsAI study group. The EEsAI PRO module (questionnaire) used in this study includes items related to the intensity and frequency of dysphagia, the influence of specific food groups on dysphagia symptoms, and other symptoms independent of eating or drinking (i.e., heartburn, acid regurgitation, and chest pain). The total EEsAI PRO score ranges from 0 to 100 (FIG. 1), wherein higher scores indicate worse symptoms. The score consists of 5 parts: frequency of trouble swallowing, duration of trouble swallowing, pain when swallowing, visual dysphagia question, and avoidance, modification and slow eating (AMS). According to certain embodiments of the present invention, administration of an IL-4/IL-13 pathway inhibitor to a patient results in a decrease in EEsAI score.

For example, the present invention includes therapeutic methods which result in a decrease from baseline in EEsAI score of at least about 5%, 10%, 15%, 20%, 25%, 30%, 35%, or more at day 4, 8, 15, 22, 25, 29, 36, 43, 50, 57, 64, 71, 85 or later following administration of the IL-4/IL-13 pathway inhibitor (e.g., following subcutaneous administration of about 300 mg of an anti-IL-4R antibody or antigen-binding fragment thereof). In certain exemplary embodiments of the present invention, administration of an IL-4/IL-13 pathway inhibitor to a subject results in a decrease from baseline in EEsAI score of at least 30% after administration.

Eosinophilic Esophagitis Edema Rinds Exudates Furrows and Strictures (EoE-EREFS). The EoE-EREFS (edema, rings, exudates, furrows, strictures) is used to measure the endoscopically identified EoE esophageal mucosal inflammatory and remodeling features. This instrument includes a total of 17 items related to the presence and severity of esophageal features. The specific esophageal features include: rings (concentric rings around esophagus—absent, mild, moderate, severe, not applicable); strictures (narrowing of the esophagus—yes, no, not applicable); diameter of the stricture (if applicable); exudates (refer to white plaques—absent, mild, severe), furrows (vertical lines down the esophagus—absent, present); edema (loss of vascular markings of the mucosa—absent, present); crêpe paper esophagus (absent, present); overall general appearance incorporating all endoscopically identified EoE findings (i.e., fixed rings, strictures, whitish exudates, furrowing, edema, and crêpe paper mucosa). In addition, mucosal changes associated with gastroesophageal reflux disease are recorded using the Los Angeles classification system for erosions (No Erosions or LA Classification A, B, C, D). The EoE esophageal characteristics are analyzed based on the EoE-EREFS, a validated scoring system for inflammatory and remodeling features of disease using both overall scores and scores for each individual characteristic (Hirano 2014). According to certain embodiments of the present invention, administration of an IL-4/IL-13 pathway inhibitor to a patient results in a decrease in EoE-EREFS score. For example, the present invention includes therapeutic methods which result in a decrease from baseline in EREFS score of at least about 10%, 15%, 20%, 25%, 30%, 35%, 40%, 45%, 50%, 55%, 60%, 65%, 70%, 75% or more at day 4, 8, 15, 22, 25, 29, 36, 43, 50, 57, 64, 71, 85 or later following administration of the IL-4/IL-13 pathway inhibitor (e.g., following subcutaneous administration of about 300 mg of an anti-IL-4R antibody or antigen-binding fragment thereof).

Eosinophilic Esophagitis Histological Scoring System (EoE-HSS). The EoE-HSS generate separate severity (grade) and extent (stage) disease scores. The score is used to measure 8 histologic features (parameters) of EoE from 3 different regions (proximal, mid and distal) of the esophagus (Collins et al 2017). The 8 parameters include: eosinophil density, basal zone hyperplasia, eosinophil abscesses, eosinophil surface layering, dilated intercellular spaces, surface epithelial alteration, dyskeratotic cells, and lamina propria fibrosis. A scale of 0-3 is used for each parameter, both grade and stage (0 being least inflamed, normal). According to certain embodiments of the present invention, administration of an IL-4/IL-13 pathway inhibitor to a patient results in a decrease in EoE-HSS score. For example, the present invention includes therapeutic methods which result in a decrease from baseline in EoE-HSS of at least about 10%, 15%, 20%, 25%, 30%, 35%, 40%, 45%, 50%, 55%, 60%, 65%, 70%, 75% or more at day 4, 8, 15, 22, 25, 29, 36, 43, 50, 57, 64, 71, 85 or later following administration of the IL-4/IL-13 pathway inhibitor (e.g., following subcutaneous administration of about 300 mg of an anti-IL-4R antibody or antigen-binding fragment thereof). In certain exemplary embodiments of the present invention, administration of an IL-4/IL-13 pathway inhibitor to a subject results in a decrease from baseline in EoE-HSS score of at least 50%.

Esophageal intraepithelial eosinophils. It refers to ≥15 eosinophils per high powered field (hpf) in esophageal biopsies. Peak intraepithelial eosinophils refers to ≥15 eosinophils per high powered field in at least 2 of 3 esophageal regions sampled. According to certain embodiments of the present invention, administration of an IL-4/IL-13 pathway inhibitor to a patient results in a decrease in peak intraepithelial eosinophils. For example, the present invention includes therapeutic methods which result in a decrease from baseline in intraepithelial eosinophils of at least about 10%, 15%, 20%, 25%, 30%, 35%, 40%, 45%, 50%, 55%, 60%, 65%, 70%, 75%, 80%, 85% or more at day 4, 8, 15, 22, 25, 29, 36, 43, 50, 57, 64, 71, 85 or later following administration of the IL-4/IL-13 pathway inhibitor (e.g., following subcutaneous administration of about 300 mg of an anti-IL-4R antibody or antigen-binding fragment thereof). In certain exemplary embodiments of the present invention, administration of an IL-4/IL-13 pathway inhibitor to a subject results in a decrease from baseline in intraepithelial eosinophils of at least 85%.

Esophageal Distensibility. Esophageal distensibility is assessed by using the endoluminal functional lumen imaging probe (EndoFLIP, Crospon, Ireland) to measure the diameter of the esophageal lumen and pressure. The EndoFLIP device is a catheter based procedure that measures the cross sectional area at multiple sites along the esophagus with simultaneous intraluminal pressure recordings during volumetric distension of the esophagus. The analyses of cross sectional area versus pressure relationships of the esophagus allow for determination of esophageal compliance as well as the distensibility plateau (DP). The DP has been shown to be significantly reduced in patients with EoE compared to healthy controls (Kwiatek 2011). According to certain embodiments of the present invention, administration of an IL-4/IL-13 pathway inhibitor to a patient results in an increase in esophageal distensibility. For example, the present invention includes therapeutic methods which result in an increase from baseline in esophageal distensibility of at least about 5%, 10%, 15%, 20%, 25% or more at the end of week 1, 2, 3, 4, 5, 6, 7, 8, 9, 10, 11, 12, or later following administration of the IL-4/IL-13 pathway inhibitor (e.g., following subcutaneous administration of about 300 mg of an anti-IL-4R antibody or antigen-binding fragment thereof). In certain exemplary embodiments of the present invention, administration of an IL-4/IL-13 pathway inhibitor to a subject results in an increase from baseline in esophageal distensibility of at least 10%, as measured by impedance planimetry.

Adult Eosinophilic Esophagitis Quality of Life (EoE-QoL-A) Questionnaire. The EoE-QOL-A questionnaire is a validated disease-specific measure of health-related quality of life in EoE patients (Taft 2011). The instrument used in this study, the EoE-QOL-A v.3.0, includes 30 items related to established domains such as social functioning, emotional functioning, and disease impact of daily life experiences. The EoE-QOL-A has a 1-week recall period. The items are graded on a 5-point scale: 'Not at All,' 'Slightly,' 'Moderately,' 'Quite a bit,' and 'Extremely'. According to certain embodiments, administration of an IL-4/IL-13 pathway inhibitor to a patient results in an increase in quality of life parameters in the patient.

IL-4/IL-13 Pathway Inhibitors

The methods of the present invention comprise administering to a subject in need thereof a therapeutic composition comprising an IL-4/IL-13 pathway inhibitor.

As used herein, an "IL-4/IL-13 pathway inhibitor" (also referred to herein as an "IL-4/IL-13 pathway antagonist," an "IL-4/IL-13 pathway blocker," etc.) is any agent that inhibits or attenuates at least one of: (i) the binding of IL-4 and/or IL-13 to their respective receptors; (ii) signaling and/or activity of IL-4 and/or IL-13; and/or (iii) the downstream signaling/activity that results from binding of IL-4 and/or IL-13 to their respective receptors. Exemplary IL-4/IL-13 pathway inhibitors include, but are not limited to, anti-IL-4 antibodies (e.g., the antibodies disclosed in U.S. Pat. No. 7,740,843, and US Patent Application Publications 20100297110, 20160207995), anti-IL-13 antibodies (e.g., the antibodies disclosed in U.S. Pat. Nos. 7,501,121, 7,674,459, 7,807,788, 7,910,708, 7,915,388, 7,935,343, 8,088,618, 8,691,233, 9,605,065, US Patent Application Publications 20060073148, 20080044420, and EP2627673B1), bispecific antibodies that bind to IL-4 and IL-13 (e.g., the antibodies disclosed in U.S. Pat. No. 8,388,965, US Patent Application Publications 20110008345, 20130251718, 20160207995), and IL-4 receptor (IL-4R) inhibitors (described below).

As used herein, an "IL-4R inhibitor" (also referred to herein as an "IL-4/IL-13 pathway inhibitor," an "IL-4Rα antagonist," an "IL-4R blocker," an "IL-4Rα blocker," etc.) is any agent that binds to or interacts with IL-4Rα or an IL-4R ligand, and inhibits or attenuates the normal biological signaling function a type 1 and/or a type 2 IL-4 receptor. Human IL-4Rα has the amino acid sequence of SEQ ID NO: 11. A type 1 IL-4 receptor is a dimeric receptor comprising an IL-4Rα chain and a γc chain. A type 2 IL-4 receptor is a dimeric receptor comprising an IL-4Rα chain and an IL-13Rα1 chain. Type 1 IL-4 receptors interact with and are stimulated by IL-4, while type 2 IL-4 receptors interact with and are stimulated by both IL-4 and IL-13. Thus, the IL-4R inhibitors that can be used in the methods of the present invention may function by blocking IL-4-mediated signaling, IL-13-mediated signaling, or both IL-4- and IL-13-mediated signaling. The IL-4R inhibitors of the present invention may thus prevent the interaction of IL-4 and/or IL-13 with a type 1 or type 2 receptor.

Non-limiting examples of categories of IL-4R inhibitors include IL-4 muteins (e.g., pitrakinra), small molecule IL-4R inhibitors, anti-IL-4R aptamers, peptide-based IL-4R inhibitors (e.g., "peptibody" molecules), "receptor-bodies" (e.g., engineered molecules comprising the ligand-binding domain of an IL-4R component), and antibodies or antigen-binding fragments of antibodies that specifically bind human IL-4Rα. As used herein, IL-4R inhibitors also include antigen-binding proteins that specifically bind IL-4 and/or IL-13.

Anti-IL-4Rα Antibodies and Antigen-Binding Fragments Thereof

According to certain exemplary embodiments of the present invention, the IL-4/IL-13 pathway inhibitor is an anti-IL-4Rα antibody or antigen-binding fragment thereof. The term "antibody," as used herein, includes immunoglobulin molecules comprising four polypeptide chains, two heavy (H) chains and two light (L) chains inter-connected by disulfide bonds, as well as multimers thereof (e.g., IgM). In a typical antibody, each heavy chain comprises a heavy chain variable region (abbreviated herein as HCVR or $V_H$) and a heavy chain constant region. The heavy chain constant region comprises three domains, $C_H1$, $C_H2$ and $C_H3$. Each light chain comprises a light chain variable region (abbreviated herein as LCVR or $V_L$) and a light chain constant region. The light chain constant region comprises one domain ($C_L1$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different embodiments of the invention, the FRs of the anti-IL-4R antibody (or antigen-binding portion thereof) may be identical to the human germline sequences, or may be naturally or artificially modified. An amino acid consensus sequence may be defined based on a side-by-side analysis of two or more CDRs.

The term "antibody," as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR that is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$-$C_H1$; (ii) $V_H$-$C_H2$; (iii) $V_H$-$C_H3$; (iv) $V_H$-$C_H1$-$C_H2$; (V) $V_H$-$C_H1$-$C_H2$-$C_H3$; (vi) $V_H$-$C_H2$-$C_H3$; (Vii) $V_H$-$C_L$; (viii) $V_L$-$C_H1$; (ix) $V_L$-$C_H2$; (x) $V_L$-$C_H3$; (xi) $V_L$-$C_H1$-$C_H2$; (xii) $V_L$-$C_H1$-$C_H2$-$C_H3$; (xiii) $V_L$-$C_H2$-$C_H3$; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment of an antibody of the present invention may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

The term "antibody," as used herein, also includes multispecific (e.g., bispecific) antibodies. A multispecific antibody or antigen-binding fragment of an antibody will typically comprise at least two different variable domains, wherein each variable domain is capable of specifically binding to a separate antigen or to a different epitope on the same antigen. Any multispecific antibody format may be adapted for use in the context of an antibody or antigen-binding fragment of an antibody of the present invention using routine techniques available in the art. For example, the present invention includes methods comprising the use of bispecific antibodies wherein one arm of an immunoglobulin is specific for IL-4Rα or a fragment thereof, and the other arm of the immunoglobulin is specific for a second therapeutic target or is conjugated to a therapeutic moiety. Exemplary bispecific formats that can be used in the context of the present invention include, without limitation, e.g., scFv-based or diabody bispecific formats, IgG-scFv fusions, dual variable domain (DVD)-Ig, Quadroma, knobs-into-holes, common light chain (e.g., common light chain with knobs-into-holes, etc.), CrossMab, CrossFab, (SEED) body, leucine zipper, Duobody, IgG1/IgG2, dual acting Fab (DAF)-IgG, and Mab$^2$ bispecific formats (see, e.g., Klein et al. 2012, mAbs 4:6, 1-11, and references cited therein, for a review of the foregoing formats). Bispecific antibodies can also be constructed using peptide/nucleic acid conjugation, e.g., wherein unnatural amino acids with orthogonal chemical reactivity are used to generate site-specific antibody-oligonucleotide conjugates which then self-assemble into multimeric complexes with defined composition, valency and geometry. (See, e.g., Kazane et al., *J. Am. Chem. Soc.* [Epub: Dec. 4, 2012]).

The antibodies used in the methods of the present invention may be human antibodies. The term "human antibody," as used herein, is intended to include antibodies having variable and constant regions derived from human germline immunoglobulin sequences. The human antibodies of the invention may nonetheless include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody," as used herein, is not intended to include antibodies in which CDR sequences derived from the germline of another mammalian species, such as a mouse, have been grafted onto human framework sequences.

The antibodies used in the methods of the present invention may be recombinant human antibodies. The term "recombinant human antibody," as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al. (1992) Nucl. Acids Res. 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germ line repertoire in vivo.

According to certain embodiments, the antibodies used in the methods of the present invention specifically bind IL-4Rα. The term "specifically binds," or the like, means that an antibody or antigen-binding fragment thereof forms a complex with an antigen that is relatively stable under physiologic conditions. Methods for determining whether an antibody specifically binds to an antigen are well known in the art and include, for example, equilibrium dialysis, surface plasmon resonance, and the like. For example, an antibody that "specifically binds" IL-4Rα, as used in the context of the present invention, includes antibodies that bind IL-4Rα or portion thereof with a Ko of less than about 500 nM, less than about 300 nM, less than about 200 nM, less than about 100 nM, less than about 90 nM, less than about 80 nM, less than about 70 nM, less than about 60 nM, less than about 50 nM, less than about 40 nM, less than about 30 nM, less than about 20 nM, less than about 10 nM, less than about 5 nM, less than about 4 nM, less than about 3 nM, less than about 2 nM, less than about 1 nM or less than about 0.5 nM, as measured in a surface plasmon resonance assay. An isolated antibody that specifically binds human IL-4Rα may, however, have cross-reactivity to other antigens, such as IL-4Rα molecules from other (non-human) species.

According to certain exemplary embodiments of the present invention, the IL-4/IL-13 pathway inhibitor is an anti-IL-4Rα antibody, or antigen-binding fragment thereof comprising a heavy chain variable region (HCVR), light chain variable region (LCVR), and/or complementarity determining regions (CDRs) comprising any of the amino acid sequences of the anti-IL-4R antibodies as set forth in U.S. Pat. No. 7,608,693. In certain exemplary embodiments, the anti-IL-4Rα antibody or antigen-binding fragment thereof that can be used in the context of the methods of the present invention comprises the heavy chain complementarity determining regions (HCDRs) of a heavy chain variable region (HCVR) comprising the amino acid sequence of SEQ ID NO: 1 and the light chain complementarity determining regions (LCDRs) of a light chain variable region (LCVR) comprising the amino acid sequence of SEQ ID NO: 2. According to certain embodiments, the anti-IL-4Rα antibody or antigen-binding fragment thereof comprises three HCDRs (HCDR1, HCDR2 and HCDR3) and three LCDRs (LCDR1, LCDR2 and LCDR3), wherein the HCDR1 comprises the amino acid sequence of SEQ ID NO: 3; the HCDR2 comprises the amino acid sequence of SEQ ID NO: 4; the HCDR3 comprises the amino acid sequence of SEQ ID NO: 5; the LCDR1 comprises the amino acid sequence of SEQ ID NO: 6; the LCDR2 comprises the amino acid sequence of SEQ ID NO: 7; and the LCDR3 comprises the amino acid sequence of SEQ ID NO: 8. In yet other embodiments, the anti-IL-4R antibody or antigen-binding fragment thereof comprises an HCVR comprising SEQ ID NO: 1 and an LCVR comprising SEQ ID NO: 2. In certain embodiments, the methods of the present invention comprise the use of an anti-IL-4R antibody, wherein the antibody comprises a heavy chain comprising the amino acid sequence of SEQ ID NO: 9. In some embodiments, the anti-IL-4R antibody comprises a light chain comprising the amino acid sequence of SEQ ID NO: 10. An exemplary antibody comprising a heavy chain comprising the amino acid sequence of SEQ ID NO: 9 and a light chain comprising the amino acid sequence of SEQ ID NO: 10 is the fully human anti-IL-4R antibody known as dupilumab. According to certain exemplary embodiments, the methods of the present invention comprise the use of dupilumab, or a bioequivalent thereof. The term "bioequivalent", as used herein, refers to anti-IL-4R antibodies or IL-4R-binding proteins or fragments thereof that are pharmaceutical equivalents or pharmaceutical alternatives whose rate and/or extent of absorption do not show a significant difference with that of dupilumab when administered at the same molar dose under similar experimental conditions, either single dose or multiple dose. In the context of the invention, the term refers to antigen-binding proteins that bind to IL-4R which do not have clinically meaningful differences with dupilumab in their safety, purity and/or potency.

Other anti-IL-4Rα antibodies that can be used in the context of the methods of the present invention include, e.g., the antibody referred to and known in the art as AMG317 (Corren et al., 2010, *Am J Respir Crit Care Med.,* 181(8): 788-796), or MEDI 9314, or any of the anti-IL-4Rα antibodies as set forth in U.S. Pat. Nos. 7,186,809, 7,605,237, 7,638,606, 8,092,804, 8,679,487, or U.S. Pat. No. 8,877,189.

The anti-IL-4Rα antibodies used in the context of the methods of the present invention may have pH-dependent binding characteristics. For example, an anti-IL-4Rα antibody for use in the methods of the present invention may exhibit reduced binding to IL-4Rα at acidic pH as compared to neutral pH. Alternatively, an anti-IL-4Rα antibody of the invention may exhibit enhanced binding to its antigen at acidic pH as compared to neutral pH. The expression "acidic pH" includes pH values less than about 6.2, e.g., about 6.0, 5.95, 5.9, 5.85, 5.8, 5.75, 5.7, 5.65, 5.6, 5.55, 5.5, 5.45, 5.4, 5.35, 5.3, 5.25, 5.2, 5.15, 5.1, 5.05, 5.0, or less. As used herein, the expression "neutral pH" means a pH of about 7.0 to about 7.4. The expression "neutral pH" includes pH values of about 7.0, 7.05, 7.1, 7.15, 7.2, 7.25, 7.3, 7.35, and 7.4.

In certain instances, "reduced binding to IL-4Rα at acidic pH as compared to neutral pH" is expressed in terms of a ratio of the Ko value of the antibody binding to IL-4Rα at acidic pH to the $K_D$ value of the antibody binding to IL-4Rα at neutral pH (or vice versa). For example, an antibody or antigen-binding fragment thereof may be regarded as exhibiting "reduced binding to IL-4Rα at acidic pH as compared to neutral pH" for purposes of the present invention if the antibody or antigen-binding fragment thereof exhibits an acidic/neutral Ko ratio of about 3.0 or greater. In certain exemplary embodiments, the acidic/neutral Ko ratio for an antibody or antigen-binding fragment of the present invention can be about 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 20.0, 25.0, 30.0, 40.0, 50.0, 60.0, 70.0, 100.0, or greater.

Antibodies with pH-dependent binding characteristics may be obtained, e.g., by screening a population of antibodies for reduced (or enhanced) binding to a particular antigen at acidic pH as compared to neutral pH. Additionally, modifications of the antigen-binding domain at the amino acid level may yield antibodies with pH-dependent characteristics. For example, by substituting one or more amino acids of an antigen-binding domain (e.g., within a CDR) with a histidine residue, an antibody with reduced antigen-binding at acidic pH relative to neutral pH may be obtained. As used herein, the expression "acidic pH" means a pH of 6.0 or less.

Pharmaceutical Compositions

The present invention includes methods that comprise administering an IL-4/IL-13 pathway inhibitor to a subject wherein the IL-4/IL-13 pathway inhibitor is contained within a pharmaceutical composition. The pharmaceutical compositions of the invention may be formulated with suitable carriers, excipients, and other agents that provide suitable transfer, delivery, tolerance, and the like. A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

Various delivery systems are known and can be used to administer the pharmaceutical composition of the invention, e.g., encapsulation in liposomes, microparticles, microcapsules, recombinant cells capable of expressing the mutant viruses, receptor mediated endocytosis (see, e.g., Wu et al., 1987, J. Biol. Chem. 262: 4429-4432). Methods of administration include, but are not limited to, intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents.

A pharmaceutical composition of the present invention can be delivered subcutaneously or intravenously with a standard needle and syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

In certain situations, the pharmaceutical composition can be delivered in a controlled release system. In one embodiment, a pump may be used. In another embodiment, polymeric materials can be used; see, Medical Applications of Controlled Release, Langer and Wise (eds.), 1974, CRC Pres., Boca Raton, Fla. In yet another embodiment, a controlled release system can be placed in proximity of the composition's target, thus requiring only a fraction of the systemic dose (see, e.g., Goodson, 1984, in Medical Applications of Controlled Release, supra, vol. 2, pp. 115-138). Other controlled release systems are discussed in the review by Langer, 1990, Science 249:1527-1533.

The injectable preparations may include dosage forms for intravenous, subcutaneous, intracutaneous and intramuscular injections, drip infusions, etc. These injectable preparations may be prepared by known methods. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc.

Exemplary pharmaceutical compositions comprising an anti-IL-4R antibody that can be used in the context of the present invention are disclosed, e.g., in U.S. Pat. No. 8,945,559.

Administration Regimens

The present invention includes methods comprising administering to a subject an IL-4/IL-13 pathway inhibitor at a dosing frequency of about four times a week, twice a week, once a week, once every two weeks, once every three weeks, once every four weeks, once every five weeks, once every six weeks, once every eight weeks, once every twelve weeks, or less frequently so long as a therapeutic response is achieved. In certain embodiments involving the administration of an IL-4/IL-13 pathway inhibitor (e.g., an anti-IL-4R antibody), once a week dosing at an amount of about 25 mg, 50 mg, 100 mg, 150 mg, 200 mg, or 300 mg, is employed. In certain embodiments involving the administration of an anti-IL-4R antibody, once in 2 weeks dosing at an amount of about 25 mg, 50 mg, 100 mg, 150 mg, 200 mg, or 300 mg, is employed.

According to certain embodiments of the present invention, multiple doses of an IL-4/IL-13 pathway inhibitor may be administered to a subject over a defined time course. The methods according to this aspect of the invention comprise sequentially administering to a subject multiple doses of an IL-4/IL-13 pathway inhibitor. As used herein, "sequentially administering" means that each dose of IL-4/IL-13 pathway inhibitor is administered to the subject at a different point in time, e.g., on different days separated by a predetermined interval (e.g., hours, days, weeks or months). The present invention includes methods that comprise sequentially administering to the patient a single initial dose of an IL-4/IL-13 pathway inhibitor, followed by one or more secondary doses of the IL-4/IL-13 pathway inhibitor, and optionally followed by one or more tertiary doses of the IL-4/IL-13 pathway inhibitor.

The terms "initial dose," "secondary doses," and "tertiary doses," refer to the temporal sequence of administration of the IL-4/IL-13 pathway inhibitor. Thus, the "initial dose" is the dose that is administered at the beginning of the treatment regimen (also referred to as the "baseline dose"); the "secondary doses" are the doses that are administered after the initial dose; and the "tertiary doses" are the doses that are administered after the secondary doses. The initial, secondary, and tertiary doses may all contain the same amount of IL-4/IL-13 pathway inhibitor, but generally may differ from one another in terms of frequency of administration. In certain embodiments, however, the amount of IL-4/IL-13 pathway inhibitor contained in the initial, secondary and/or tertiary doses varies from one another (e.g., adjusted up or down as appropriate) during the course of treatment. In certain embodiments, the initial dose comprises a first amount of the antibody or antigen-binding fragment thereof and the one or more secondary doses each comprise a second amount of the antibody or antigen-binding fragment thereof. In some embodiments, the first amount of antibody or fragment thereof (initial dose) is 1.5×, 2×, 2.5×, 3×, 3.5×, 4×, or 5× the second amount of the antibody or antigen-binding fragment thereof (secondary dose). In certain embodiments, one or more (e.g., 1, 2, 3, 4, or 5) doses are administered at the beginning of the treatment regimen as "loading doses" followed by subsequent doses that are administered on a less frequent basis (e.g., "maintenance doses"). For example, an IL-4/IL-13 pathway inhibitor may be administered to a patient in need thereof at a loading dose of about 300 mg to about 600 mg followed by one or more maintenance doses of about 25 mg to about 400 mg. In one embodiment, the initial dose and the one or more secondary doses each include 10 mg to 600 mg of the IL-4/IL-13 pathway inhibitor, e.g., 100 mg to 400 mg of the IL-4/IL-13 pathway inhibitor, e.g., 10 mg, 25 mg, 50 mg, 100 mg, 150 mg, 200 mg, 250 mg, 300 mg, 400 mg or 500 mg of the IL-4/IL-13 pathway inhibitor. In one embodiment, the initial dose is 2× the secondary dose.

In one exemplary embodiment of the present invention, each secondary and/or tertiary dose is administered 1 to 14 (e.g., 1, 1½, 2, 2½, 3, 3½, 4, 4½, 5, 5½, 6, 6½, 7, 7½, 8, 8½, 9, 9½, 10, 10½, 11, 11½, 12, 12½, 13, 13½, 14, 14½, or more) weeks after the immediately preceding dose. The phrase "the immediately preceding dose," as used herein, means, in a sequence of multiple administrations, the dose of IL-4/IL-13 pathway inhibitor that is administered to a patient prior to the administration of the very next dose in the sequence with no intervening doses.

The methods according to this aspect of the invention may comprise administering to a patient any number of secondary and/or tertiary doses of an IL-4/IL-13 pathway inhibitor. For example, in certain embodiments, only a single secondary dose is administered to the patient. In other embodiments, two or more (e.g., 2, 3, 4, 5, 6, 7, 8, or more) secondary doses are administered to the patient. Likewise, in certain embodiments, only a single tertiary dose is administered to the patient. In other embodiments, two or more (e.g., 2, 3, 4, 5, 6, 7, 8, or more) tertiary doses are administered to the patient.

In embodiments involving multiple secondary doses, each secondary dose may be administered at the same frequency as the other secondary doses. For example, each secondary dose may be administered to the patient 1 to 6 weeks after the immediately preceding dose. Similarly, in embodiments involving multiple tertiary doses, each tertiary dose may be administered at the same frequency as the other tertiary doses. For example, each tertiary dose may be administered to the patient 2 to 4 weeks after the immediately preceding dose. Alternatively, the frequency at which the secondary and/or tertiary doses are administered to a patient can vary over the course of the regimen.

The methods of the present invention, according to certain embodiments, comprise administering to the subject a corticosteroid (CS) in combination with an IL-4/IL-13 pathway inhibitor (e.g., an anti-IL-4R antibody). As used herein, the expression "in combination with" means that the CS is administered before, after, or concurrent with the IL-4/IL-13 pathway inhibitor. The term "in combination with" also includes sequential or concomitant administration of IL-4/IL-13 pathway inhibitor and CS.

For example, when administered "before" the IL-4/IL-13 pathway inhibitor, the CS may be administered more than 72 hours, about 72 hours, about 60 hours, about 48 hours, about 36 hours, about 24 hours, about 12 hours, about 10 hours, about 8 hours, about 6 hours, about 4 hours, about 2 hours, about 1 hour, about 30 minutes, about 15 minutes or about 10 minutes prior to the administration of the IL-4/IL-13 pathway inhibitor. When administered "after" the IL-4/IL-13 pathway inhibitor, the CS may be administered about 10 minutes, about 15 minutes, about 30 minutes, about 1 hour, about 2 hours, about 4 hours, about 6 hours, about 8 hours, about 10 hours, about 12 hours, about 24 hours, about 36 hours, about 48 hours, about 60 hours, about 72 hours, or more than 72 hours after the administration of the IL-4/IL-13 pathway inhibitor. Administration "concurrent" with the IL-4/IL-13 pathway inhibitor means that the CS is administered to the subject in a separate dosage form within less than 5 minutes (before, after, or at the same time) of administration of the IL-4/IL-13 pathway inhibitor, or administered to the subject as a single combined dosage formulation comprising both the CS and the IL-4/IL-13 pathway inhibitor.

Dosage

The amount of IL-4/IL-13 pathway inhibitor (e.g., anti-IL-4Rα antibody) administered to a subject according to the methods of the present invention is, generally, a therapeutically effective amount. As used herein, the phrase "therapeutically effective amount" means an amount of IL-4/IL-13 pathway inhibitor that results in one or more of: (a) a reduction in the severity or duration of a symptom of eosinophilic esophagitis; (b) a reduction in the number of eosinophils in esophagus; (c) increase in esophagus distensibility; (d) reduction in episodes of dysphagia; (e) prevention or alleviation of an allergic reaction; and (f) a reduction in the use or need for conventional allergy therapy (e.g., reduced or eliminated use of antihistamines, decongestants, nasal or inhaled steroids, anti-IgE treatment, epinephrine, etc.).

In the case of an anti-IL-4Rα antibody, a therapeutically effective amount can be from about 0.05 mg to about 600 mg, e.g., about 0.05 mg, about 0.1 mg, about 1.0 mg, about 1.5 mg, about 2.0 mg, about 10 mg, about 20 mg, about 30 mg, about 40 mg, about 50 mg, about 60 mg, about 70 mg, about 80 mg, about 90 mg, about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, about 300 mg, about 310 mg, about 320 mg, about 330 mg, about 340 mg, about 350 mg, about 360 mg, about 370 mg, about 380 mg, about 390 mg, about 400 mg, about 410 mg, about 420 mg, about 430 mg, about 440 mg, about 450 mg, about 460 mg, about 470 mg, about 480 mg, about 490 mg, about 500 mg, about 510 mg, about 520 mg, about 530 mg, about 540 mg, about 550 mg, about 560 mg, about 570 mg, about 580 mg, about 590 mg, or about 600 mg, of the anti-IL-4R antibody. In certain embodiments, 300 mg of an anti-IL-4R antibody is administered.

The amount of IL-4/IL-13 pathway inhibitor contained within the individual doses may be expressed in terms of milligrams of antibody per kilogram of patient body weight (i.e., mg/kg). For example, the IL-4/IL-13 pathway inhibitor (e.g., anti-IL-4Rα antibody) may be administered to a patient at a dose of about 0.0001 to about 100 mg/kg of patient body weight.

Selected Embodiments

In Embodiment 1, the present invention includes a method of reducing dysphagia comprising: (a) selecting a patient with at least one of the following characteristics: (i) the patient exhibits episodes of dysphagia per week; (ii) the patient has been treated previously with high-dose proton pump inhibitors (PPIs); and (iii) the patient has had at least one prior esophageal dilation; and (b) administering a therapeutically effective amount of a pharmaceutical composition comprising an interleukin-4/interleukin-13 (IL-4/IL-13) pathway inhibitor to the patient in need thereof.

In Embodiment 2, the present invention includes a method of increasing esophageal distensibility comprising: (a) selecting a patient with at least one of the following characteristics: (i) the patient exhibits episodes of dysphagia per week; (ii) the patient has been treated previously with high-dose PPIs; and (iii) the patient has had at least one prior esophageal dilation; and (b) administering a therapeutically effective amount of a pharmaceutical composition comprising an IL-4/IL-13 pathway inhibitor to the patient in need thereof.

In Embodiment 3, the present invention includes the method of Embodiment 1 or 2, wherein the patient has moderate-to-severe EoE.

In Embodiment 4, the present invention includes a method of treating, preventing or ameliorating at least one symptom or indication of active eosinophilic esophagitis (EoE) comprising administering a therapeutically effective amount of a pharmaceutical composition comprising an IL-4/IL-13 pathway inhibitor to a patient in need thereof.

In Embodiment 5, the present invention includes the method of any one of Embodiments 1 to 4, wherein the patient has one or more characteristics selected from the group consisting of: (1) the patient has 15 eosinophils per high powered field (hpf) in the esophagus prior to or at the time of the treatment ("baseline"); (2) prior treatment with at least one of high dose PPIs, esophageal dilation, corticosteroids, allergen withdrawal and/or diet modification; (3) the patient exhibits episodes of dysphagia per week; (4) the patient is unresponsive or resistant to prior treatment with high dose PPIs or esophageal dilation; (5) the patient has a Straumann Dysphagia Instrument (SDI) score ≥2; (6) the patient has an Eosinophilic Esophagitis Severity and Activity Index (EEsAI) score ≥30, ≥40, or ≥50; (7) the patient suffers from EoE for at least 3 years; (8) the patient, prior to or at the time of administration of the IL-4/IL-13 pathway inhibitor, has or is diagnosed with a disease or disorder selected from the group consisting of food allergy, atopic dermatitis, asthma, allergic rhinitis and allergic conjunctivitis; and (9) the patient has an elevated level of a biomarker selected from the group consisting of eotaxin-3, periostin, serum IgE (total and allergen-specific), IL-13, IL-5, serum thymus and activation regulated chemokine (TARC), thymic stromal lymphopoietin (TSLP), serum eosinophilic cationic protein (ECP), and eosinophil-derived neurotoxin (EDN).

In Embodiment 6, the present invention includes the method of any one of Embodiments 1 to 5, wherein administration of the IL-4/IL-13 pathway inhibitor results in improvement of an EoE-related parameter selected from the group consisting of: (a) reduction of at least 40% from baseline in dysphagia frequency and severity, as measured by Straumann Dysphagia Instrument (SDI) score; (b) reduction of 3 points from baseline in the SDI score; (c) reduction of more than 85% from baseline in peak intraepithelial eosinophil count in proximal, mid and/or distal regions of the esophagus; (d) increase of at least 10% from baseline in esophageal distensibility, as measured by impedance planimetry; (e) decrease of more than 50% from baseline in severity and extent of disease, as measured by EoE Histology Scoring System (HSS) score; and (f) reduction of more than 30% from baseline in dysphagia, as measured by Eosinophilic Esophagitis Severity and Activity Index (EEsAI) score.

In Embodiment 7, the present invention includes the method of any one of Embodiments 1 to 6, wherein the IL-4/IL-13 pathway inhibitor is an antibody or antigen-binding fragment thereof that specifically binds IL-4 receptor (IL-4R).

In Embodiment 8, the present invention includes the method of any one of Embodiments 1 to 7, wherein the IL-4/IL-13 pathway inhibitor is administered at a dose of about 50-600 mg.

In Embodiment 9, the present invention includes the method of any one of Embodiments 1 to 8, wherein the IL-4/IL-13 pathway inhibitor is administered at a dose of about 300 mg.

In Embodiment 10, the present invention includes the method of any one of Embodiments 1 to 7, wherein the IL-4/IL-13 pathway inhibitor is administered at an initial dose followed by one or more secondary doses, wherein each secondary dose is administered 1 to 4 weeks after the immediately preceding dose.

In Embodiment 11, the present invention includes the method of Embodiment 10, wherein the initial dose comprises 50-600 mg of the IL-4/IL-13 pathway inhibitor.

In Embodiment 12, the present invention includes the method of Embodiment 10 or 11, wherein each secondary dose comprises 25-400 mg of the IL-4/IL-13 pathway inhibitor.

In Embodiment 13, the present invention includes the method of any one of Embodiments 10 to 12, wherein the initial dose comprises 600 mg of the IL-4/IL-13 pathway inhibitor and each secondary dose comprises 300 mg of the IL-4/IL-13 pathway inhibitor.

In Embodiment 14, the present invention includes the method of Embodiment 13, wherein each secondary dose is administered one week after the immediately preceding dose.

In Embodiment 15, the present invention includes the method of Embodiment 13, wherein each secondary dose is administered 2 weeks after the immediately preceding dose.

In Embodiment 16, the present invention includes the method of any one of Embodiments 4 to 15, wherein the symptom or indication of EoE is selected from the group consisting of eosinophilic infiltration of the esophagus, thickening of the esophageal wall, food refusal, vomiting, abdominal pain, heartburn, regurgitation, dysphagia and food impaction.

In Embodiment 17, the present invention includes the method of any one of Embodiments 1 to 16, wherein the patient exhibits an allergic reaction to a food allergen contained in a food item selected from the group consisting of a dairy product, egg, wheat, soy, corn, fish, shellfish, peanut, a tree nut, beef, chicken, oat, barley, pork, green beans, apple and pineapple.

In Embodiment 18, the present invention includes the method of any one of Embodiments 1 to 17, wherein the patient exhibits an allergic reaction to a non-food allergen derived from one of dust, pollen, mold, plant, cat, dog or insect.

In Embodiment 19, the present invention includes the method of any one of Embodiments 1 to 18, wherein the administration of the IL-4/IL-13 pathway inhibitor results in reducing the level of an EoE-associated biomarker in the subject.

In Embodiment 20, the present invention includes the method of Embodiment 19, wherein the EoE-associated biomarker is selected from the group consisting of eotaxin-3, periostin, serum IgE (total and allergen-specific), IL-13, IL-5, serum TARC, TSLP, serum ECP, and EDN.

In Embodiment 21, the present invention includes the method of any one of Embodiments 1 to 20, wherein the IL-4/IL-13 pathway inhibitor is administered in combination with a second therapeutic agent or therapy, wherein the second therapeutic agent or therapy is selected from the group consisting of an IL-1beta inhibitor, an IL-5 inhibitor, an IL-9 inhibitor, an IL-13 inhibitor, an IL-17 inhibitor, an IL-25 inhibitor, a TNFalpha inhibitor, an eotaxin-3 inhibitor, an IgE inhibitor, a prostaglandin D2 inhibitor, an immunosuppressant, a topical corticosteroid, an oral corticosteroid, a systemic corticosteroid, an inhaled corticosteroid, a glucocorticoid, a proton pump inhibitor, a NSAID, esophagus dilation, allergen removal and diet management.

In Embodiment 22, the present invention includes the method of any one of Embodiments 1 to 21, wherein the IL-4/IL-13 pathway inhibitor is selected from the group consisting of an anti-IL-4 antibody, an anti-IL-13 antibody, an anti-IL-4/IL-13 bispecific antibody, an IL-4 receptor (IL-4R) inhibitor, and an anti-IL-4R antibody.

In Embodiment 23, the present invention includes the method of Embodiment 22, wherein the IL-4/IL-13 pathway inhibitor is an IL-4R inhibitor.

In Embodiment 24, the present invention includes the method of Embodiment 22, wherein the IL-4/IL-13 pathway inhibitor is an anti-IL-4 antibody.

In Embodiment 25, the present invention includes the method of Embodiment 22, wherein the IL-4/IL-13 pathway inhibitor is an anti-IL-13 antibody.

In Embodiment 26, the present invention includes the method of Embodiment 22, wherein the IL-4/IL-13 pathway inhibitor is a bispecific antibody that specifically binds to IL-4 and IL-13.

In Embodiment 27, the present invention includes the method of any one of Embodiments 1 to 23, wherein the IL-4/IL-13 pathway inhibitor is an antibody or antigen-binding fragment thereof that binds IL-4Rα and prevents the interaction of IL-4 and/or IL-13 with a type 1 or type 2 IL-4 receptor.

In Embodiment 28, the present invention includes the method of Embodiment 27, wherein the antibody or antigen-binding fragment thereof prevents the interaction of IL-4 with both type 1 and type 2 IL-4 receptors.

In Embodiment 29, the present invention includes the method of Embodiment 28, wherein the antibody or antigen-binding fragment thereof comprises the heavy chain complementarity determining regions (HCDRs) of a heavy chain variable region (HCVR) comprising the amino acid sequence of SEQ ID NO: 1 and the light chain complementarity determining regions (LCDRs) of a light chain variable region (LCVR) comprising the amino acid sequence of SEQ ID NO: 2.

In Embodiment 30, the present invention includes the method of Embodiment 28, wherein the antibody or antigen-binding fragment thereof comprises three HCDRs (HCDR1, HCDR2 and HCDR3) and three LCDRs (LCDR1, LCDR2 and LCDR3), wherein the HCDR1 comprises the amino acid sequence of SEQ ID NO: 3; the HCDR2 comprises the amino acid sequence of SEQ ID NO: 4; the HCDR3 comprises the amino acid sequence of SEQ ID NO: 5; the LCDR1 comprises the amino acid sequence of SEQ ID NO: 6; the LCDR2 comprises the amino acid sequence of SEQ ID NO: 7; and the LCDR3 comprises the amino acid sequence of SEQ ID NO: 8.

In Embodiment 31, the present invention includes the method of Embodiment 30, wherein the HCVR comprises the amino acid sequence of SEQ ID NO: 1 and the LCVR comprises the amino acid sequence of SEQ ID NO: 2.

In Embodiment 32, the present invention includes the method of any one of Embodiments 29 to 31, wherein the antibody or antigen-binding fragment thereof comprises a heavy chain comprising the amino acid sequence of SEQ ID NO: 9 and a light chain comprising the amino acid sequence of SEQ ID NO: 10.

In Embodiment 33, the present invention includes the method of any one of Embodiments 1 to 31, wherein the IL-4/IL-13 pathway inhibitor is dupilumab or a bioequivalent thereof.

In Embodiment 34, the present invention includes the method of Embodiment 23, wherein the IL-4R inhibitor is AMG317 or MEDI9314.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1: Clinical Trial of Subcutaneously Administered Dupilumab in Adult Patients With Active, Moderate-to-severe Eosinophilic Esophagitis (EoE)

This study is a 32-week, double-blind, randomized, placebo-controlled study to investigate the efficacy, safety, tolerability and immunogenicity of dupilumab in adult patients with active EoE. Dupilumab is a fully human anti-IL-4R antibody comprising a heavy chain comprising the amino acid sequence of SEQ ID NO: 9 and a light chain comprising the amino acid sequence of SEQ ID NO: 10; an HCVR/LCVR amino acid sequence pair comprising SEQ ID NOs: 1/2; and heavy and light chain CDR sequences comprising SEQ ID NOs: 3-8.

Study Objectives

The primary objective of the study was to assess the clinical efficacy of repeat subcutaneous (SC) doses of dupilumab, compared with placebo, to relieve symptoms in adult patients with active, moderate to severe EoE.

The secondary objectives of the study were: (1) to assess the safety, tolerability, and immunogenicity of SC doses of dupilumab in adult patients with active, moderate to severe EoE; (2) to assess the effect of dupilumab on esophageal eosinophilic infiltration; and (3) to evaluate the pharmacokinetics (PK) of dupilumab in adult patients with EoE.

The exploratory objective of the study was to assess the effect of dupilumab on other esophageal biopsy pathologic features associated with EoE.

Study Design

This was a multicenter, double-blind, randomized, placebo-controlled study investigating the efficacy, safety, tolerability, PK, and immunogenicity of dupilumab in adult patients with EoE.

After providing informed consent, patient eligibility was assessed at the screening visit (to occur between day-35 and day-1). Patients who met eligibility criteria underwent day 1 baseline assessments. Patients were randomized in a 1:1 ratio to receive dupilumab or placebo during the 12-week double-blind treatment phase. After the 12-week double-blind treatment phase, patients were followed off study drug for an additional 16 weeks.

Patients received concomitant medications (except for prohibited medications [see below]) as needed, while continuing study treatment. Efficacy, safety, and laboratory assessments, and samples for dupilumab concentration and potential anti-drug antibody (ADA) response to dupilumab, as well as research samples were performed or collected at specified time points throughout the study.

Study Population

The target population included adult (18 to 65 years old) male or female patients with active EoE.

Inclusion Criteria: A patient had to meet the following criteria to be eligible for inclusion in the study:

(1) Male or female, 18 to 65 years old;
(2) Documented diagnosis of EoE by endoscopy prior to or at screening. Note: Must include a demonstration of intraepithelial eosinophilic infiltration (peak cell count ≥15 eosinophils/high power field [eos/hpf] [400×]) from esophageal biopsy specimens from endoscopy performed no more than 2 weeks after at least 8 weeks of treatment with high dose (or twice-daily dosing) proton pump inhibitors (PPIs);
(3) History (by patient report) of on average at least 2 episodes of dysphagia (with intake of solids off anti-inflammatory therapy) per week in the 4 weeks prior to screening and on average at least 2 episodes of documented dysphagia per week in the weeks between screening and baseline; dysphagia is defined as trouble swallowing solid food, or having solid food stick, by patient report;
(4) Must remain on a stabilized diet for at least 6 weeks prior to screening and during the course of the study; stable diet is defined as no initiation of single or multiple elimination diets or reintroduction of previously eliminated food groups;
(5) SDI PRO score at screening and baseline;
(6) Documented history of or presence of 1 or more of any of the following: allergic disease (e.g., allergic asthma, allergic rhinitis, AD, or food allergies), peripheral eosinophil counts ≥0.25 GI/L, serum total Immunoglobulin E (IgE) ≥100 kU/L;
(7) Willing and able to comply with all clinic visits and study-related procedures; able to understand and complete study-related questionnaires; provide signed informed consent; and
(8) Endoscopy with photographs performed at screening, with a demonstration of intraepithelial eosinophilic infiltration (peak cell count ≥15 eos/hpf) in at least 2 of the 3 biopsied esophageal regions (proximal, mid, or distal).

Exclusion Criteria: A patient who met any of the following criteria was ineligible to participate in this study: (1) Prior participation in a dupilumab (anti-IL-4R) clinical trial; (2) Other causes of esophageal eosinophilia or the following diseases: hypereosinophilic syndromes, Churg-Strauss vasculitis, and eosinophilic gastroenteritis; (3) History of achalasia, active *Helicobacter pylori* infection, Crohn's disease, ulcerative colitis, celiac disease, and prior esophageal surgery prior to screening; (4) Any esophageal stricture unable to be passed with a standard, diagnostic, adult (9 to10 mm) upper endoscope or any critical esophageal stricture that requires dilation at screening; (5) History of bleeding disorders or esophageal varices; (6) Use of chronic aspirin, nonsteroidal agents, or anti-coagulants within 2 weeks prior to screening. Patients should not stop these agents solely to become eligible for entry into this study; (7) Treatment with an investigational drug within 2 months or within 5 half-lives (if known), whichever is longer, prior to screening; (8) Use of systemic corticosteroids within 3 months or swallowed topical corticosteroids within 6 weeks prior to screening; (9) Use of inhaled or nasal corticosteroids within 3 months prior to screening and during the study, except stable dose for at least 3 months prior to screening biopsy, which cannot be changed during the study; (10) Treatment with oral immunotherapy (OIT) within 6 months prior to screening; (11) Allergen immunotherapy (sublingual immunotherapy [SLIT] and/or subcutaneous immunotherapy [SCIT], unless on stable dose for at least 1 year prior to screening; (12) The following treatments within 3 months before the screening visit, or any condition that, in the opinion of the investigator, is likely to require such treatment(s) during the 3 months of study treatment: Systemic immunosuppressive/immunomodulating drugs (e.g., omalizumab, cyclosporine, mycophenolate-mofetil, interferon-gamma [IFN-γ], Janus kinase inhibitors, azathioprine, methotrexate, leukotriene inhibitors [except stable dose for at least 3 months prior to screening], etc.); (13) Diagnosed with active parasitic infection; suspected parasitic infection, unless clinical and (if necessary) laboratory assessments have ruled out active infection before randomization; (14) Chronic or acute infection requiring treatment with systemic antibiotics, antivirals, or antifungals within 1 month prior to screening; (15) Use of oral antibiotics/anti-infectives within 2 weeks prior to screening; (16) Known or suspected immunosuppression, including history of invasive opportunistic infections (e.g., tuberculosis, non-tuberculous mycobacterial infections, histoplasmosis, listeriosis, coccidioidomycosis, pneumocystosis, aspergillosis) despite infection resolution, or otherwise recurrent infections of abnormal frequency, or prolonged infections suggesting an immune-compromised status, as judged by the investigator; (17) Known history of human immunodeficiency virus (HIV) infection; (18) Positive or indeterminate hepatitis B surface antigen (HBsAg) or hepatitis C antibody at screening; (19) Elevated transaminases (alanine aminotransferase [ALT] and/or aspartate aminotransferase [AST]) more than 3 times the upper limit of normal (>3× upper limit of normal [ULN]) at screening; (20) History of malignancy within 5 years prior to screening, except completely treated in situ carcinoma of the cervix and completely treated and resolved non-metastatic squamous or basal cell carcinoma of the skin; (21) History of patient-reported alcohol or drug abuse within 6 months prior to screening; (22) Any other medical or psychological condition including relevant laboratory abnormalities at screening that, in the opinion of the investigator, suggest a new and/or insufficiently understood disease, may present an unreasonable risk to the study patient as a result of his/her participation in this clinical trial, may make patient's participation unreliable, or may interfere with study assessments. The specific justification for patients excluded under this criterion will be noted in study documents (chart notes, case report form [CRF], etc.); (23) Severe concomitant illness(es) that, in the investigator's judgment, would adversely affect the patient's participation in the study; (24) Planned or anticipated use of any prohibited medications and procedures (see below) during study treatment; (25) Treatment with a live (attenuated) vaccine within 3 months prior to screening; (26) Patient or his/her immediate family is a member of the investigational team; (27) Pregnant or breast-feeding women, or women planning to become pregnant or breastfeed during the study; (28) Women unwilling to use adequate birth control, if of reproductive potential* and sexually active.

Study Treatments

Investigational drug: Dupilumab SC, a loading dose of 600 mg on day 1 followed by weekly doses of 300 mg from week 1 to week 11

Placebo: Placebo (same formulation as dupilumab without the active substance, anti-IL-4R monoclonal antibody) SC, a volume matching the dupilumab loading dose on day 1 followed by weekly doses matching the volume of dupilumab weekly dose from week 1 to week 11.

Patients received SC dupilumab 300 mg or matching placebo qw during the 12-week double-blind treatment phase. Patients received 2 injections (300-mg initial dose, followed by a 300-mg loading dose) on day 1, followed by weekly injections.

Permitted (Concomitant) Medications

Treatment with concomitant medications was permitted during the study. This included treatment with contraceptives, stable dose of proton pump inhibitors (PPIs) (patients who were using PPIs at screening did not discontinue or change the dosing regimen prior to end of treatment [EOT] visit); stable dose (for at least 3 months prior to screening) of systemic leukotriene inhibitors, topical, nasal, and/or inhaled corticosteroids; oral antihistamines for any duration; and oral antibiotics for up to 2 weeks.

Restricted Medications and Procedures

Restricted medications during duration of study included: (1) Medications used for the treatment of EoE (these were considered rescue medications): Swallowed topical corticosteroids, Systemic corticosteroids, Start or dose change of systemic leukotriene inhibitors, topical, nasal, and/or inhaled corticosteroids, and Systemic treatment for EoE with an immunosuppressive/immunomodulating substance (including, but not limited to, omalizumab, cyclosporine, mycophenolate-mofetil, azathioprine, methotrexate, IFN-γ, or other biologics); (2) Allergen immunotherapy (SCIT and SLIT were allowed if dose was stable for 1 year or more; however, OIT was prohibited); (3) Patients who were not using PPI in the 8 weeks prior to screening were prohibited from starting PPI therapy prior to EOT visit; (4) Treatment with a live (attenuated) vaccine (Chickenpox (varicella), FluMist-Influenza, Intranasal influenza, Measles (rubeola), Measles-mumps-rubella combination, Measles-mumps-rubella-varicella combination, Mumps, Oral polio (Sabin), Oral typhoid, Rubella, Smallpox (vaccinia), Yellow fever, Bacille Calmette-Guerin, Varicella zoster (shingles), Rotavirus); and (5) Treatment with an investigational drug (other than dupilumab)

The following concomitant procedures were prohibited during study treatment (through week 12): (1) Major elective surgical procedures; (2) Esophageal dilation (considered rescue procedure); and (3) Diet change (patients were to remain on stable diet for at least 6 weeks prior to screening and during the course of the study; stable diet was defined as no initiation of single or multiple elimination diets or reintroduction of previously eliminated food groups).

Study Endpoints

The primary efficacy endpoint was: Change in the Straumann Dysphagia Instrument (SDI) patient-reported outcome (PRO) score from baseline to week 10.

The secondary endpoints were: Percent change in weekly Eosinophilic Esophagitis Activity Index (EEsAI) PRO score from baseline to week 10; Change in weekly EEsAI PRO score from baseline to week 10; Percent change in weekly EEsAI PRO score from baseline to week 12; Change in weekly EEsAI PRO score from baseline to week 12; Percent change in the SDI PRO score from baseline to week 10; Percent change in the SDI PRO score from baseline to week 12; Change in the SDI PRO score from baseline to week 12; Change in Adult Eosinophilic Esophagitis Quality of Life (EoE-QOL-A) (questionnaire) PRO score from baseline to week 12; Percentage of patients with SDI PRO response at week 10; where response is defined as a decrease of at least 3 points on the SDI compared to baseline; Percentage of patients who achieve ≥40% improvement in EEsAI score from baseline to week 10; Percent change in overall peak esophageal intraepithelial eos/hpf (400×) from baseline to week 12; Change in Eosinophilic Esophagitis-Endoscopic Reference Score (EoE-EREFs) (endoscopy visual anatomical score) from baseline to week 12; Percentage of patients with use of rescue medication or procedure (e.g., esophageal dilation) through week 12; and Incidence of treatment-emergent adverse events (TEAEs)

The exploratory efficacy endpoints were: Change in mean esophageal intraepithelial eosinophil counts (eos/hpf) [calculated using peak count from each esophageal site] from baseline to week 12; Proportion of patients who achieve esophageal intraepithelial eosinophil count <1 eos/hpf at week 12; Change in Collins Histology Score from baseline to week 12; and Change in esophageal distensibility plateau as measured by functional lumen imaging from baseline to week 12.

Procedures and Assessments

Screening/Baseline procedures: The following procedures were performed only at the screening and/or baseline visit for the sole purpose of determining study eligibility or characterizing the baseline population: serum FSH (for confirmation of menopausal status), serum total IgE, HBsAg, and hepatitis C antibody.

Efficacy procedures: Efficacy was assessed during the study at specified clinic visits using patient-reported outcomes (PROs), including Straumann Dysphagia Instrument (SDI), Eosinophilic Esophagitis Activity Index (EEsAI), and the Eosinophilic Esophagitis Quality of Life (EoE-QOL-A) questionnaire, as well as esophageal biopsies and photographs (endoscopy procedure). Measurement of inflammatory and remodeling esophageal features based on the Eosinophilic Esophagitis Edema rings Exudates Furrows and Strictures (EoE-EREFS) score was included as part of the endoscopy procedure. The endolumenal functional lumen imaging probe (EndoFLIP) procedure to measure esophageal distensibility was performed during the endoscopy procedures. The EoE Histological Scoring System (HSS) was used to measure 8 histologic features of EoE.

Straumann Dysphagia Instrument—Patient-reported Outcome

The SDI is a non-validated PRO that has been used in clinical studies to determine the frequency and intensity of dysphagia (Straumann 2010). The SDI has a 1-week recall period. Frequency of dysphagia events is graded on a 5-point scale: 0=none, 1=once per week, 2=several times per week, 3=once per day, and 4=several times per day, and intensity of dysphagia events is graded on a 6-point scale: 0=swallowing unrestricted, 1=slight sensation of resistance, 2=slight retching with delayed passage, 3=short period of obstruction necessitating intervention (e.g., drinking, breathing), 4=longer-lasting period obstruction only removable by vomiting, and 5=long-lasting complete obstruction requiring endoscopic intervention. The total SDI score ranges from 0 to 9. In the Straumann study, a clinical response (improvement) was defined as a decrease in SDI score of at least 3 points from baseline.

This assessment was completed by the patient electronically weekly in a questionnaire from the beginning of screening through end of study or early termination. Items utilized to quantitate the SDI were included in the EEsAI/SDI.

Eosinophilic Esophagitis Activity Index—Patient-reported Outcome

The EEsAI is a non-validated, multimodular index in development at University Hospital Inselspital (Berne, Switzerland) (Schoepfer 2014), a part of the international EEsAI study group. The EEsAI PRO module (questionnaire) used in this study includes items related to the intensity and frequency of dysphagia, the influence of specific food groups on dysphagia symptoms, and other symptoms independent of eating or drinking (i.e., heartburn, acid regurgitation, and chest pain). The total EEsAI PRO score ranges from 0 to 100 (FIG. 1), wherein higher scores indicate worse symptoms. The score consists of 5 parts: frequency of trouble swallowing, duration of trouble swallowing, pain when swallowing, visual dysphagia question, and avoidance, modification and slow eating (AMS). The EEsAI PRO utilizes 24-hour and 1-week recall periods.

This assessment was completed by the patient electronically daily and weekly in a questionnaire from the beginning of screening through end of study or early termination.

Adult Eosinophilic Esophagitis Quality of Life Questionnaire—Patient-reported Outcome The EoE-QOL-A questionnaire is a validated disease-specific measure of health-related quality of life in EoE patients (Taft 2011). The instrument used in this study, the EoE-QOL-A v.3.0, includes 30 items related to established domains such as social functioning, emotional functioning, and disease impact of daily life experiences. The EoE-QOL-A has a 1-week recall period. The items are graded on a 5-point scale: 'Not at All,' 'Slightly,' 'Moderately,' 'Quite a bit,' and 'Extremely'.

This assessment was recorded by the patient in a questionnaire at baseline and then monthly through end of study or early termination.

Endoscopy with Esophageal Biopsies and Photographs

Esophageal biopsies were obtained by endoscopy at the screening and week 12 visits. The screening endoscopy was performed during the screening period to allow results to be available prior to day-1 for assessment of eligibility. A total of 9 mucosal pinch biopsies were collected at each time point from 3 esophageal regions: 3 proximal, 3 mid, and 3 distal. Two samples from each region were used for the histology (needed for study inclusion criteria, as well as secondary endpoint). To participate in the study, patients had to have a peak intraepithelial eosinophil count eos/hpf (400×) in at least 2 of the 3 esophageal regions sampled. Change in peak esophageal eos/hpf (400×) from baseline to week 12 was a secondary endpoint; this was determined by counting eosinophils in the most inflamed areas of each esophageal region sampled at each time point and calculating the change in the peak count at each site obtained at baseline compared to the count obtained at week 12. As an exploratory objective, the change in the mean of all 3 peak counts, i.e., the peak count at each of the 3 esophageal regions for each patient at each time point (screening and week 12) was calculated. Tissue blocks remaining after the histological assessment were banked for exploratory research.

The EoE-EREFS (edema, rings, exudates, furrows, strictures) was used to measure the endoscopically identified EoE esophageal mucosal inflammatory and remodeling features. This instrument includes a total of 17 items related to the presence and severity of esophageal features. The specific esophageal features include: rings (concentric rings around esophagus—absent, mild, moderate, severe, not applicable); strictures (narrowing of the esophagus—yes, no, not applicable); diameter of the stricture (if applicable); exudates (refer to white plaques—absent, mild, severe), furrows (vertical lines down the esophagus—absent, present); edema (loss of vascular markings of the mucosa—absent, present); crêpe paper esophagus (absent, present); overall general appearance incorporating all endoscopically identified EoE findings (i.e., fixed rings, strictures, whitish exudates, furrowing, edema, and crêpe paper mucosa). In addition, mucosal changes associated with gastroesophageal reflux disease were also recorded using the Los Angeles classification system for erosions (No Erosions or LA Classification A, B, C, D). The EoE esophageal characteristics were analyzed based on the EoE-EREFS, a validated scoring system for inflammatory and remodeling features of disease using both overall scores and scores for each individual characteristic (Hirano 2014). The modified EREFS score in this study was based on a total score range of 0-8; wherein higher scores indicate greater impairment. Each score comprised: Edema: 0-1; Rings: 0-3; Exudates: 0-2; Furrows: 0-1; and Strictures: 0-1 to give a total possible score of 8.

The assessment of esophageal distensibility utilizing the endolumenal functional lumen imaging probe (EndoFLIP, Crospon, Ireland) was also performed to measure the diameter of the esophageal lumen and pressure (e.g., esophageal rigidity), with measurements taken as part of the endoscopy procedure performed at screening and week 12. The EndoFLIP device is a catheter based procedure that measures the cross sectional area at multiple sites along the esophagus with simultaneous intraluminal pressure recordings during volumetric distension of the esophagus. The analyses of cross sectional area versus pressure relationships of the esophagus allow for determination of esophageal compliance as well as the distensibility plateau (DP). The DP has been shown to be significantly reduced in patients with EoE compared to healthy controls (Kwiatek 2011). Moreover, the esophageal distensibility has been associated with outcomes of both food impaction and need for esophageal dilation (Nicodème 2013).

The EoE-HSS generated separate severity (grade) and extent (stage) disease scores. The score was used to measure 8 histologic features (parameters) of EoE from 3 different regions (proximal, mid and distal) of the esophagus (Collins, et al. 2017). The 8 parameters include: eosinophil density, basal zone hyperplasia, eosinophil abscesses, eosinophil surface layering, dilated intercellular spaces, surface epithelial alteration, dyskeratotic cells, and lamina propria fibrosis. A scale of 0-3 was used for each parameter, both grade and stage (0 being least inflamed, normal). Total score range for each region for this study was 0-21 (excluding lamina propria parameter). The lamina propria assessment was excluded given that 50% of pinch biopsies would not be deep enough for lamina propria assessment. Total score per patient was calculated as (0-21 score×3 regions=total possible score of 63 per time point). Two scores were generated per patient per time point, one each for grade (severity) and stage (extent).

Photographs were taken by the site as part of the endoscopic procedure and biopsy collection.

Safety Procedures: An AE is any untoward medical occurrence in a patient administered a study drug, which may or may not have a causal relationship with the study drug. Therefore, an AE is any unfavorable and unintended sign (including abnormal laboratory finding), symptom, or disease that is temporally associated with the use of a study drug, whether or not considered related to the study drug. An AE also includes any worsening (i.e., any clinically significant change in frequency and/or intensity) of a pre-existing condition that is temporally associated with the use of the study drug.

A serious adverse event (SAE) is any untoward medical occurrence that at any dose results in death, is life-threatening, requires in-patient hospitalization, results in persistent or significant disability/incapacity, is a congenital anomaly/birth defect and/or is an important medical event (e.g., such as an event may jeopardize the patient or may require intervention to prevent 1 of the other serious outcomes listed above.

Safety and tolerability was assessed by physical examinations, vital signs, electrocardiograms (ECGs), clinical laboratory tests, and clinical evaluations. Patients were asked to monitor all AEs experienced from the time of informed consent until their last study visit.

Pharmacokinetic and Antibody Procedures: Serum samples were collected for assay of dupilumab level and PK parameters were calculated using the dupilumab concentration data. Serum samples were collected for assay of ADA, and exploratory analyses.

Results

Baseline Characteristics: Patients were randomized in a 1:1 ratio to receive a subcutaneous (SC) 600 mg dupilumab or SC placebo loading dose followed by weekly SC 300 mg dupilumab or SC placebo during the 12-week double-blind treatment phase. The randomization was stratified by baseline Straumann Dysphagia Instrument (SDI) PRO score (≥5 and ≤7 versus >7). Baseline demographic and disease characteristics were generally balanced between the two groups (Tables 1-2), except for mean total IgE (dupilumab 217.8 kU/L; placebo 468.2 kU/L).

TABLE 1

Summary of Baseline Demographic Characteristics

|  | Placebo (N = 24) | 300 mg dupilumab qw (N=23) |
|---|---|---|
| Age, mean (SD), years | 36.1 (12.75) | 33.1 (8.70( |
| Age Group, n (%) |  |  |
| ≥18 to <40 years | 15 (62.5%) | 16 (69.6%) |
| ≥40 to <65 years | 9 (37.5%) | 7 (30.4%) |
| ≥65 years | 0 | 0 |
| Male sex, n (%) | 10 (41.7%) | 13 (56.5%) |
| Race: White, n (%) | 21 (87.5%) | 23 (100%) |
| BMI (mean kg/m$^2$) | 30.0 | 27.7 |

TABLE 2

Summary of Baseline Disease Characteristics

|  | Placebo (N = 24) | 300 mg dupilumab qw (N = 23) |
|---|---|---|
| Age at EoE onset, n (%) |  |  |
| 0 to 18 years | 4 (16.7%) | 7 (13.0%) |
| 19 to 24 years | 5 (20.8%) | 10 (21.7%) |
| 25 to 50 years | 13 (54.2%) | 28 (65.2%) |
| >50 years | 2 (8.3%) | 0 |
| Duration of EoE years | 5.0 | 3.6 |
| Blood Eosinophils (SD) GI/L | 0.43 (0.3) | 0.31 (0.2) |
| Mean total IgE (SD) kU/L | 486.2 (900.7) | 217.8 (288.8) |
| Mean SDI score (SD), (0-9) | 6.4 (1.0) | 6.4 (1.0) |
| Weekly EEsAI score (0-100) | 62.2 | 62.0 |
| Mean overall peak eosinophils/hpf (SD) | 101.1 (57.1) | 102.1 (53.5) |
| EoE Histology Scoring System (0-63) | 27.4 | 27.9 |
| # of dysphagia/week between screening and baseline | 12.4 | 13.7 |
| EREF endoscopy score (0-9) | 4.3 | 3.9 |
| Prior treatment with high dose PPIs, n (%) | 24 (100%) | 23 (100%) |
| Prior topical corticosteroid use, n (%) | 20 (83.3) | 18 (78.3) |
| Prior dilation, n (%) | 10 (41.7) | 11 (47.8) |
| Number of prior esophageal dilations (SD) | 3.9 (3.3) | 5.7 (8.0) |
| Any comorbid disease, n (%) | 19 (79.2) | 20 (87.0) |

Both groups showed a high level of atopic disease (Table 3).

TABLE 3

Summary of EoE/Allergic Disease Personal History

|  | Placebo (N = 24) | 300 mg dupilumab qw (N = 23) |
|---|---|---|
| Patients with at least one Personal History | 24 (100%) | 23 (100%) |
| Food allergy | 17 (70.8%) | 14 (60.9%) |
| Allergic rhinitis | 15 (62.5%) | 16 (69.6%) |
| Other allergies (medications, animals, plants, mold, dust mites, etc.) | 12 (50.0%) | 14 (60.9%) |
| Asthma | 9 (37.5%) | 11 (47.8%) |
| Chronic sinusitis | 8 (33.3%) | 2 (8.7%) |
| Hives | 6 (25.0%) | 7 (30.4%) |
| Atopic Dermatitis | 5 (20.8%) | 3 (13.0%) |
| Allergic conjunctivitis | 3 (12.5%) | 3 (13.0%) |

Efficacy Results: Table 4 summarizes the primary and secondary endpoint results. Dupilumab significantly improved subjective measures of EoE as reflected by dysphagia, as well as objective histologic and endoscopic measures of disease in EoE, compared with placebo. No patients received rescue medication/procedure during the 12-week double-blind treatment period.

TABLE 4

Results-Primary and Secondary Endpoints*

| Endpoint | Placebo[1] (N = 24) | 300 mg dupilumab qw[1] (N = 23) | LS mean difference vs placebo (95% CI) | P-value** |
|---|---|---|---|---|
| Primary Efficacy Endpoint | | | | |
| Change of the SDI score from baseline to week 10 (range 0-9) | N = 14<br>−1.3 (0.6) | N = 17<br>−3.0 (0.5) | −1.7 (−3.22, −0.16) | 0.0304 |
| Secondary Efficacy Endpoint | | | | |
| % Change of weekly EEsAI score from baseline to week 10 (range 0-100) | N = 13<br>−11.3 (9.9) | n-17<br>−34.6 (9.1) | −23.2 (−49.68, 3.21) | 0.0850 |
| Change of weekly EEsAI score from baseline to week 10 (range 0-100) | N = 13<br>−9.0 (5.6) | N = 17<br>−22.9 (5.0) | −13.9 (−28.54, 0.78) | 0.0635 |
| % Change of weekly EEsAI score from baseline to week 12 (range 0-100) | N = 8<br>−3.3 (12.7) | N = 15<br>−37.0 (11.2) | −33.6 (−68.83, 1.54) | 0.0608 |
| Change of weekly EEsAI score from baseline to week 12 (range 0-100) | N = 8<br>−5.0 (7.1) | N = 15<br>−26.1 (5.9) | −21.1 (−40.42, −1.86) | 0.0318 |
| % Change of the SDI score from baseline to week 10 (range 0-9) | N = 14<br>−18.6 (9.0) | N = 17<br>−45.0 98.4) | −26.5 (−50.52, −2.39) | 0.0312 |
| Change of the SDI score from baseline to week 12 (range 0-9) | N = 9<br>−2.2 (0.7) | N = 16<br>−2.9 (0.6) | −0.8 (−2.48, 0.96) | 0.3830 |
| % Change of the SDI score from baseline to week 12 (range 0-9) | N = 9<br>−31.8 (10.7) | N = 16<br>−42.8 (8.6) | −11.0 (−37.46, 15.47) | 0.4147 |
| Change of EoE-QOL-A PRO total score from baseline to week 12 (range 1-5) | N = 21<br>0.47 (0.14) | N = 23<br>0.80 (0.14) | 0.33 (−0.05, 0.72) | 0.0910 |
| Proportion of patients with decrease of at least 3 points on the SDI from baseline to week 10 | N = 14<br>3 (12.5%) | N = 17<br>9 (39.1%) | 26.6 (−3.04, 51.05) | 0.049 |
| Proportion of patients that achieve ≥40% improvement in EEsAI PRO score from baseline to week 10 | N = 13<br>2 (8.3%) | N = 17<br>6 (26.1%) | 17.8 (−11.54, 43.55) | 0.1365 |
| % Change of overall peak esophageal intraepithelial eosinophils/high power field (eos/hpf) (400X) from baseline to week 12 | N = 22<br>15.1 (12.5) | N = 22<br>−91.8 (12.3) | −107 (−141.4, −72.46) | <0.0001 |
| Change of EoE-EREFS total score (endoscopy visual anatomical score) from baseline to week 12 (range 0-9) | N = 22<br>−0.3 (0.33) | N = 22<br>−1.9 (0.32) | −1.6 (−2.50, −0.68) | 0.0006 |

Figure 3:
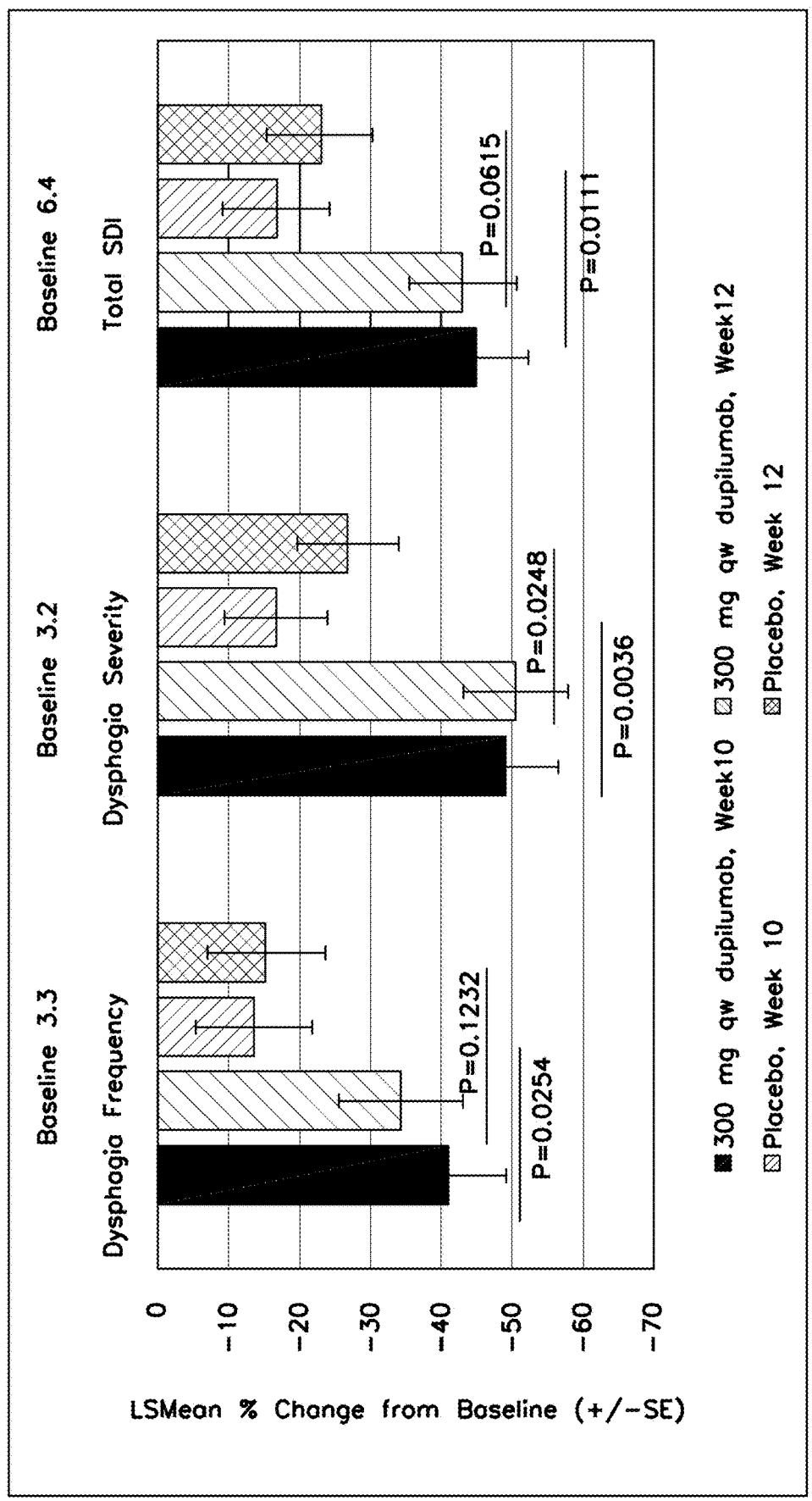
FIG. 3 shows mean percent change from baseline in dysphagia frequency and severity components of the Straumann Dysphagia Instrument (SDI) score at week 10 and week 12 upon administration of once-a-week (qw) 300 mg dupilumab vs placebo.

[1]n represents # of patients with both baseline and post-baseline actual observed values
*For continuous variables, multiple imputation/ANCOVA was used, LS (SE) was presented; for binary variables, patients with missing data were treated as non-responders and Fisher exact test was used for comparison, number and % of responder was presented.
**For the secondary endpoints, all p-values were nominal Dupilumab improved Straumann Dysphagia Instrument (SDI) score compared to placebo (−3 vs. −1.3, P=0.0304; 45.05% vs. 18.59%, P=0.0312) at week 10 (Table 4, FIG. 2). 39% of dupilumab-treated patients achieved ≥3 reduction in SDI compared to 12.5% in the placebo group at week 10. At both week 10 and week 12, dupilumab improved both frequency and severity components of dysphagia of the SDI score (FIG. 3).

Figure 4:
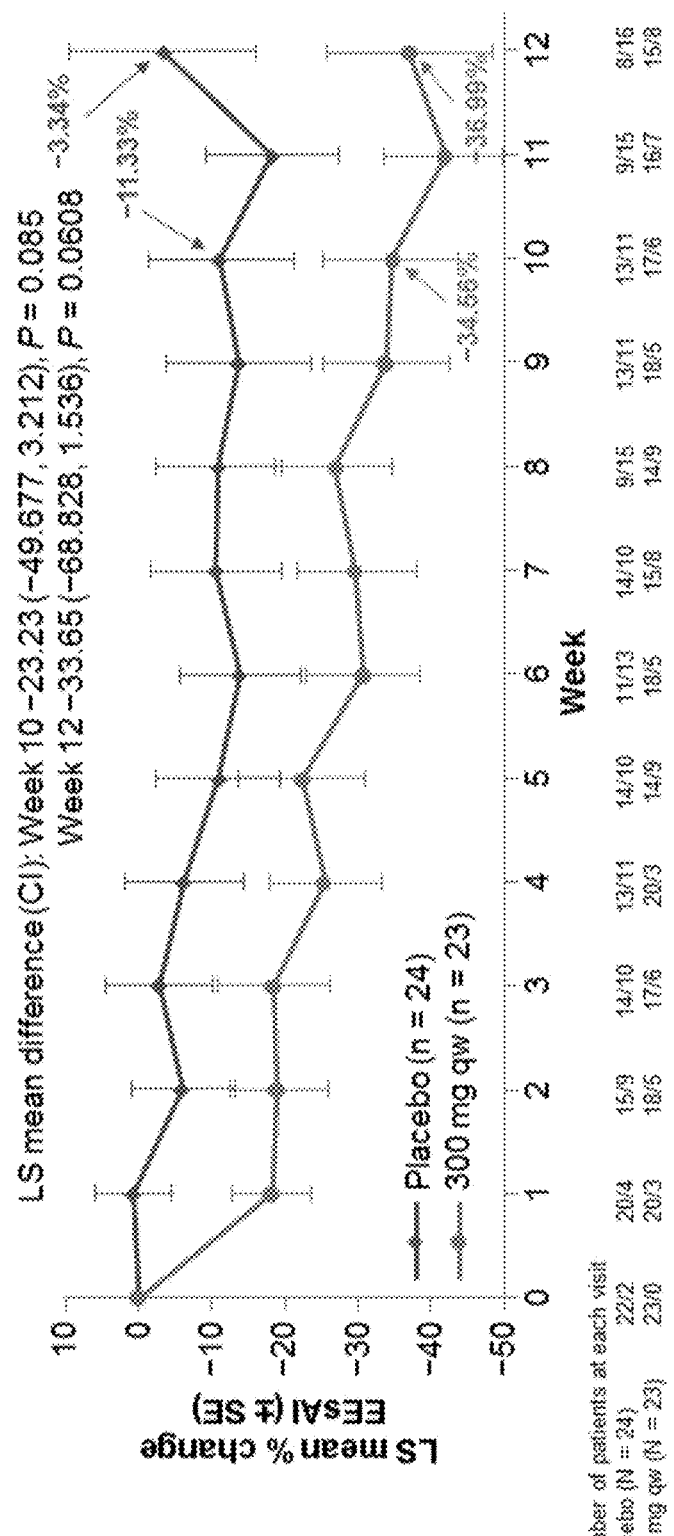
FIG. 4 shows the mean percent change from baseline in EEsAI score during the 12-week treatment period in patients administered once-a-week (qw) 300 mg dupilumab vs placebo.

Dupilumab numerically reduced EEsAI score (−34.6% vs. −11.3%, P=0.085) vs placebo through week 10 (Table 4, FIG. 4).

Dupilumab significantly reduced peak eosinophil count (eos/hpf) from baseline to week 12, compared to placebo [−94.1 (−91.8%) vs −7.4 (+15.1%), P<0.0001] (Tables 4 and 6). A reduction in eosinophil tissue infiltration was observed in all patients in the dupilumab group (Table 5). The dupilumab effect was similar on the proximal, mid and distal regions of the esophagus.

TABLE 5

Responder Analysis

| Peak Eos (eos/hpf) at week 12 | Proportion of patients with response at week 12, n (%) | | |
|---|---|---|---|
| | 300 mg dupilumab | Placebo | P value |
| <1 | 3 (13) | 0 (0) | 0.1092 |
| <6 | 14 (60.9) | 0 (0) | <0.0001 |
| <15 | 18 (78.3) | 0 (0) | <0.0001 |

Figure 5:
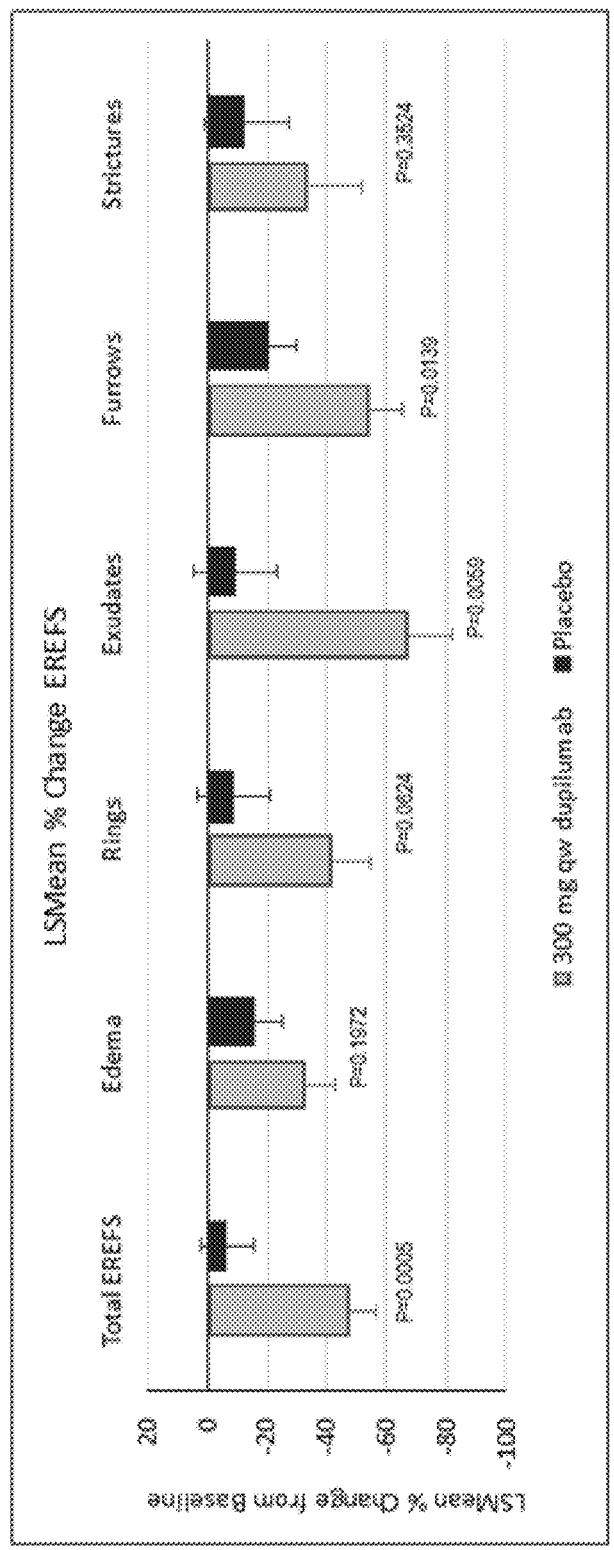
FIG. 5 shows mean percent change from baseline in total EoE Edema Rings Exudates Furrows and Strictures (EREFS) score as well as in the subcomponents of the EREFS score at week 12 in patients administered once-a-week (qw) 300 mg dupilumab vs placebo.

Dupilumab significantly reduced EREFS relative to placebo at week 12 (LS mean change p=0.0006, LS mean % change p=0.0004) (Table 4). Dupilumab significantly reduced the total EREFS score, as well as the exudates and furrows subcomponents with trends observed for the edema, rings and strictures subcomponents (FIG. 5).

Figure 6:
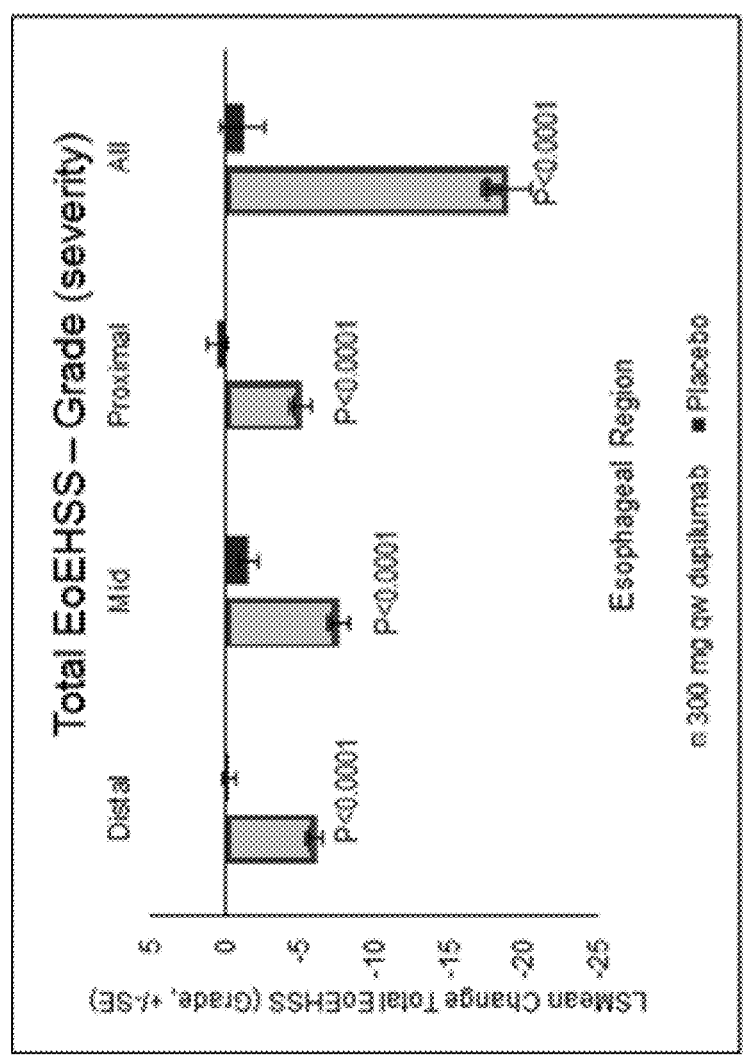
FIG. 6 shows mean change from baseline in total EoE Histology Scoring System (HSS) score for the grade (severity) subcomponent at week 12 in patients administered once-a-week (qw) 300 mg dupilumab vs placebo.
Figure 7:
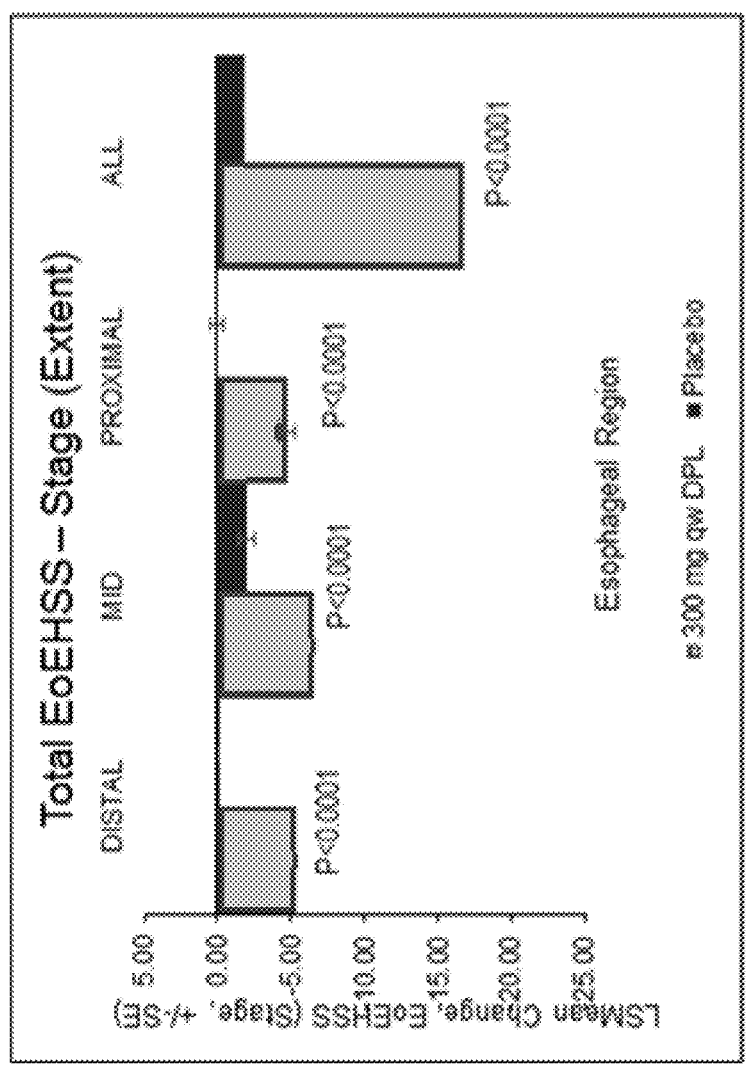
FIG. 7 shows mean change from baseline in total EoE HSS score for the stage (extent) subcomponent at week 12 in patients administered once-a-week (qw) 300 mg dupilumab vs placebo.
Figure 9:
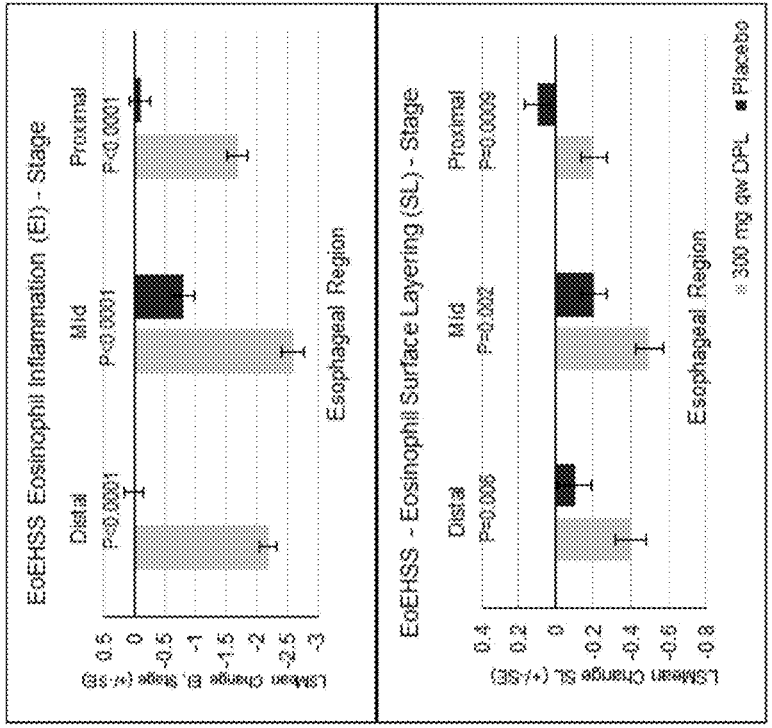
FIG. 9 is made up of FIGS. 9A, 9B, 9C, and 9D.
Figure 9:
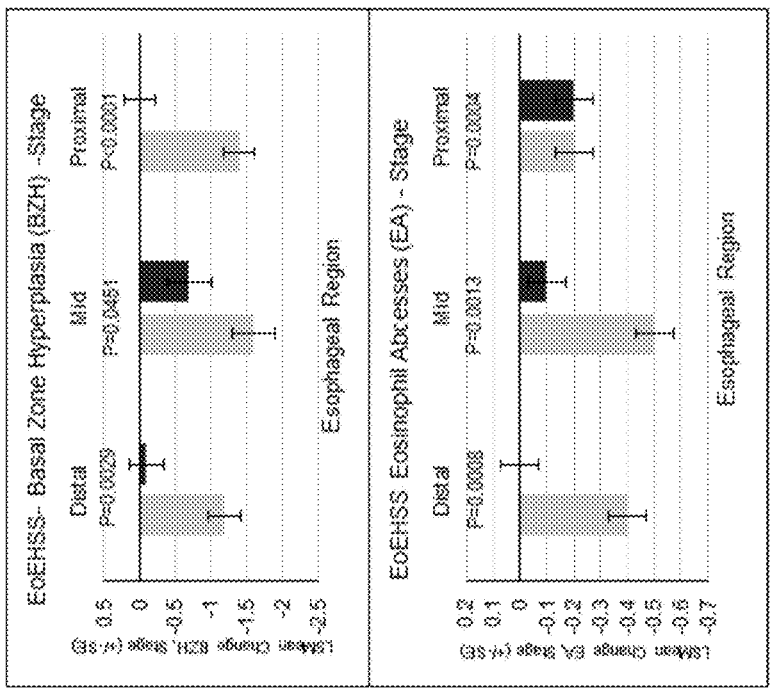
Figure 10:
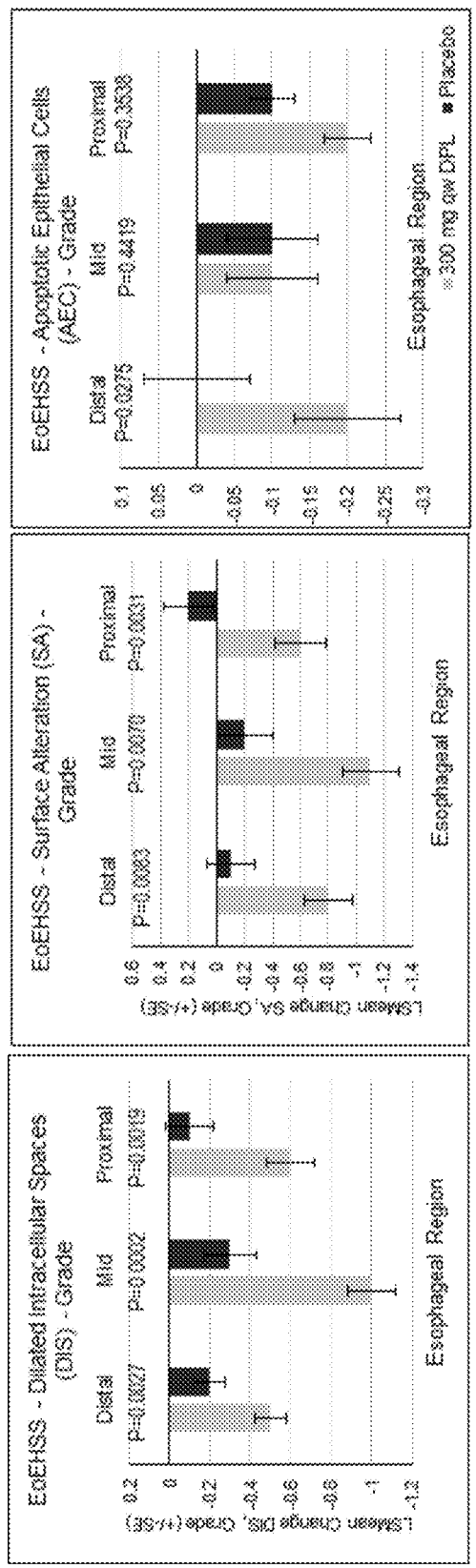
FIG. 10 is made up of FIGS. 10A, 10B, and 10C.
Figure 11:
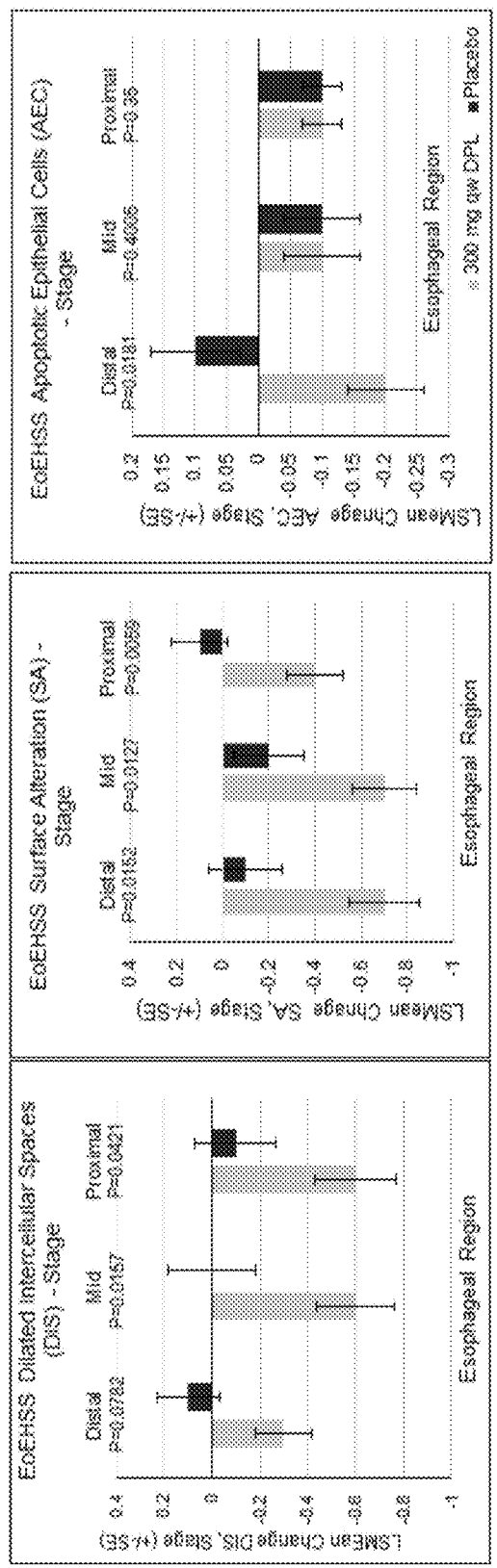
FIG. 11 is made up of FIGS. 11A, 11B, and 11C.

Dupilumab significantly reduced both the total grade and stage scores of the EoE-HSS from baseline to week 12, compared to placebo (P<0.001 vs placebo) (Table 6; FIGS. 6 and 7). Dupilumab significantly reduced both grade (severity) and stage (extent) scores for basal zone hyperplasia (BZH), eosinophil inflammation (EI), eosinophil surface layering (SL) and eosinophil abscess (EA) in proximal, mid and distal regions (FIGS. 8 and 9). Also, dupilumab reduced grade and stage scores for dilated intracellular spaces and surface alteration in all regions and distal apoptotic epithelial cells (FIGS. 10 and 11).

Figure 12:
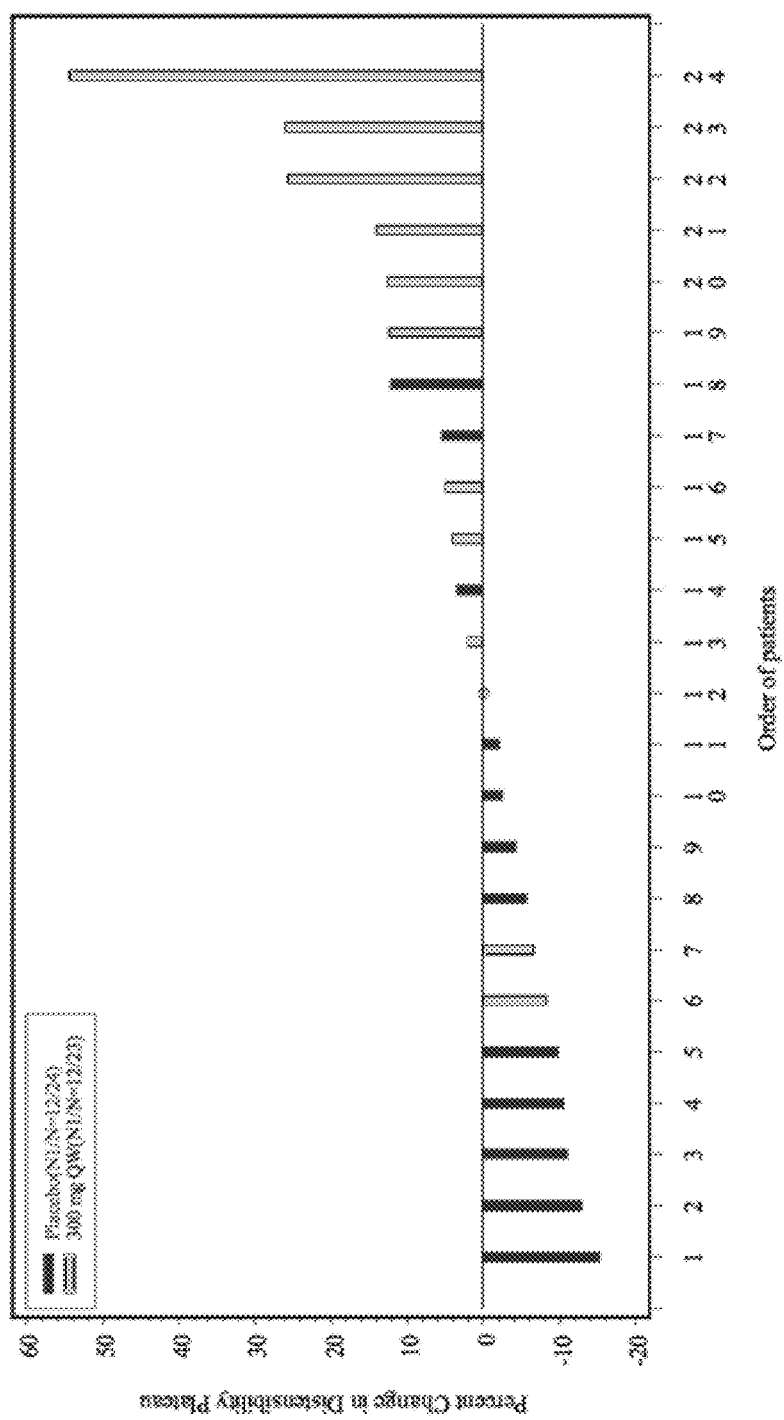
FIG. 12 shows percent change from baseline in distensibility plateau at week 12 in patients administered once-a-week (qw) 300 mg dupilumab vs placebo

Dupilumab significantly improved esophageal distensibility at week 12 compared to placebo (Table 6). An increase (improvement) in distensibility plateau was observed in more patients treated with dupilumab than placebo (FIG. 12).

Table 6 summarizes the effect of dupilumab on subjective patient-reported outcomes on dysphagia and on clinician-assessed objective measures.

TABLE 6

Efficacy of dupilumab on subjective and objective EoE measures

|  | PBO (N = 24) | Dupilumab 300 mg qw (N = 23) | LS mean difference vs PBO (95% CI) |
|---|---|---|---|
| SDI score | | | |
| BL score, mean (± SD) | 6.4 (1.01) | 6.4 (1.04) | |
| Week 10 | n = 14 | n = 17 | |
| LS mean % change from BL (± SE) | −1.3 (0.6) | −3.0 (0.5) | −1.7 (−3.2, −0.2)* |
| EEsAI score | | | |
| BL score, mean (± SD) | 62.2 (16.45) | 62.0 (18.36) | |
| Week 10 | n =13 | n =17 | |
| LS mean % change from BL (± SE) | −11.3 (9.9) | −34.6 (9.1) | −23.2 (−49.7, 3.2)# |
| Peak esophageal intraepithelial | | | |
| (eos/hpf) | | | |
| BL score, mean (± SD) | 101.1 (57.1) | 102.1 (53.5) | |
| Week 12 | n = 22 | n = 22 | |
| LS mean change from BL (± SE) | −7.4 (9.61) | −94.1 (9.52) | |
| LS mean % change from BL (± SE) | 15.1 ( 12.5) | −91.8 ( 12.3) | −106.9 (−141.4, −72.5)*** |
| Pts with response <6 eos/hpf, n (%) | 0.0 | 14 (60.9) | |
| Pts with response <15 eos/hpf, n (%) | 0.0 | 18 (78.3) | |
| EoE-EREFS score | | | |
| BL score, mean (± SD) | 4.3 (1.46) | 3.9 (1.87) | |
| Week 12 | n = 22 | n = 23 | |
| LS mean change from BL (± SE) | −0.3 (0.3) | −1. 9 (0.3) | −1.6 (−2.5, −0.7)*** |
| EoE-HSS | | | |
| BL score, mean (± SD) | 27.4 (6.46) | 27.9 (6.05) | |
| Total-grade (severity) score | | | |
| Week 12 | n = 20 | n = 21 | |
| All LS mean % change from BL (± SE) | 3.9 (6.6) | −64.2 (6.4) | −68.1 (−85.8, −50.3)*** |
| Distal LS mean % change from BL (± SE) | 2.7 (5.3) | −57.0 (5.3) | −59.7 (−74.3, −45.1)*** |
| Mid LS mean % change from BL (± SE) | −8.1 (7.0) | −70.8 (6.8) | −62.7 (−81.7, −43.7)*** |
| Proximal LS mean % change from BL (± SE) | 66.1 (27.4) | −50.2 (24.5) | −116.3 (−188.0, −44.5)*** |
| Total-stage (extent) score | | | |
| Week 12 | n = 20 | n = 21 | |
| All LS mean % change from BL (± SE) | −3.5 (5.0) | −58.1 (4.7) | −54.6 (−68.1, −41.0)*** |
| Distal LS mean % change from BL (± SE) | 5.1 (6.3) | −50.6 (6.3) | −55.6 (−73.2, −38.1)*** |
| Mid LS mean % change from BL (± SE) | −18.4 (5.7) | −62.0 (5.5) | −43.5 (−59.1, −28.0)*** |
| Proximal LS mean % change from BL (± SE) | 43.1 (21.6) | −46.9 (19.2) | −90.0 (−146.5, −33.5)*** |

TABLE 6-continued

Efficacy of dupilumab on subjective and objective EoE measures

|  | PBO (N = 24) | Dupilumab 300 mg qw (N = 23) | LS mean difference vs PBO (95% CI) |
|---|---|---|---|
| Distensibility plateau (mm) |  |  |  |
| BL, mean (± SD) | 17.60 (2.879) | 18.66 (3.799) |  |
| Week 12 | n = 12 | n = 12 |  |
| LS mean % change from BL (± SE) | −6.2 (2.7) | 11.8 (2.7) | 18.0 (10.9, 25.2)*** |

*P < 0.05,
***P < 0.001,
# = P = 0.085 bs PBO. SDI is a 9-item measure of dysphagia; score range 0-9 with higher scores indicating worse symptoms. EEsAI is a 5-item measure of dysphagia; score range 0-100 with higher scores indicating worse symptoms. The EoE Histology scoring system (EoEHSS) measures eosinophil density, basal zone hyperplasia, eosinophil abscesses, eosinophil surfacing layering, surface epithelial alteration, dyskeratotic epithelial cells and dilated intercelluar spaces. Lamina propria was excluded from the analysis, as ~50% of pinch biopsies were not deep enough for assessment. Esophageal distensibility plateau is measured using the Functional Lumen Imaging Probe (EndoFLIP, ® Crospon), a prob using impedance planimetry. The continuous efficacy end points were analyzed in the full analysis et (FAS) using multiple imputation (MI), followed by an analysis of covariance (ANCOVA) model with treatment group as fixed effect, and baseline SDI and the relevant baseline value as covariates. LS, least-squares; qw, every week Safety Results: Dupilumab was well tolerated in EoE patients. The most common treatment-emergent adverse events (TEAEs) were injection-site erythema (dupilumab 34.8%, placebo 8.3%) and nasopharyngitis (dupilumab 17.4%, placebo 4.2%).

Conclusion

Compared to placebo, dupilumab demonstrated a statistically significant reduction in the primary endpoint, change from baseline in Straumann Dysphagia Instrument (SDI) at week 10, the LS mean difference in change from baseline at week 10 between dupilumab and placebo groups was −1.7 (p=0.0304). Improvements in other subjective dysphagia measures including EEsAI (at week 10) and EOE-QOL (at week 12) were also noted. Finally, there were marked, statistical improvements in both histologic and visual endoscopic objective assessments of disease activity, including the percent change from baseline in peak eosinophils and absolute change from baseline in Eosinophilic Esophagitis Edema, Rings, Exudates, Furrows and Stricture (EoE-EREFS) score at week 12. Dupilumab treatment was generally safe and well tolerated. The most common TEAEs were mild ISRs and viral upper respiratory tract infections and nasopharyngitis.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

What is claimed is:

1. A method of increasing esophageal distensibility in a patient having eosinophilic esophagitis (EoE), the method comprising:
   (a) selecting a patient having EoE, who has a baseline of ≥15 eosinophils per high powered field (hpf) in the esophagus, wherein the patient has been treated previously with a proton pump inhibitor (PPI) and has had at least one prior esophageal dilation; and
   (b) administering to the patient a therapeutically effective amount of a pharmaceutical composition comprising an interleukin-4/interleukin-13 (IL-4/IL-13) pathway inhibitor, wherein the IL-4/IL-13 pathway inhibitor is an antibody or antigen-binding fragment thereof that binds IL-4Rα, wherein the antibody or antigen-binding fragment thereof comprises the heavy chain complementarity determining regions (HCDRs) of a heavy chain variable region (HCVR) comprising the amino acid sequence of SEQ ID NO: 1 and the light chain complementarity determining regions (LCDRs) of a light chain variable region (LCVR) comprising the amino acid sequence of SEQ ID NO: 2.

2. The method of claim 1, wherein the patient is ≥12 years of age.

3. The method of claim 2, wherein the patient is ≥18 years of age.

4. The method of claim 1, wherein the patient has a concurrent disease or condition selected from the group consisting of food allergy, allergic rhinitis, non-food allergy, asthma, chronic sinusitis, hives, atopic dermatitis, and allergic conjunctivitis.

5. The method of claim 1, wherein the patient has an elevated level of at least one biomarker selected from the group consisting of eotaxin-3, periostin, serum IgE (total and allergen-specific), IL-13, IL-5, serum thymus and activation regulated chemokine (TARC), thymic stromal lymphopoietin (TSLP), serum eosinophilic cationic protein (ECP), and eosinophil-derived neurotoxin (EDN).

6. The method of claim 1, wherein administration of the IL 4/IL-13 pathway inhibitor results in an increase of at least 10% from baseline in esophageal distensibility, as measured by a functional lumen imaging probe.

7. The method of claim 1, wherein the IL-4/IL-13 pathway inhibitor is administered at a dose of about 50 to about 600 mg.

8. The method of claim 1, wherein the IL-4/IL-13 pathway inhibitor is administered at a dose of about 300 mg.

9. The method of claim 8, wherein each dose is administered one week or two weeks after the immediately preceding dose.

10. The method of claim 1, wherein the IL-4/IL-13 pathway inhibitor is administered at an initial dose followed by one or more secondary doses, wherein each secondary dose is administered 1 to 4 weeks after the immediately preceding dose.

11. The method of claim 10, wherein the initial dose comprises 50-600 mg of the IL-4/IL-13 pathway inhibitor.

12. The method of claim 10, wherein each secondary dose comprises 25-400 mg of the IL-4/IL-13 pathway inhibitor.

13. The method of claim 10, wherein the initial dose comprises 600 mg of the IL-4/IL-13 pathway inhibitor, and each secondary dose comprises 300 mg of the IL-4/IL-13 pathway inhibitor.

14. The method of claim 13, wherein each secondary dose is administered one week or two weeks after the immediately preceding dose.

15. The method of claim 1, wherein the patient exhibits an allergic reaction to a food allergen contained in a food item selected from the group consisting of a dairy product, egg, wheat, soy, corn, fish, shellfish, peanut, a tree nut, beef, chicken, oat, barley, pork, green beans, apple and pineapple.

16. The method of claim 1, wherein the patient exhibits an allergic reaction to a non-food allergen derived from one of dust, pollen, mold, plant, cat, dog or insect.

17. The method of claim 1, wherein the IL-4/IL-13 pathway inhibitor is administered in combination with a second therapeutic agent or therapy, wherein the second therapeutic agent or therapy is selected from the group consisting of an IL-1beta inhibitor, an IL-5 inhibitor, an IL-9 inhibitor, an IL-13 inhibitor, an IL-17 inhibitor, an IL-25 inhibitor, a TNFalpha inhibitor, an eotaxin-3 inhibitor, an IgE inhibitor, a prostaglandin D2 inhibitor, an immunosuppressant, a topical corticosteroid, an oral corticosteroid, a systemic corticosteroid, an inhaled corticosteroid, a glucocorticoid, a proton pump inhibitor, a NSAID, esophagus dilation, allergen removal, and diet management.

18. The method of claim 1, wherein the antibody or antigen-binding fragment thereof comprises an HCDR1 comprising the amino acid sequence of SEQ ID NO: 3, an HCDR2 comprising the amino acid sequence of SEQ ID NO: 4, an HCDR3 comprising the amino acid sequence of SEQ ID NO: 5, an LCDR1 comprising the amino acid sequence of SEQ ID NO: 6, an LCDR2 comprising the amino acid sequence of SEQ ID NO: 7, and an LCDR3 comprising the amino acid sequence of SEQ ID NO: 8.

19. The method of claim 1, wherein the antibody or antigen-binding fragment thereof comprises an HCVR comprising the amino acid sequence of SEQ ID NO: 1, and an LCVR comprising the amino acid sequence of SEQ ID NO: 2.

20. The method of claim 1, wherein the antibody or antigen-binding fragment thereof comprises a heavy chain comprising the amino acid sequence of SEQ ID NO: 9 and a light chain comprising the amino acid sequence of SEQ ID NO: 10.

21. The method of claim 1, wherein the IL-4/IL-13 pathway inhibitor is dupilumab or a bioequivalent thereof.

22. The method of claim 1, wherein the IL-4/IL-13 pathway inhibitor is administered subcutaneously.

* * * * *

UNITED STATES PATENT AND TRADEMARK OFFICE
CERTIFICATE OF CORRECTION

| | | |
|---|---|---|
| PATENT NO. | : 11,053,309 B2 | Page 1 of 1 |
| APPLICATION NO. | : 16/054583 | |
| DATED | : July 6, 2021 | |
| INVENTOR(S) | : Radin et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 166 days.

Signed and Sealed this
Thirty-first Day of January, 2023

Katherine Kelly Vidal
*Director of the United States Patent and Trademark Office*